US012215170B2

(12) United States Patent
Du et al.

(10) Patent No.: US 12,215,170 B2
(45) Date of Patent: *Feb. 4, 2025

(54) ANTI-TMPRSS6 ANTIBODIES AND USES THEREOF

(71) Applicant: MABWELL THERAPEUTICS INC., San Diego, CA (US)

(72) Inventors: Xin Du, La Jolla, CA (US); Buxin Chen, San Marcos, CA (US); Yu Jean Wang, San Diego, CA (US)

(73) Assignee: MABWELL THERAPEUTICS INC., San Diego, CA (US)

( * ) Notice: Subject to any disclaimer, the term of this patent is extended or adjusted under 35 U.S.C. 154(b) by 214 days.

This patent is subject to a terminal disclaimer.

(21) Appl. No.: 17/916,008

(22) PCT Filed: Apr. 5, 2021

(86) PCT No.: PCT/US2021/025775
§ 371 (c)(1),
(2) Date: Sep. 29, 2022

(87) PCT Pub. No.: WO2021/207072
PCT Pub. Date: Oct. 14, 2021

(65) Prior Publication Data
US 2023/0203196 A1    Jun. 29, 2023

Related U.S. Application Data

(60) Provisional application No. 63/158,265, filed on Mar. 8, 2021, provisional application No. 63/006,695, filed on Apr. 7, 2020.

(51) Int. Cl.
*C07K 16/40* (2006.01)
*A61P 7/06* (2006.01)
*C12N 15/63* (2006.01)

(52) U.S. Cl.
CPC ............. *C07K 16/40* (2013.01); *A61P 7/06* (2018.01); *C12N 15/63* (2013.01); *C07K 2317/565* (2013.01)

(58) Field of Classification Search
None
See application file for complete search history.

(56) References Cited

FOREIGN PATENT DOCUMENTS

| WO | 2008097461 A2 | 8/2008 |
|---|---|---|
| WO | 2013070786 A1 | 5/2013 |
| WO | 2014099391 A1 | 6/2014 |
| WO | 2016071701 A1 | 5/2016 |
| WO | 2020065252 A1 | 4/2020 |
| WO | 2021105389 A1 | 6/2021 |
| WO | WO 2021207072 A1 | 10/2021 |
| WO | WO2022229150 A1 | 11/2022 |
| WO | WO 2022231999 A1 | 11/2022 |

OTHER PUBLICATIONS

Lob et al. 2022, TMPRSS6 Inhibition with a Monoclonal Antibody Improves Red Blood Cell Health and Reduces Hepatic Iron Loading in Mouse Models of Iron Overload Diseases. American Society of Hematology (ASH) 64th ASH Annual Meeting and Exposition, Dec. 12, 2022.

Wake Matthew et al, "Generation and Characterisation of KY1066, a Fully Human Antibody Targeting the Enzymatic Activity of Matriptase-2 for the Treatment of Iron Overload in Beta Thalassemia", Blood, American Society of Hematology, US,vol. 134, Nov. 13, 2019 (Nov. 13, 2019), p. 3532, DOI: 10.1182/BLOOD-2019-124075.

Anonymous, "Anti-Matriptase 2 antibody—Catalytic domain (ab56182) | Abcam", Jan. 1, 2016 (Jan. 1, 2016), p. 1-8,Retrieved from the Internet: URL:https://www.abcam.com/matriptase-2-antibody-catalytic-domain-ab56182.html.

Anonymous, "Matriptase 2 antibody | anti Matriptase 2 antibody | Biorbyt", Mar. 25, 2015 (Mar. 25, 2015), p. 1-4, Retrieved from the Internet: URL:https://www.biorbyt.com/matriptase-2-antibody-orb2471.html.

Schmidt et al, "An RNAi therapeutic targeting Tmprss6 decreases iron overload in Hfe−/− mice and ameliorates anemia and iron overload in murine beta-thalassemia intermedia", Blood,vol. 121, No. 7, Jan. 1, 2013 (Jan. 1, 2013), p. 1200-1208, DOI: 10.1182/blood-2012-09-453977.

Guo et al, "Reducing TMPRSS6 ameliorates hemochromatosis and beta-thalassemia in mice", Journal of Clinical Investigation, vol. 123. No. 4, Mar. 25, 2013 (Mar. 25, 2013), p. 1531-1541, XP055135245 DOI: 10.1172/JCI66969.

Frydlova et al, "Effect of Erythropoietin, Iron Deficiency and Iron Overload on Liver Matriptase-2 (TMPRSS6) Protein Content in Mice and Rats", PLOS One Jan. 1, 2016 (Jan. 1, 2016), p. e0148540-e0148540, DOI: 10.1371/journal.pone.0148540.

Ramsay et al, "Matriptase-2 (TMPRSS6): a proteolytic regulator of iron homeostasis", Haematologica, Fondazione Ferrata Storti, IT,vol. 94, No. 6, Apr. 18, 2009 (Apr. 18, 2009), p. 840-849, DOI: 10.3324/HAEMATOL.2008.001867.

Fung et al, "Manipulation of the hepcidin pathway for therapeutic purposes", Haematologica, vol. 98, No. 11, Nov. 1, 2013 (Nov. 1, 2013), p. 1667-1676, DOI: 10.3324/haematol.2013.084624.

Wang et al, "The role of TMPRSS6/matriptase-2 in iron regulation and anemia", Frontiers in Pharmacology May 19, 2014 (May 19, 2014), vol. 5, Retrieved from the Internet: URL:https://www.nobi.nlm.nih.gov/pmc/articles/PMC4053654/pdf/fphar-05-00114.pdf DOI: 10.3389/fphar.2014.00114.

Camaschella C., "Treating iron overload" N Engl Journal Med 368(24):2325-7, Jun. 13, 2013. DOI: 10.1056/NEJMcibr1304338.

(Continued)

*Primary Examiner* — Sharon X Wen
(74) *Attorney, Agent, or Firm* — Neal, Gerber & Eisenberg LLP

(57) ABSTRACT

Antibodies and antigen-binding fragments thereof that bind type II transmembrane serine protease 6 (TMPRSS6) on the surface of a cell and increase hepcidin expression, and methods for treating disorders of iron metabolism using anti TMPRSS6 antibodies and fragments, are provided.

20 Claims, 20 Drawing Sheets
Specification includes a Sequence Listing.

(56) References Cited

OTHER PUBLICATIONS

Du et al, Du, X. et al., "The Serine Protease TMPRSS6 Is Required to Sense Iron Deficiency" Science 2008. 320: 1088-1092 (May 23, 2008) DOI: 10.1126/science.1157121 Retrieved as HHS Public Access Author Manuscript PMC2430097 URL: https://www.ncbi.nlm.nih.gov/pmc/articles/PMC2430097/.

Wake et al 2019 "KY1066: Generation and characterisation of a fully human antibody targeting the enzymatic activity of matriptase-2 for the treatment of iron overload in β thalassemia" Poster No. 3532, American Society of Hematology (ASH) 61st Annual Meeting, Dec. 9, 2019.

International Preliminary Report on Patentability (IPRP) for International Application No. PCT/US2021/025775 issued Oct. 6, 2022.

Invitation to Pay Additional Fees for International Application No. PCT/US2023/080978, mailed Feb. 13, 2024.

International Search Report and Written Opinion for International Application No. PCT/US2023/080978, mailed Mar. 29, 2024.

[No Author Listed] Polycythemia vera: the natural history of 1213 patients followed for 20 years. Gruppo Italiano Studio Policitemia. Ann Intern Med. Nov. 1, 1995;123(9):656-64. doi: 10.7326/0003-4819-123-9-199511010-00003.

Akada et al., Conditional expression of heterozygous or homozygous Jak2V617F from its endogenous promoter induces a polycythemia vera-like disease. Blood. Apr. 29, 2010;115(17):3589-97. doi: 10.1182/blood-2009-04-215848. Epub Mar. 2, 2010.

Baxter et al., Acquired mutation of the tyrosine kinase JAK2 in human myeloproliferative disorders. Lancet. Mar. 19-25, 2005;365(9464):1054-61. doi: 10.1016/S0140-6736(05)71142-9.

Casu et al., Minihepcidin peptides as disease modifiers in mice affected by β-thalassemia and polycythemia vera. Blood. Jul. 14, 2016;128(2):265-76. doi: 10.1182/blood-2015-10-676742. Epub May 6, 2016.

Constantinescu et al., Functional Consequences of Mutations in Myeloproliferative Neoplasms. Hemasphere. Jun. 1, 2021;5(6):e578. doi: 10.1097/HS9.0000000000000578.

Du et al., The serine protease TMPRSS6 is required to sense iron deficiency. Science. May 23, 2008;320(5879):1088-92. doi: 10.1126/science.1157121. Epub May 1, 2008.

El-Beshlawy et al., Recent trends in treatment of thalassemia. Blood Cells Mol Dis. May 2019;76:53-58. doi: 10.1016/j.bcmd.2019.01.006. Epub Feb. 4, 2019.

Ginzburg et al., Dysregulated iron metabolism in polycythemia vera: etiology and consequences. Leukemia. Oct. 2018;32(10):2105-2116. doi: 10.1038/s41375-018-0207-9. Epub Jul. 24, 2018.

Grisouard et al., JAK2 exon 12 mutant mice display isolated erythrocytosis and changes in iron metabolism favoring increased erythropoiesis. Blood. Aug. 11, 2016;128(6):839-51. doi: 10.1182/blood-2015-12-689216. Epub Jun. 10, 2016.

Henninger et al., Practical guide to quantification of hepatic iron with MRI. Eur Radiol. Jan. 2020;30(1):383-393. doi: 10.1007/s00330-019-06380-9. Epub Aug. 7, 2019.

Hubbard SR. Mechanistic Insights into Regulation of JAK2 Tyrosine Kinase. Front Endocrinol (Lausanne). Jan. 5, 2018;8:361. doi: 10.3389/fendo.2017.00361.

James et al., A unique clonal JAK2 mutation leading to constitutive signalling causes polycythaemia vera. Nature. Apr. 28, 2005;434(7037):1144-8. doi: 10.1038/nature03546.

Jamieson et al., The JAK2 V617F mutation occurs in hematopoietic stem cells in polycythemia vera and predisposes toward erythroid differentiation. Proc Natl Acad Sci U S A. Apr. 18, 2006;103(16):6224-9. doi: 10.1073/pnas.0601462103. Epub Apr. 7, 2006.

Kautz et al., Identification of erythroferrone as an erythroid regulator of iron metabolism. Nat Genet. Jul. 2014;46(7):678-84. doi: 10.1038/ng.2996. Epub Jun. 1, 2014. Erratum in: Nat Genet. Apr. 2020;52(4):463. doi: 10.1038/s41588-019-0548-y.

Kleppe et al., JAK-STAT pathway activation in malignant and nonmalignant cells contributes to MPN pathogenesis and therapeutic response. Cancer Discov. Mar. 2015;5(3):316-31. doi: 10.1158/2159-8290.CD-14-0736. Epub Jan. 8, 2015.

Kwapisz et al., Decreased serum prohepcidin concentration in patients with polycythemia vera. J Zhejiang Univ Sci B. Nov. 2009;10(11):791-5. doi: 10.1631/jzus.B0920217.

Lee et al., Structural effects of clinically observed mutations in JAK2 exons 13-15: comparison with V617F and exon 12 mutations. BMC Struct Biol. Sep. 10, 2009;9:58. doi: 10.1186/1472-6807-9-58.

Lee et al., Volumetric Splenomegaly in Patients With Polycythemia Vera. J Korean Med Sci. Mar. 21, 2022;37(11):e87. doi: 10.3346/jkms.2022.37.e87.

Levine et al., Role of JAK2 in the pathogenesis and therapy of myeloproliferative disorders. Nat Rev Cancer. Sep. 2007;7(9):673-83. doi: 10.1038/nrc2210.

Liu et al., RBC distribution width predicts thrombosis risk in polycythemia vera. Leukemia. Feb. 2022;36(2):566-568. doi: 10.1038/s41375-021-01410-2. Epub Sep. 8, 2021.

Ma et al., Mutation profile of JAK2 transcripts in patients with chronic myeloproliferative neoplasias. J Mol Diagn. Jan. 2009;11(1):49-53. doi: 10.2353/jmoldx.2009.080114. Epub Dec. 12, 2008.

McMullin et al., LNK mutations and myeloproliferative disorders. Am J Hematol. Feb. 2016;91(2):248-51. doi: 10.1002/ajh.24259.

Mithoowani et al., Investigation and management of erythrocytosis. CMAJ. Aug. 10, 2020;192(32):E913-E918. doi: 10.1503/cmaj.191587.

Passamonti et al., Life expectancy and prognostic factors for survival in patients with polycythemia vera and essential thrombocythemia. Am J Med. Nov. 15, 2004;117(10):755-61. doi: 10.1016/j.amjmed.2004.06.032.

Passamonti et al., Molecular and clinical features of the myeloproliferative neoplasm associated with JAK2 exon 12 mutations. Blood. Mar. 10, 2011;117(10):2813-6. doi: 10.1182/blood-2010-11-316810. Epub Jan. 11, 2011.

Regimbeau et al., Genetic Background of Polycythemia Vera. Genes (Basel). Apr. 2, 2022;13(4):637. doi: 10.3390/genes13040637.

Spivak JL. The polycythemia vera stem cell. Leuk Suppl. Dec. 2014;3(Suppl 1):S23-4. doi: 10.1038/leusup.2014.13. Epub Dec. 17, 2014.

Stein et al., Polycythemia Vera: An Appraisal of the Biology and Management 10 Years After the Discovery of JAK2 V617F. J Clin Oncol. Nov. 20, 2015;33(33):3953-60. doi: 10.1200/JCO.2015.61.6474. Epub Aug. 31, 2015.

Tefferi et al., Targeted deep sequencing in polycythemia vera and essential thrombocythemia. Blood Adv. Nov. 22, 2016;1(1):21-30. doi: 10.1182/bloodadvances.2016000216.

Verstovsek et al., Markers of iron deficiency in patients with polycythemia vera receiving ruxolitinib or best available therapy. Leuk Res. May 2017;56:52-59. doi: 10.1016/j.leukres.2017.01.032. Epub Jan. 31, 2017.

Wang et al., The role of TMPRSS6/matriptase-2 in iron regulation and anemia. Front Pharmacol. May 19, 2014;5:114. doi: 10.3389/fphar.2014.00114.

Tamm et al., IgG Binding Sites on Human FCγ Receptors. International Reviews of Immunology. 1997; 16:57-85. doi.org/10.3109/08830189709045703.

Jefferis et al. Interaction sites on human IgG-Fc for FcγR: current models. Immunology Letters. Jun. 3, 2002; 82:57-65. doi.org/10.1016/S0165-2478(02)00019-6.

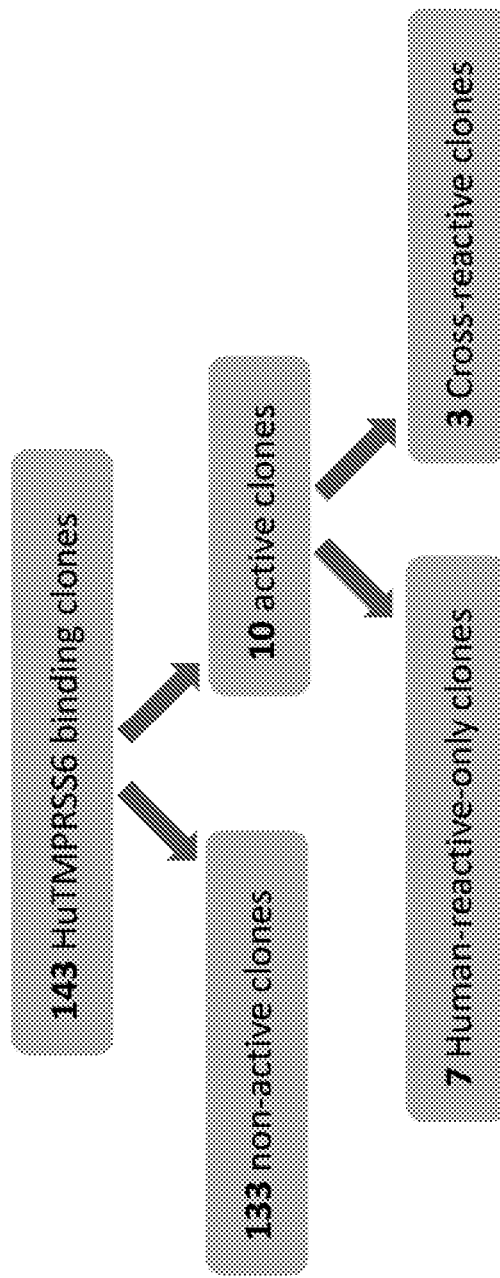
FIG. 1 Cascade screening for anti-TMPRSS6 antibodies.

| | $K_D$ (M) | $k_{on}$ (1/Ms) | $k_{off}$ (1/s) | $R^2$ |
|---|---|---|---|---|
| MWTx-001 | 6.6e-10 | 2.08e+05 | 1.37e-04 | 0.9991 |
| MWTx-002 | 8.2e-10 | 1.46e+05 | 1.19e-04 | 0.9996 |
| MWTx-003 | 6.4e-09 | 2.42e+04 | 1.55e-04 | 0.9992 |
| hzMWTx-001Var | 3.36e-09 | 1.26e+05 | 4.23e-04 | 0.9999 |
| hzMWTx-002Var | 1.84e-08 | 5.95e+04 | 1.09e-03 | 0.9977 |
| hzMWTx-003Var | 1.37e-08 | 4.79e+03 | 6.58e-05 | 0.9996 |

FIG. 3M

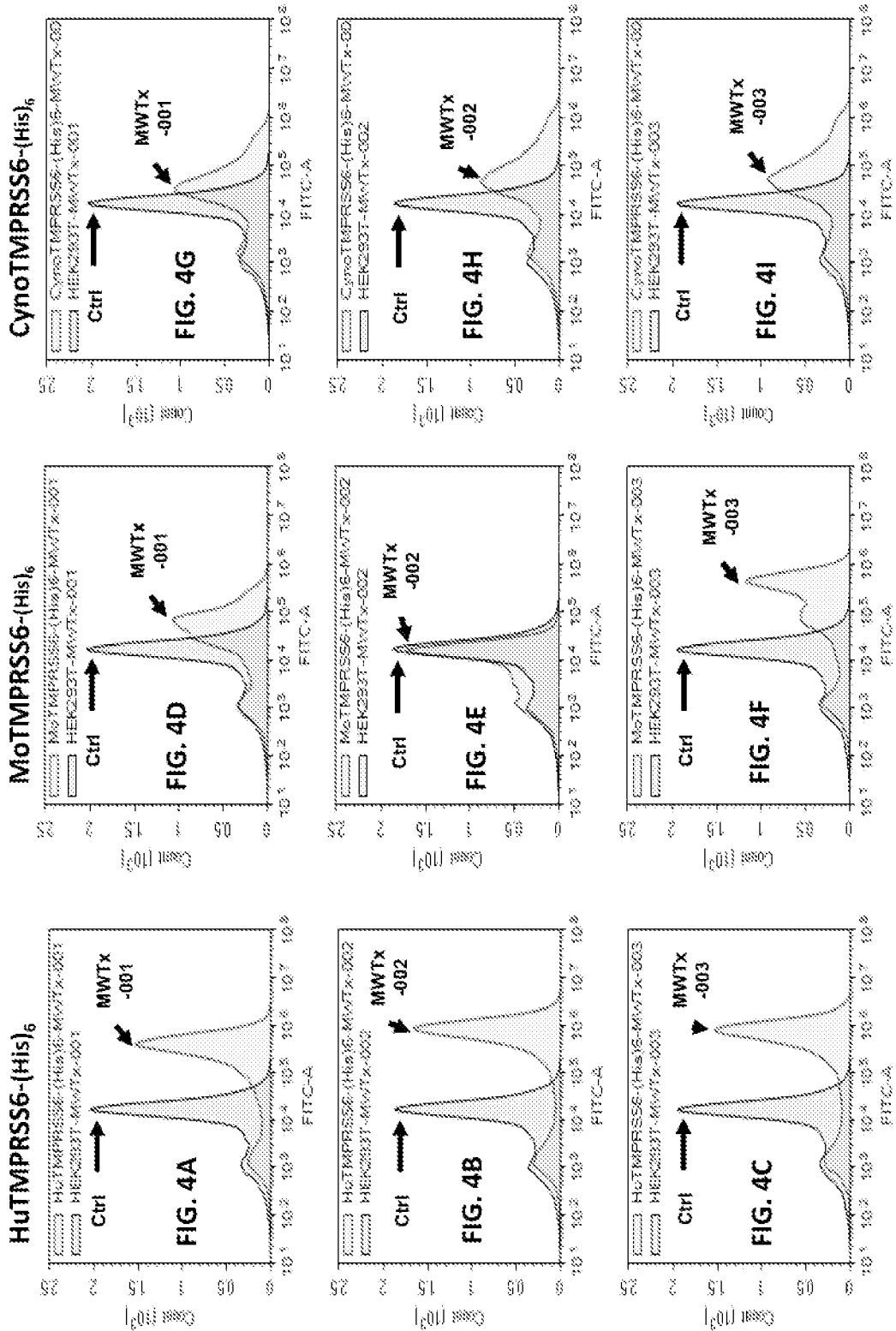

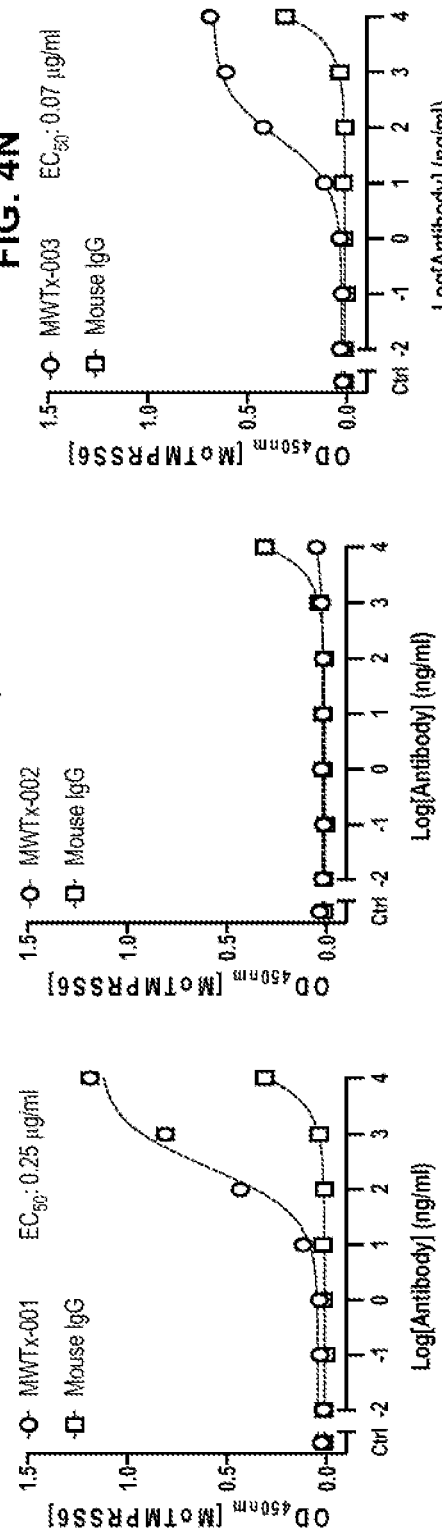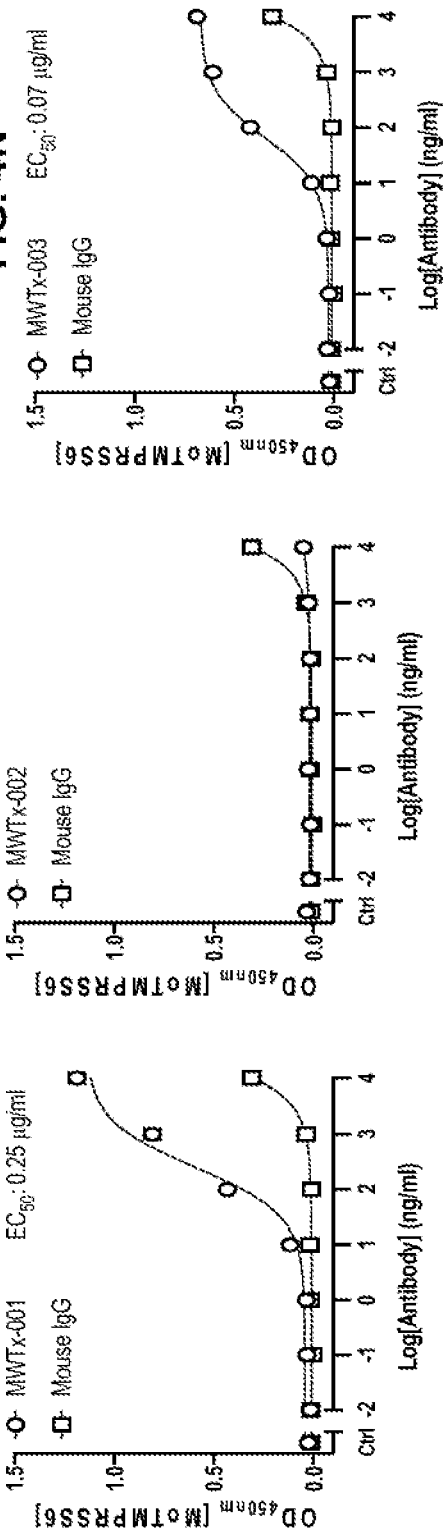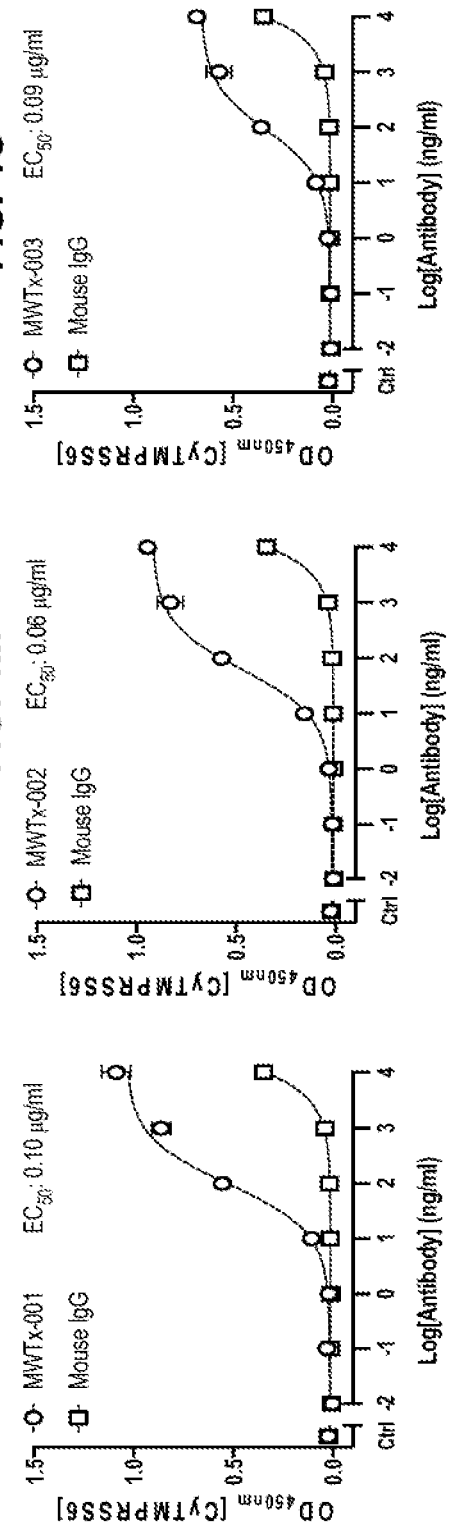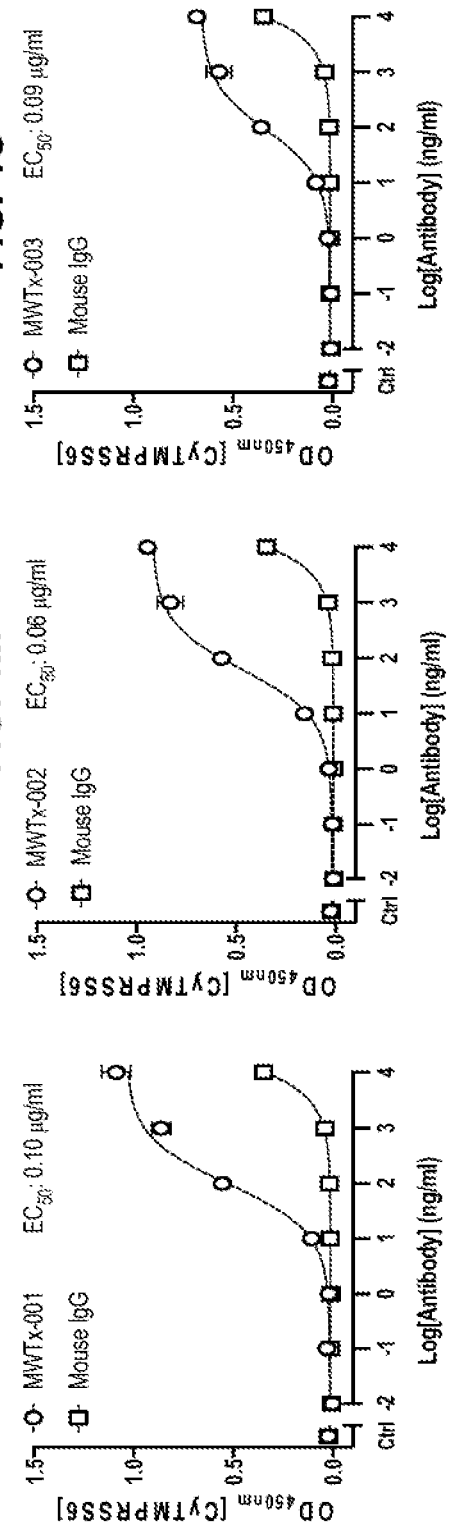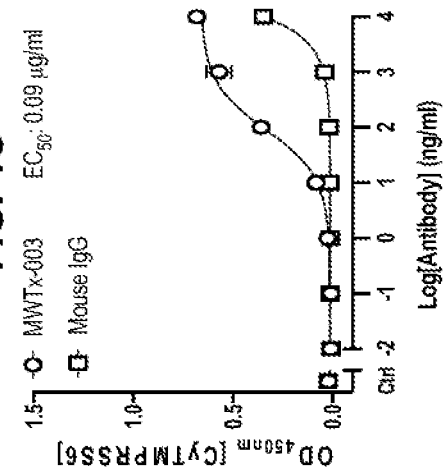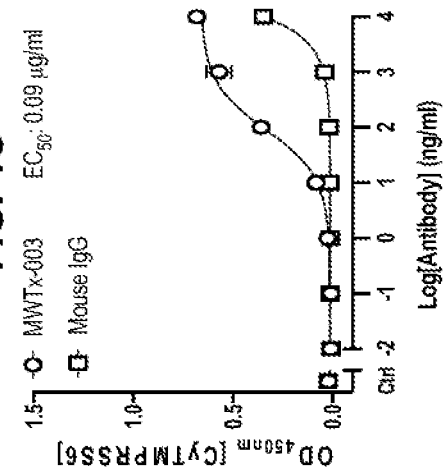

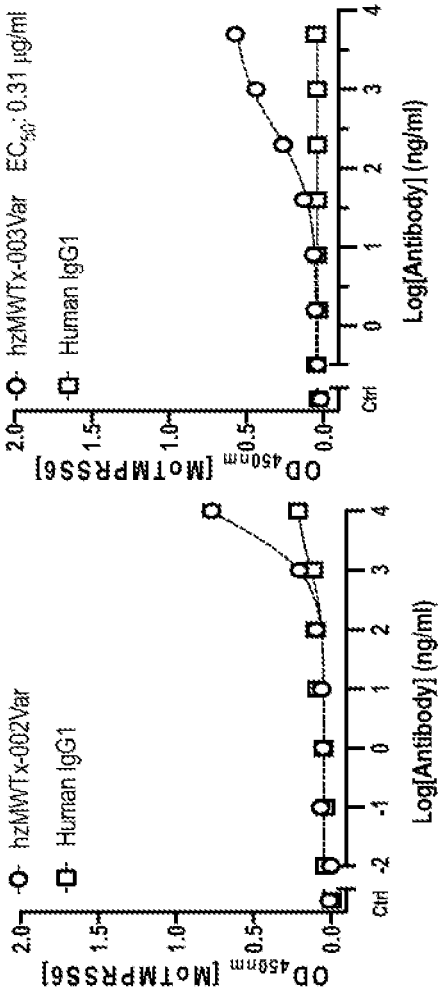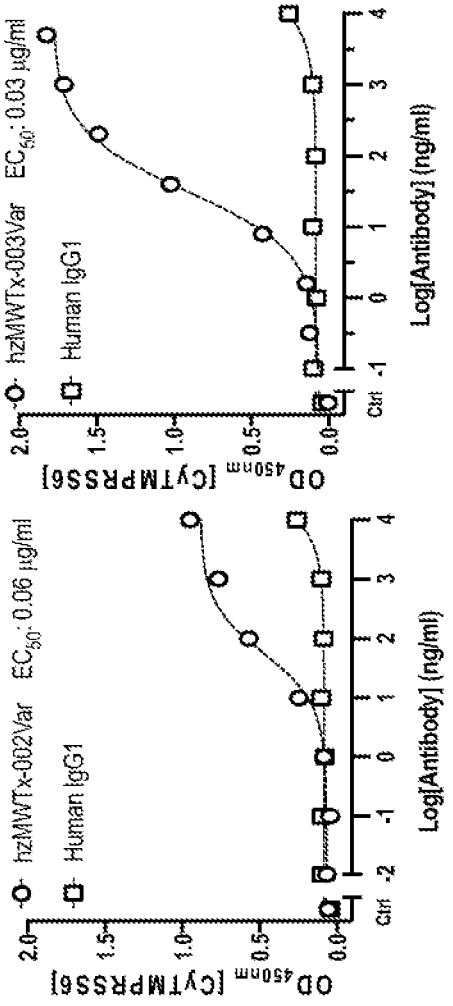

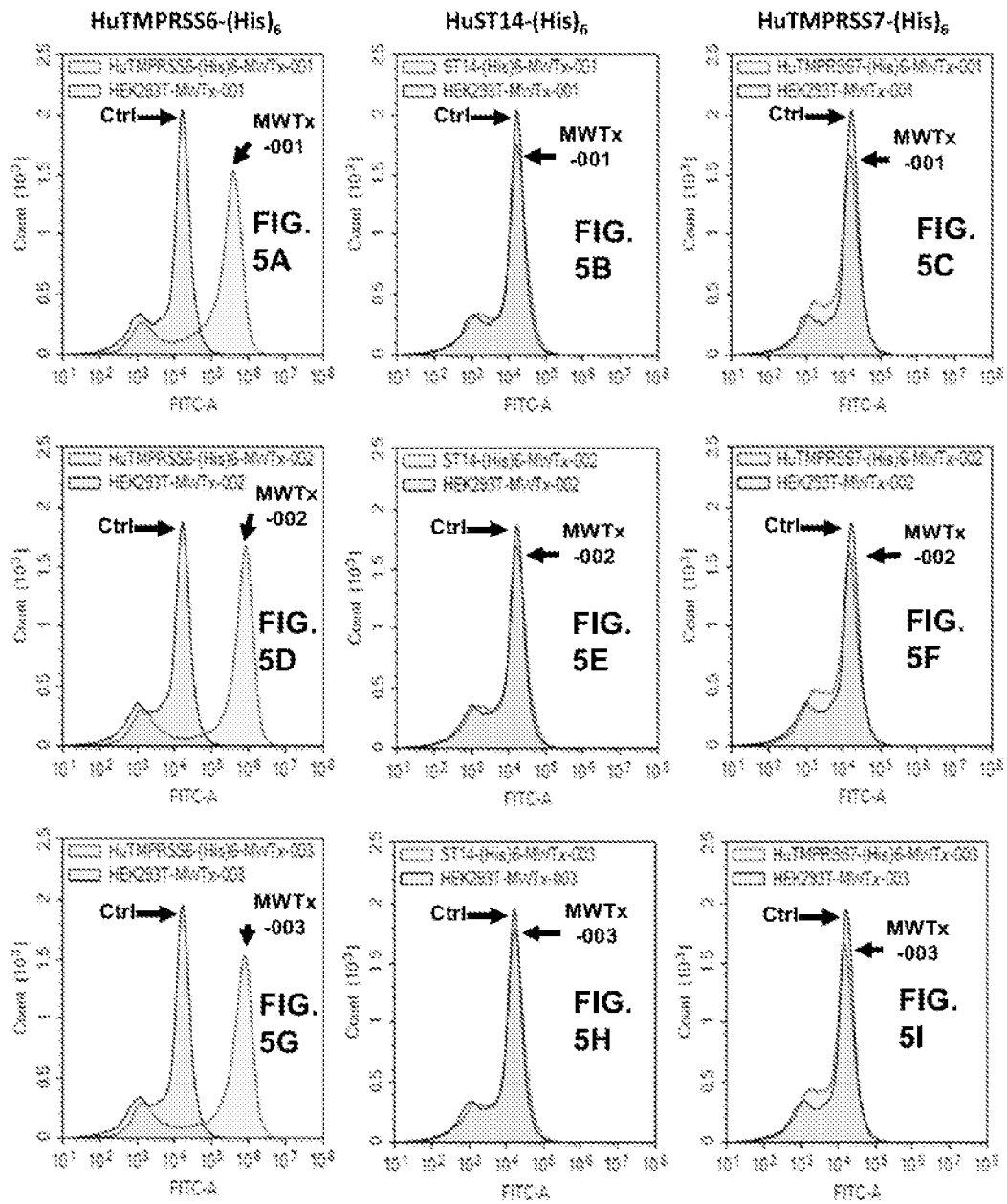

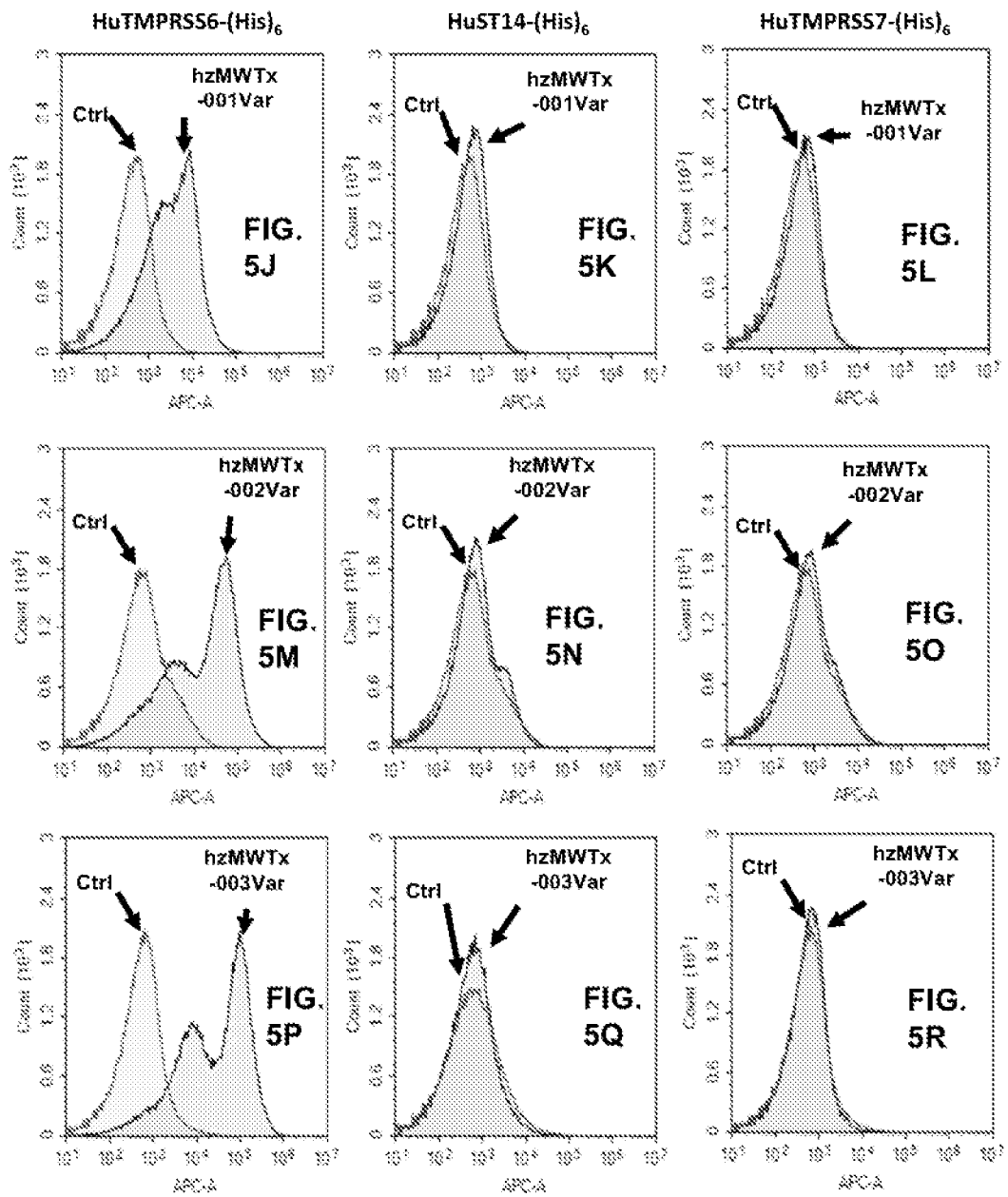

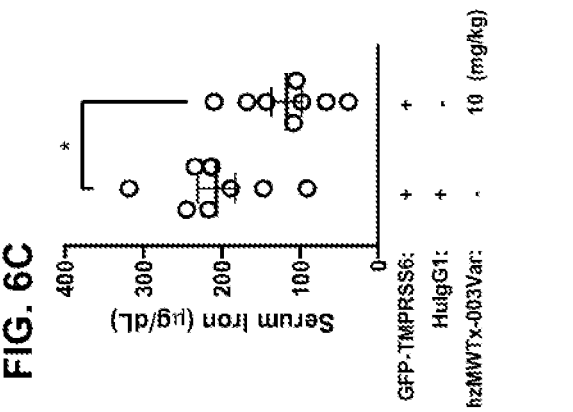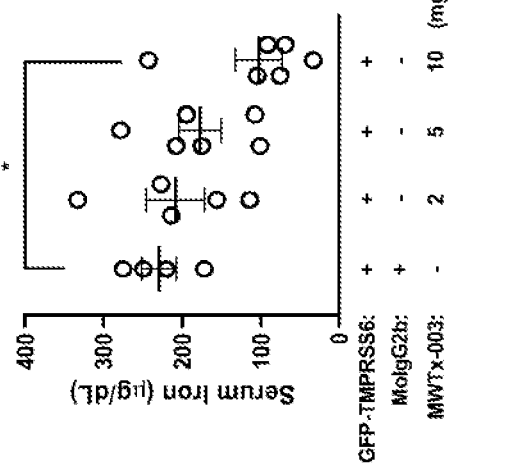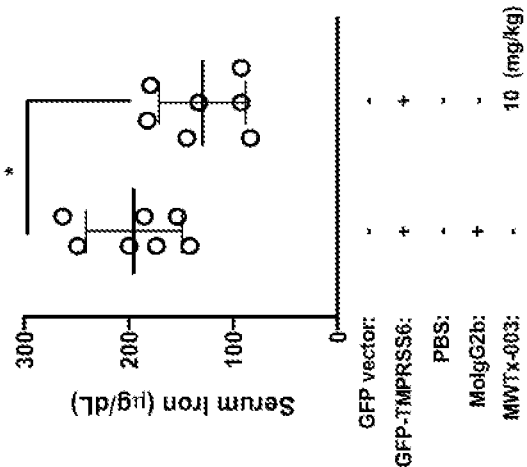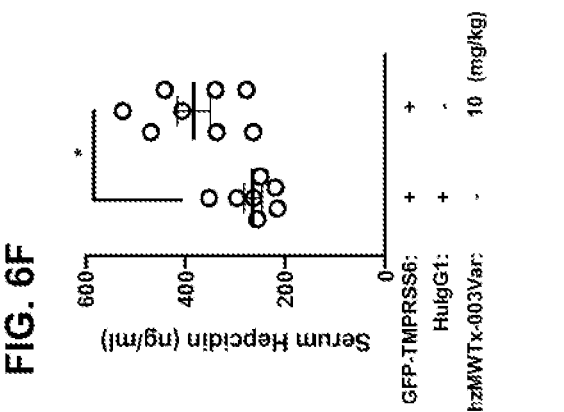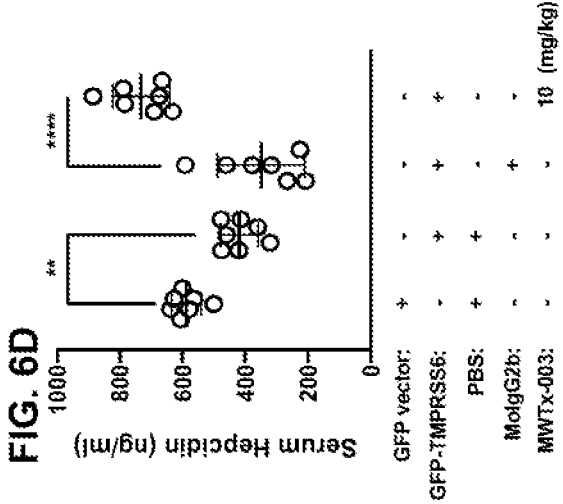
FIG. 6A, FIG. 6B, FIG. 6C, FIG. 6D, FIG. 6E, FIG. 6F

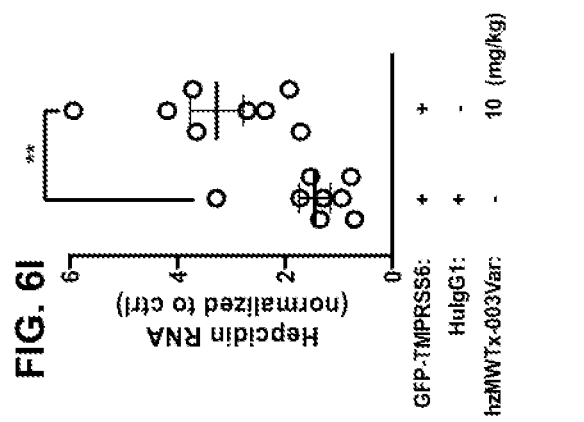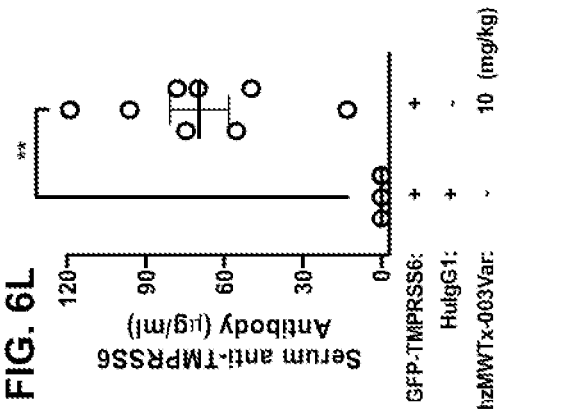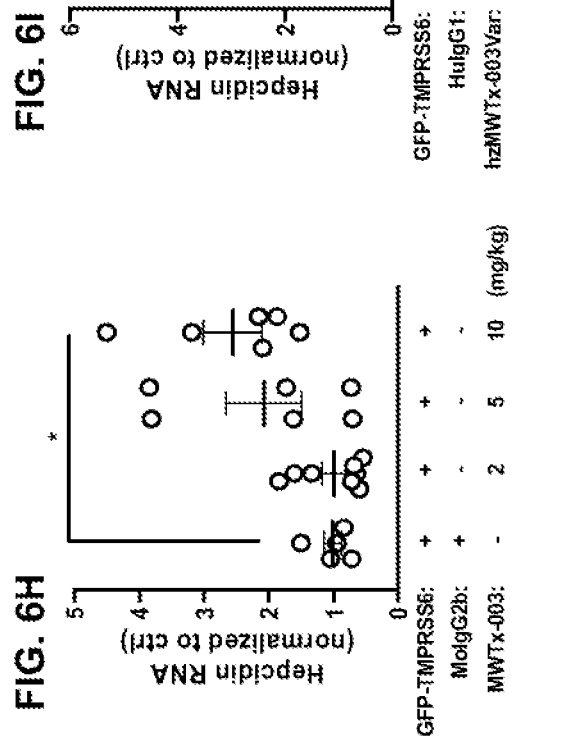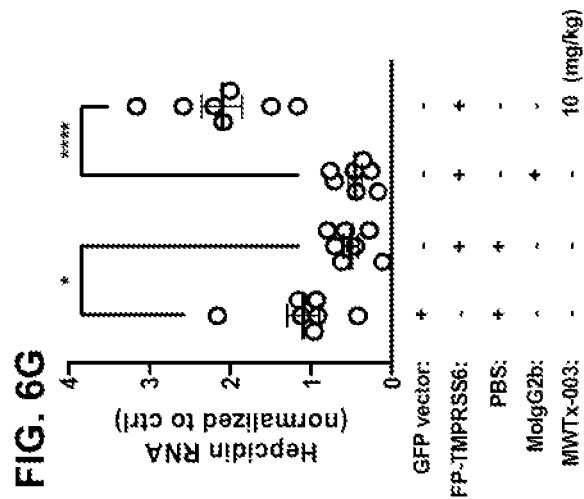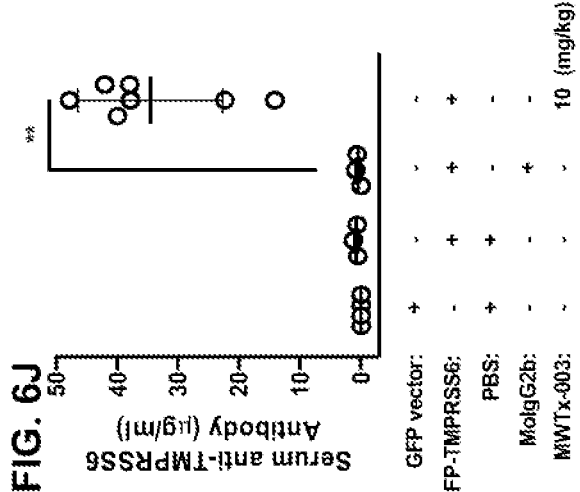

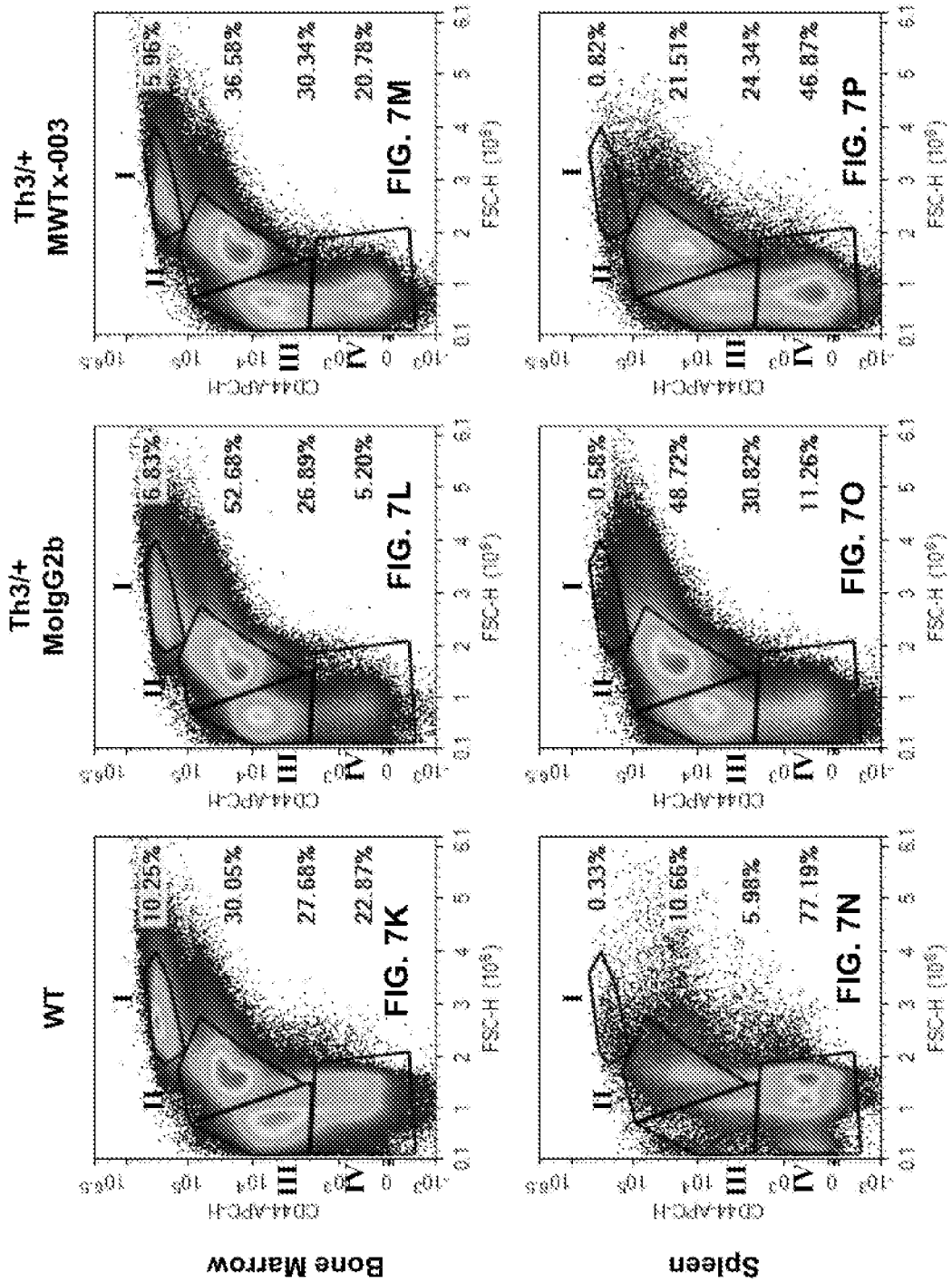

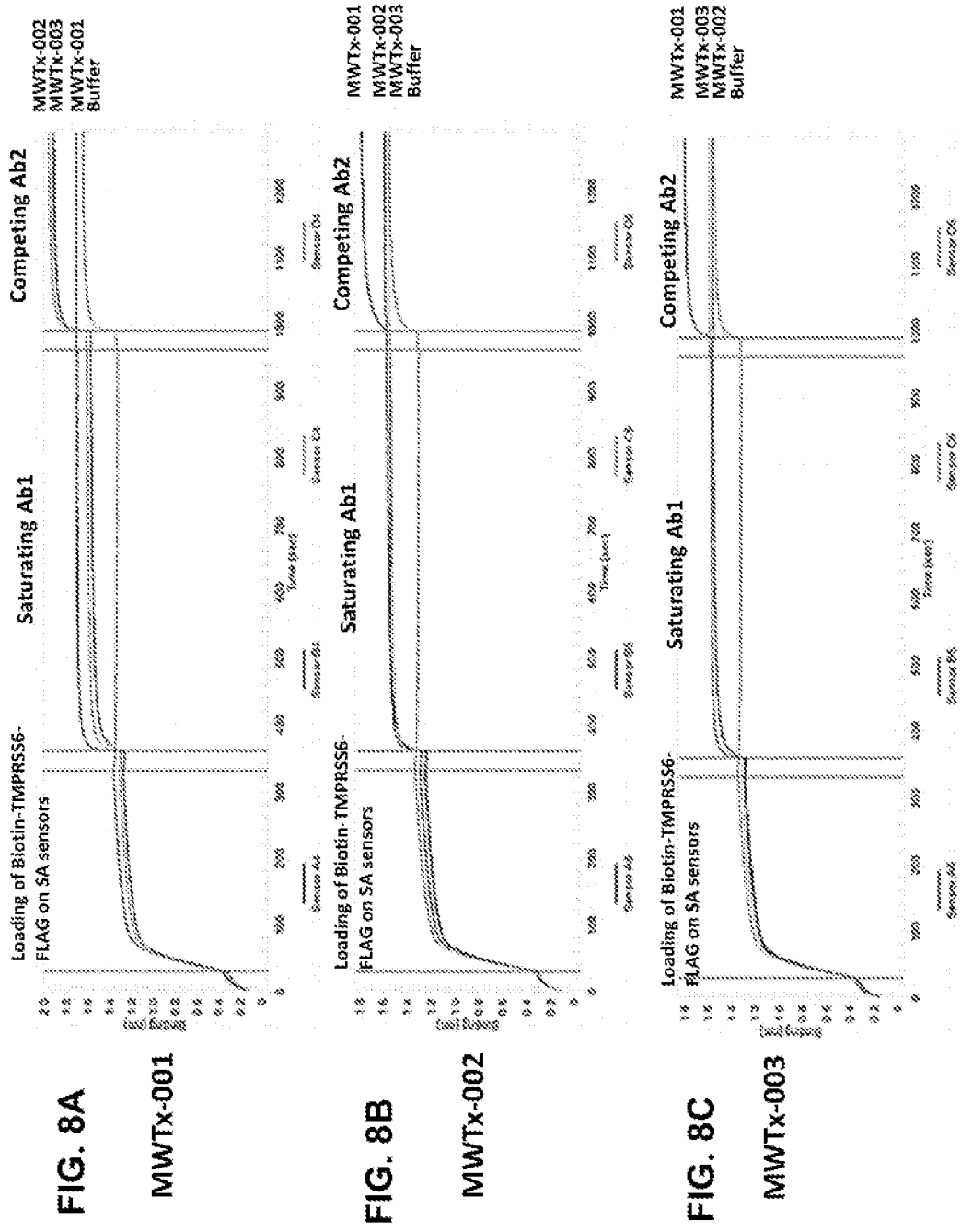

| Association Signal | MWTx-001 | MWTx-002 | MWTx-003 |
|---|---|---|---|
| MWTx-001 | 0.0065 | 0.2379 | 0.2327 |
| MWTx-002 | 0.3401 | 0.0100 | 0.0163 |
| MWTx-003 | 0.3391 | 0.0235 | 0.0190 |
| Buffer | 0.3017 | 0.2319 | 0.2369 |

FIG. 8D

ANTI-TMPRSS6 ANTIBODIES AND USES THEREOF

RELATED APPLICATIONS

The instant application is a national phase application under 35 U.S.C. § 371, of International Application No. PCT/US2021/025775 entitled "Anti-TMPRSS6 Antibodies and Uses Thereof" filed Apr. 5, 2021, which claims benefit of priority to U.S. Provisional Application No. 63/006,695 entitled "Anti-TMPRSS6 Antibodies and Uses Thereof" filed Apr. 7, 2020, and U.S. Provisional Application No. 63/158,265 entitled "Anti-TMPRSS6 Antibodies and Uses Thereof" filed Mar. 8, 2021, the entire contents of each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Mar. 29, 2021, is named 1121_101PCT_SL.txt and is 132,677 bytes in size.

FIELD OF THE INVENTION

The present disclosure relates to antibodies and antigen-binding fragments that bind TMPRSS6, and treating disorders of iron metabolism using antibodies and antigen-binding fragments that bind TMPRSS6.

BACKGROUND

Type II transmembrane serine protease 6 (TMPRSS6) is encoded by the TMPRSS6 gene and primarily expressed in liver. The structure of TMPRSS6 includes a type II transmembrane domain, followed by a sea urchin sperm protein, enteropeptidase and agrin (SEA) domain, a stem region containing two complement factor C1r/C1s, urchin embryonic growth factor and bone morphogenetic protein (CUB) domains and three low-density lipoprotein receptor (LDLR) class A repeats, and a C-terminal trypsin-like serine protease domain (Wang, C.-Y. et al., Front. Pharmacol, 2014, 5:114). Aliases for TMPRSS6 (EC 3.4.21) include: matriptase-2; transmembrane protease serine 6; membrane-bound mosaic serine proteinase matriptase-2; and MT2.

TMPRSS6 plays a significant role in iron homeostasis through the BMP-SMAD signaling pathway that regulates the expression of hepcidin, a hormone that controls iron absorption and mobilization from iron stores. Hepcidin (also known as: HAMP (hepcidin anti-microbial protein or peptide), encoded by HAP in humans and non-human primates, and Hamp in mice and rats) regulates systemic iron homeostasis by controlling the functional activity of the sole iron efflux channel ferroportin. Hepcidin can lower plasma iron levels by binding to ferroportin and causing internalization and degradation of the complex, thereby preventing iron absorption at the small intestine and release of stored iron. Chronic elevation of hepcidin levels causes systemic iron deficiency, and hepcidin deficiency causes systemic iron overload.

TMPRSS6 negatively regulates the production of hepcidin through a transmembrane signaling pathway that is triggered by iron deficiency and suppresses HAMP activation (Du, X. et al., Science 2008, 320: 1088-1092; Wang, C.-Y. et al., Front. Pharmacol. 2014, 5:114). Low blood iron levels trigger this pathway to reduce hepcidin production, which allows more iron from the diet to be absorbed through the intestines and transported out of storage sites into the bloodstream. In rats under acute iron deprivation, hepatic TMPRSS6 protein levels are upregulated, leading to suppressed hepcidin expression and production (Wang, C.-Y. et al., Front. Pharmacol. 2014, 5:114). Mutations throughout the TMPRSS6 molecule, and especially in the extracellular domain, have been identified in subjects with iron deficiency anemia, in particular iron-refractory iron deficiency anemia (IRIDA) that is unresponsive to oral iron treatment and only partially responsive to parenteral iron therapy (Wang, C.-Y. et al., Front. Pharmacol. 2014, 5:114). Loss-of-function mutations in TMPRSS6 in humans result in elevated levels of hepcidin and iron-deficiency anemia (Camaschella, C., N Engl Journal Med 2013, 168:24) as overproduction of hepcidin leads to defective iron absorption and utilization.

Iron overload disorders result when excess iron accumulates in tissues and organs to an extent that their normal functions are disrupted. Iron toxicity is a common complication of iron overload disorders, leading to high rates of mortality as a result of iron accumulation in major organs. β-thalassemia is an iron overload disorder that occurs when mutations in the HBB gene cause reduced or absent production of β-globin (beta globin) that lead to apoptosis of erythroblasts and a shortage of mature red blood cells, resulting in ineffective erythropoiesis that causes anemia and hyperabsorption of iron leading to iron toxicity. In patients with β-thalassemia, hepcidin is abnormally suppressed in relation to the patient's state of iron loading, creating a hepcidin deficiency that in turn allows excessive iron absorption and development of systemic iron overload. Ineffective erythropoiesis in other disorders such as MDS (myelodysplastic syndrome), dyserythropoietic anemia, sideroblastic anemia, is likewise characterized by low hepcidin leading to iron overload. Hemochromatosis, e.g., hemochromatosis type 1 or hereditary hemochromatosis is an iron overload disorder characterized by excess intestinal absorption of dietary iron and a pathological increase in total body iron stores. Current standards of care for treating iron overload disorders include blood transfusions for ineffective erythropoiesis that can further exacerbate iron overload, iron chelation with poor patient compliance, and phlebotomy or splenectomy to manage symptoms. Therapeutic approaches currently under development include gene therapy targeting the HBB gene, gene therapy and gene editing targeting other relevant genes, hepeidin mimetics, Fc-fusion proteins that target TGF superfamily ligands to inhibit SMAD signaling, antisense RNA drugs targeting TMPRSS6 (e.g., El-Beshlawy A., et al., Blood Cells, Molecules and Diseases 2019, 76: 53-58), and iRNA drugs targeting TMPRSS6.

SUMMARY

The invention relates to novel antibodies and antigen-binding fragments thereof that bind TMPRSS6, and methods of making and using antibodies and antigen-binding fragments thereof that bind TMPRSS6.

The present disclosure provides anti-TMPRSS6 antibodies, nucleic acids encoding anti-TMPRSS6 antibodies, and methods of making and using anti-TMPRSS6 antibodies. Anti-TMPRSS6 antibodies as disclosed herein encompass anti-TMPRSS6 antibodies and fragments thereof that are capable of binding TMPRSS6. Anti-TMPRSS6 antibodies as disclosed herein are capable of binding to human TMPRSS6 on the surface of a cell expressing human TMPRSS6. The present disclosure provides anti-TMPRSS6 antibodies for therapeutic and diagnostic uses. Anti-TM- PRSS6 antibodies as disclosed herein can be used to treat disorders of iron metabolism such as iron overload disorders, in particular β-thalassemias including but not limited to non-transfusion dependent thalassemia, and other disorders of ineffective erythropoiesis.

In one aspect, anti-TMPRSS6 antibodies are provided that are capable of binding to TMPRSS6 on the surface of a cell expressing TMPRSS6 and modulating the activity of at least one component involved in iron metabolism, where a component may be a molecule or a biological process associated with the function of TMPRSS6. In certain embodiments, anti-TMPRSS6 antibodies disclosed herein are capable of modulating the activity of at least one component involved in regulating hepcidin expression. In certain embodiments, anti-TMPRSS6 antibodies disclosed herein are capable of substantially inhibiting TMPRSS6 suppression of hepcidin expression. In certain embodiments, anti-TMPRSS6 antibodies disclosed herein are capable of increasing hepcidin expression. In certain embodiments, anti-TMPRSS6 antibodies disclosed herein are capable of increasing the activity of the hepcidin promoter. In certain embodiments, anti-TMPRSS6 antibodies disclosed herein are capable of substantially inhibiting TMPRSS6 suppression of the BMP/SMAD pathway-induced expression of hepcidin. Anti-TMPRSS6 antibodies disclosed herein may modulate hepcidin expression, including but not limited to substantially inhibiting TMPRSS6 suppression of hepcidin expression, increasing hepcidin expression, increasing hepcidin promoter activity, or substantially inhibiting TMPRSS6 suppression of the BMP/SMAD pathway-induced expression of hepcidin, in a dose-dependent manner. In certain embodiments, anti-TMPRSS6 antibodies disclosed herein are capable of modulating hepcidin expression in a dose-dependent manner. In certain embodiments, anti-TMPRSS6 antibodies disclosed herein are capable of increasing serum hepcidin levels in a dose-dependent manner when administered to a subject. In certain embodiments, anti-TMPRSS6 antibodies disclosed herein are capable of reducing serum iron levels in a dose-dependent manner when administered to a subject. In certain embodiments, anti-TMPRSS6 antibodies disclosed herein are capable of increasing liver hepcidin RNA levels in a dose-dependent manner when administered to a subject. In certain embodiments, anti-TMPRSS6 antibodies disclosed herein are capable of reducing liver non-heme iron, increasing serum hepcidin, increasing liver hepcidin RNA, reducing splenomegaly, increasing red blood count (RBC), increasing hematocrit (HCT), reducing red cell distribution width (RDW), and increased production of mature red cells (increased erythropoiesis) when administered to a subject known or suspected to have an iron overload disorder, in particular a β-thalassemia.

In another aspect, anti-TMPRSS6 antibodies disclosed herein show cross-reactivity with at least one non-human TMPRSS6. In certain embodiments, anti-TMPRSS6 antibodies disclosed herein are capable of binding to at least one non-human TMPRSS6 on the surface of a cell expressing the at least one non-human TMPRSS6. Anti-TMPRSS6 antibodies disclosed herein may be capable of binding human TMPRSS6 and mouse TMPRSS6. Anti-TMPRSS6 antibodies disclosed herein may be capable of binding to human TMPRSS6 and cynomolgus monkey TMPRSS6. Anti-TMPRSS6 antibodies disclosed herein may be capable of binding to each of human TMPRSS6, mouse TMPRSS6, and cynomolgus monkey TMPRSS6.

In another aspect, anti-TMPRSS6 antibodies disclosed herein specifically bind to TMPRSS6 (matriptase-2). In certain embodiments, anti-TMPRSS6 antibodies disclosed herein bind to TMPRSS6 (matriptase-2) and do not show detectable binding to matriptase homologues. In certain embodiments, anti-TMPRSS6 antibodies disclosed herein bind to human TMPRSS6 (matriptase-2) and do not show detectable binding to human matriptase-1 (ST14). In certain embodiments, anti-TMPRSS6 antibodies disclosed herein bind to human TMPRSS6 (matriptase-2) and do not show detectable binding to human matriptase-3 (TMPRSS7). In certain embodiments, anti-TMPRSS6 antibodies disclosed herein bind to human TMPRSS6 (matriptase-2) and do not show detectable binding to either of human matriptase-1 (ST14) or human matriptase-3 (TMPRSS7).

An anti-TMPRSS6 antibody disclosed herein may be a monoclonal antibody, a humanized antibody, a chimeric antibody, a single chain antibody, a Fab fragment, a single-chain variable fragment (scFv), a recombinant antibody, an aptamer, a single-domain antibody (VHH, nanobody), or other TMPRSS6-binding fragment or variant. In certain embodiments, an anti-TMPRSS6 antibody disclosed herein may comprise a framework in which amino acids have been substituted into an existing antibody framework, in particular to influence properties such as antigen-binding ability. In certain embodiments, an anti-TMPRSS6 antibody disclosed herein may comprise complementarity determining regions (CDRs) from a source (parental) antibody that have been grafted (fused) into a framework from a different type (class) of antibody and/or from a different organism than the parental antibody, in particular an acceptor human framework. In certain embodiments, an anti-TMPRSS6 antibody disclosed herein may comprise a framework in which amino acids have been substituted, mutated, or replaced in regions outside of the CDRs to influence properties such as antigen-binding or antibody structure, e.g., in the variable region framework surrounding the CDRs and/or in a constant region, in particular the Fc region. In certain embodiments, one or more of the CDRs have been substituted, mutated, or replaced. In certain embodiments, an anti-TMPRSS6 antibody disclosed herein may be a humanized anti-TMPRSS6 antibody variant.

In certain embodiments, anti-TMPRSS6 antibodies disclosed herein comprise at least one polypeptide having an amino acid sequence as set forth in Table 1, Table 2, or Table 3, or a sequence substantially identical (e.g., at least 85%, 90%, 92%, 95%, 97%, or 98%, 99% identical) to an amino acid sequence as set forth in Table 1, Table 2, or Table 3. Anti-TMPRSS6 antibodies disclosed herein may comprise at least one polypeptide having an amino acid sequence selected from the following, or a sequence substantially identical (e.g., at least 85%, 90%, 92%, 95%, 97%, or 98%, 99% identical) to at least one polypeptide having an amino acid sequence selected from the following: SEQ ID NO: 1; SEQ ID NO: 2; SEQ ID NO: 3; SEQ ID NO: 4; SEQ ID NO: 6; SEQ ID NO: 7; SEQ ID NO: 8; SEQ ID NO: 9; SEQ ID NO: 11; SEQ ID NO: 12; SEQ ID NO: 13; SEQ ID NO: 14; SEQ ID NO: 16; SEQ ID NO: 17; SEQ ID NO: 18; SEQ ID NO: 19; SEQ ID NO: 21; SEQ ID NO: 22; SEQ ID NO: 23; SEQ ID NO: 24; SEQ ID NO: 26; SEQ ID NO: 27; SEQ ID NO: 28; SEQ ID NO: 29; SEQ ID NO: 31; SEQ ID NO: 32; SEQ ID NO: 33; SEQ ID NO: 34; SEQ ID NO: 36; SEQ ID NO: 37; SEQ ID NO: 38; SEQ ID NO: 39; SEQ ID NO: 41; SEQ ID NO: 42; SEQ ID NO: 43; SEQ ID NO: 44; SEQ ID NO: 46; SEQ ID NO: 47; SEQ ID NO: 48; SEQ ID NO: 49; SEQ ID NO: 51; SEQ ID NO: 52; SEQ ID NO: 53; SEQ ID NO: 54; SEQ ID NO: 56; SEQ ID NO: 57; SEQ ID NO: 58; SEQ ID NO: 59; SEQ NO: 61; SEQ ID NO: 63; SEQ ID NO: 65; SEQ ID NO: 67; SEQ ID NO: 69; SEQ ID NO: 71;

SEQ ID NO: 73; SEQ ID NO: 75; SEQ ID NO: 77; SEQ ID NO: 79; SEQ ID NO: 81; or SEQ ID NO: 83.

In one embodiment, an anti-TMPRSS6 antibody disclosed herein comprises a heavy chain (HC) variable region polypeptide of the amino acid sequence set forth in SEQ ID NO: 1 or a sequence substantially identical to SEQ ID NO: 1, and a light chain (LC) variable region polypeptide of the amino acid sequence set forth in SEQ ID NO: 6 or a sequence substantially identical to SEQ ID NO: 6. In one embodiment, an anti-TMPRSS6 antibody disclosed herein comprises a heavy chain complementarity determining region 1 (HC CDR1) of the amino acid sequence set forth in SEQ ID NO: 2, a heavy chain complementarity determining region 2 (HC CDR2) of the amino acid sequence set forth in SEQ ID NO: 3, a heavy chain complementarity determining region 3 (HC CDR3) of the amino acid sequence set forth in SEQ ID NO: 4; a light chain complementarity determining region 1 (LC CDR1) of the amino acid sequence set forth in SEQ ID NO: 7, a light chain complementarity determining region 2 (LC CDR2) of the amino acid sequence set forth in SEQ ID NO: 8, and a light chain complementarity determining region 3 (LC CDR3) of the amino acid sequence set forth in SEQ ID NO: 9; or a variant of said antibody comprising 1, 2, 3, 4, 5, or 6 amino acid substitutions in the CDR regions. In one non-limiting embodiment, an anti-TMPRSS6 antibody disclosed herein is the antibody identified herein as MWTx-001, comprising an HC polypeptide having the amino acid sequence set forth in SEQ ID NO: 61 and an LC polypeptide having the amino acid sequence set forth in SEQ ID NO: 63.

In one embodiment, an anti-TMPRSS6 antibody disclosed herein comprises an HC variable region polypeptide of the amino acid sequence set forth in SEQ ID NO: 11 or a sequence substantially identical to SEQ ID NO: 11, and an LC variable region polypeptide of the amino acid sequence set forth in SEQ ID NO: 16 or a sequence substantially identical to SEQ ID NO: 16. In one embodiment, an anti-TMPRSS6 antibody disclosed herein comprises an HC CDR1 of the amino acid sequence set forth in SEQ ID NO: 12, an HC CDR2 of the amino acid sequence set forth in SEQ ID NO: 13, an HC CDR3 of the amino acid sequence set forth in SEQ ID NO: 14; an LC CDR1 of the amino acid sequence set forth in SEQ ID NO: 17, an LC CDR2 of the amino acid sequence set forth in SEQ ID NO: 18, and an LC CDR3 of the amino acid sequence set forth in SEQ ID NO: 19, or a variant of said antibody comprising 1, 2, 3, 4, 5, or 6 amino acid substitutions in the CDR regions. In one non-limiting embodiment, an anti-TMPRSS6 antibody disclosed herein is of the antibody identified herein as MWTx-002, comprising an HC polypeptide having the amino acid sequence set forth in SEQ ID NO: 65 and an LC polypeptide having the amino acid sequence set forth in SEQ ID NO: 67.

In one embodiment, an anti-TMPRSS6 antibody disclosed herein comprises an HC variable region polypeptide of the amino acid sequence set forth in SEQ ID NO: 21 or a sequence substantially identical to SEQ ID NO: 21, and an LC variable region polypeptide of the amino acid sequence set forth in SEQ ID NO: 26 or a sequence substantially identical to SEQ ID NO: 26. In one embodiment, an anti-TMPRSS6 antibody disclosed herein comprises an HC CDR1 of the amino acid sequence set forth in SEQ ID NO: 22, an HC CDR2 of the amino acid sequence set forth in SEQ ID NO: 23, an HC CDR3 of the amino acid sequence set forth in SEQ ID NO: 24; an LC CDR1 of the amino acid sequence set forth in SEQ ID NO: 27, an LC CDR2 of the amino acid sequence set forth in SEQ ID NO: 28, and an LC CDR3 of the amino acid sequence set forth in SEQ ID NO: 29, or a variant of said antibody comprising 1, 2, 3, 4, 5, or 6 amino acid substitutions in the CDR regions. In one non-limiting embodiment, an anti-TMPRSS6 antibody disclosed herein is the antibody identified herein as MWTx-003, comprising an HC polypeptide having the amino acid sequence set forth in SEQ ID NO: 69 and an LC polypeptide having the amino acid sequence set forth in SEQ ID NO: 71.

In one embodiment, an anti-TMPRSS6 antibody disclosed herein comprises an HC variable region polypeptide of the amino acid sequence set forth in SEQ ID NO: 31 or a sequence substantially identical to SEQ ID NO: 31, and an LC variable region polypeptide of the amino acid sequence set forth in SEQ ID NO: 36 or a sequence substantially identical to SEQ ID NO: 36. In one embodiment, an anti-TMPRSS6 antibody disclosed herein comprises an HC CDR1 of the amino acid sequence set forth in SEQ ID NO: 32, an HC CDR2 of the amino acid sequence set forth in SEQ ID NO: 33, an HC CDR3 of the amino acid sequence set forth in SEQ ID NO: 34; an LC CDR1 of the amino acid sequence set forth in SEQ ID NO: 37, an LC CDR2 of the amino acid sequence set forth in SEQ ID NO: 38, and an LC CDR3 of the amino acid sequence set forth in SEQ ID NO: 39, or a variant of said antibody comprising 1, 2, 3, 4, 5, or 6 amino acid substitutions in the CDR regions. In one non-limiting embodiment, an anti-TMPRSS6 antibody disclosed herein is the antibody identified herein as humanized anti-TMPRSS6 antibody variant hzMWTx-001Var, comprising an HC polypeptide having the amino acid sequence set forth in SEQ ID NO: 73 and an LC polypeptide having the amino acid sequence set forth in SEQ ID NO: 75.

In one embodiment, an anti-TMPRSS6 antibody disclosed herein comprises an HC variable region polypeptide of the amino acid sequence set forth in SEQ ID NO: 41 or a sequence substantially identical to SEQ ID NO: 41, and an LC variable region polypeptide of the amino acid sequence set forth in SEQ ID NO: 46 or a sequence substantially identical to SEQ ID NO: 46. In one embodiment, an anti-TMPRSS6 antibody disclosed herein comprises an HC CDR1 of the amino acid sequence set forth in SEQ ID NO: 42, an HC CDR2 of the amino acid sequence set forth in SEQ ID NO: 43, an HC CDR3 of the amino acid sequence set forth in SEQ ID NO: 44; an LC CDR1 of the amino acid sequence set forth in SEQ ID NO: 47, an LC CDR2 of the amino acid sequence set forth in SEQ ID NO: 48, and an LC CDR3 of the amino acid sequence set forth in SEQ ID NO: 49, or a variant of said antibody comprising 1, 2, 3, 4, 5, or 6 amino acid substitutions in the CDR regions. In one non-limiting embodiment, an anti-TMPRSS6 antibody disclosed herein is the antibody identified herein as humanized anti-TMPRSS6 antibody variant hzMWTx-002Var, comprising an HC polypeptide having the amino acid sequence set forth in SEQ ID NO: 77 and an LC polypeptide having the amino acid sequence set forth in SEQ ID NO: 79.

In one embodiment, an anti-TMPRSS6 antibody disclosed herein comprises an HC variable region polypeptide of the amino acid sequence set forth in SEQ ID NO: 51 or a sequence substantially identical to SEQ ID NO: 51, and an LC variable region polypeptide of the amino acid sequence set forth in SEQ ID NO: 56 or a sequence substantially identical to SEQ ID NO: 56. In one embodiment, an anti-TMPRSS6 antibody disclosed herein comprises an HC CDR1 of the amino acid sequence set forth in SEQ ID NO: 52, an HC CDR2 of the amino acid sequence set forth in SEQ ID NO: 53, an HC CDR3 of the amino acid sequence set forth in SEQ ID NO: 54; an LC CDR1 of the amino acid sequence set forth in SEQ ID NO: 57, an LC CDR2 of the amino acid sequence set forth in SEQ ID NO: 58, and an LC CDR3 of the amino acid sequence set forth in SEQ ID NO: 59, or a variant of said antibody comprising 1, 2, 3, 4, 5, or 6 amino acid substitutions in the CDR regions. In one non-limiting embodiment, an anti-TMPRSS6 antibody disclosed herein is the antibody identified herein as humanized anti-TMPRSS6 antibody variant hzMWTx-003Var, comprising an HC polypeptide having the amino acid sequence set forth in SEQ ID NO: 81 and an LC polypeptide having the amino acid sequence set forth in SEQ ID NO: 83.

In another aspect, anti-TMPRSS6 antibodies (including variants and fragments as disclosed herein) are provided that can be used to treat disorders of iron metabolism such as iron overload disorders, in particular β-thalassemia and other disorders of ineffective erythropoiesis. Methods and compositions are provided for using anti-TMPRSS6 antibodies as disclosed herein for therapeutic uses including, but not limited to, treating disorders of iron metabolism such as iron overload disorders, in particular β-thalassemia and other disorders of ineffective erythropoiesis. In certain embodiments, pharmaceutical compositions comprising an anti-TMPRSS6 antibody disclosed herein and a suitable carrier and/or excipient are provided.

In another aspect, methods for treating a disorder of iron metabolism are provided, such methods comprising administering an effective amount of an anti-TMPRSS6 antibody disclosed herein to a subject in need thereof, wherein administration of the effective amount of anti-TMPRSS6 antibody modulates the activity of a component involved in iron metabolism. In certain embodiments, methods for treating an iron overload disorder comprise administering an effective amount of an anti-TMPRSS6 antibody disclosed herein, wherein administration of the effective amount of anti-TMPRSS6 antibody modulates the activity of a component involved in iron metabolism. In certain embodiments, methods for treating an iron overload disorder comprise administering an effective amount of an anti-TMPRSS6 antibody disclosed herein, wherein administration of the effective amount of anti-TMPRSS6 antibody modulates the activity of at least one component involved in regulating hepcidin expression. In certain embodiments, methods comprise administration of an effective amount of anti-TMPRSS6 antibody that inhibits TMPRSS6 suppression of hepcidin expression. In certain embodiments, administration of the effective amount of anti-TMPRSS6 antibody increases hepcidin expression. In certain embodiments, methods comprise administration of an effective amount of anti-TMPRSS6 antibody that increases the activity of the hepcidin promoter. In certain embodiments, methods comprise administration of an effective amount of anti-TMPRSS6 antibody that inhibits TMPRSS6 suppression of the BMP/SMAD pathway-induced expression of hepcidin. In certain embodiments, methods comprise administration of an effective amount of anti-TMPRSS6 antibody to a subject that results in one or more biological effects associated with an iron overload disorder including but not limited to reducing serum iron, reducing liver non-heme iron, increasing serum hepcidin, increasing liver hepcidin RNA, reducing splenomegaly, increasing red blood count (RBC), increasing hematocrit (HCT), reducing red cell distribution width (RDW), and/or increased production of mature red cells (increased erythropoiesis).

In another aspect, methods for treating a disease or disease state in which abnormal suppression of hepcidin expression is involved are provided, such methods comprising administering an effective amount of an anti-TMPRSS6 antibody disclosed herein to a subject in need thereof, wherein administration of the effective amount of anti-TMPRSS6 antibody modulates the activity of at least one component involved in abnormal suppression of hepcidin expression and reduces abnormal suppression of hepcidin expression. In particular embodiments, the method results in increased hepcidin expression.

In another aspect, methods for treating a disorder of iron metabolism associated with suppressed hepcidin levels are provided, such methods comprising administering an effective amount of an anti-TMPRSS6 antibody disclosed herein to a subject in need thereof, wherein administration of the effective amount of anti-TMPRSS6 antibody modulates the activity of at least one component involved in suppression of hepcidin levels. In certain embodiments, methods comprise administration of an effective amount of anti-TMPRSS6 antibody that increases serum hepcidin levels, increases liver hepcidin RNA, and lowers serum iron levels.

In another aspect, methods are provided for treating disorders of iron metabolism including disorders related to and/or characterized by ineffective erythropoiesis that may include but are not limited to β-thalassemia. In accordance with this aspect, such methods comprise administering an effective amount of an anti-TMPRSS6 antibody disclosed herein to a subject that is known or suspected of having a disorder of iron metabolism related to and/or characterized by ineffective erythropoiesis, wherein administration results in one or more changes related to iron metabolism and/or erythropoiesis in the subject. In certain embodiments, methods are provided wherein administration of the effective amount of anti-TMPRSS6 antibody treats or ameliorates at least one biological effect or symptom associated with the disorder. In particular embodiments, practicing the method results in one or more changes including but not limited to reducing liver non-heme iron, increasing serum hepcidin, increasing liver hepcidin RNA, reducing splenomegaly, increasing red blood count (RBC), increasing hematocrit (HCT), reducing red cell distribution width (RDW), and increased production of mature red cells (increased erythropoiesis).

In another aspect, methods for diagnosing or screening for an iron overload disorder in a subject are provided. In certain embodiments, methods comprise administering anti-TMPRSS6 antibody to a subject known or suspected to have an iron overload disorder and measuring one or more biological effect or symptom associated with an iron overload disorder.

In another aspect, one or more isolated nucleic acid molecules are provided that encode at least a portion of at least one of the anti-TMPRSS6 antibodies disclosed herein. In certain embodiments, isolated nucleic acid molecules that encode at least a portion of at least one of the anti-TMPRSS6 antibodies disclosed herein comprise a nucleotide sequence as set forth in Table 1, Table 2, or Table 3, or a sequence substantially identical (e.g., at least 85%, 90%, 92%, 95%, 97%, or 98%, 99% identical) to a nucleotide sequence as set forth in Table 1, Table 2, or Table 3. In certain embodiments, isolated nucleic acid molecules that encode at least one of the heavy chain (HC) sequences of the anti-TMPRSS6 antibodies disclosed herein may comprise a nucleotide sequence selected from at least one of: SEQ ID NO: 5 or a sequence substantially identical to SEQ ID NO: 5; SEQ ID NO: 15 or a sequence substantially identical to SEQ ID NO: 15; SEQ ID NO. 25 or a sequence substantially identical to SEQ ID NO: 25; SEQ ID NO: 35 or a sequence substantially identical to SEQ ID NO: 35; SEQ ID NO: 45 or a sequence substantially identical to SEQ ID NO: 45; SEQ ID NO: 55 or a sequence substantially identical to SEQ ID NO: 55; SEQ ID NO: 62 or a sequence substantially identical to SEQ ID NO: 62; SEQ ID NO: 66 or a sequence substantially identical to SEQ ID NO: 66; SEQ ID NO: 70 or a sequence substantially identical to SEQ ID NO: 70; SEQ ID NO: 74 or a sequence substantially identical to SEQ ID NO: 74; SEQ ID NO: 78 or a sequence substantially identical to SEQ ID NO: 78, or SEQ ID NO: 82 or a sequence substantially identical to SEQ ID NO: 82. In certain embodiments, isolated nucleic acid molecules that encode at least one of the light chain (LC) sequences of the anti-TMPRSS6 antibodies or antigen-binding fragments thereof disclosed herein may comprise a nucleotide sequence selected from at least one of: SEQ ID NO: 10 or a sequence substantially identical to SEQ ID NO: 10; SEQ ID NO: 20 or a sequence substantially identical to SEQ ID NO: 20; or SEQ ID NO: 30 or a sequence substantially identical to SEQ ID NO: 30; SEQ ID NO: 40 or a sequence substantially identical to SEQ ID NO: 40; SEQ ID NO: 50 or a sequence substantially identical to SEQ ID NO: 50; SEQ ID NO: 60 or a sequence substantially identical to SEQ ID NO: 60; SEQ ID NO: 64 or a sequence substantially identical to SEQ ID NO: 64; SEQ ID NO: 68 or a sequence substantially identical to SEQ ID NO: 68; SEQ ID NO: 72 or a sequence substantially identical to SEQ ID NO: 72; SEQ ID NO: 76 or a sequence substantially identical to SEQ ID NO: 76; SEQ ID NO: 80 or a sequence substantially identical to SEQ ID NO: 80, or SEQ ID NO: 84 or a sequence substantially identical to SEQ ID NO: 84.

In another aspect, vector is provided comprising one or more nucleic acid molecules that encode at least one amino acid sequence of the anti-TMPRSS6 antibodies disclosed herein. In certain embodiments, a vector is provided comprising one or more nucleic acid molecules that encode at least one of the heavy chain (HC) or light chain (LC) sequences of the anti-TMPRSS6 antibodies disclosed herein. In certain embodiments, a vector is provided comprising nucleic acid molecules that encode at least a portion of at least one of the amino acid sequences as set forth in Table 1, Table 2, or Table 3, or at least a portion of an amino acid sequence substantially identical to an amino acid sequence as set forth in Table 1, Table 2, or Table 3. In certain embodiments, a vector is provided comprising nucleic acid molecules that encode at least a portion of at least one of the HC or LC sequences as set forth in Table 1, Table 2, or Table 3, or at least a portion of an amino acid sequence substantially identical to at least one of the HC or LC sequences as set forth in Table 1, Table 2, or Table 3.

In another aspect, at least one host cell is provided containing a vector comprising one or more nucleic acid molecules that encode amino acid sequences of the anti-TMPRSS6 antibodies disclosed herein. In certain embodiments, a host cell is provided containing a vector comprising nucleic acid molecules that encode at least a portion of at least one of the HC or LC sequences as set forth in Table 1, Table 2, or Table 3, or at least a portion of an amino acid sequence substantially identical to at least one of the HC or LC sequences as set forth in Table 1, Table 2, or Table 3. In certain embodiments, at least one host cell is capable of supporting vector expression and recombinant production of anti-TMPRSS6 antibodies or antigen-binding fragments thereof encoded by the vector. In certain embodiments, at least one host cell is capable of supporting vector expression and recombinant production of anti-TMPRSS6 antibodies or antigen-binding fragments thereof encoded by a vector comprising nucleic acid molecules that encode at least a portion of at least one of the HC or LC sequences as set forth in Table 1, Table 2, or Table 3, or at least a portion of an amino acid sequence substantially identical to at least one of the HC or LC sequences as set forth in Table 1, Table 2, or Table 3. In certain embodiments, host cells are transiently transfected with a vector comprising one or more nucleic acid molecules that encode amino acid sequences of the anti-TMPRSS6 antibodies or antigen-binding fragments thereof disclosed herein, wherein the host cells are capable of supporting vector expression and recombinant production of anti-TMPRSS6 antibodies or antigen-binding fragments thereof encoded by the vector.

BRIEF DESCRIPTION OF THE FIGURES

FIG. 1 shows results from cascade screening of anti-TMPRSS6 antibodies, where antibodies that bind to human TMPRSS6 were assessed using an in vitro functional assay for HAMP promoter activity, and antibodies that showed effects on HAMP promoter activity were assessed for cross-reactivity with non-human TMPRSS6.

FIG. 2A shows effects of the MWTx-001 anti-TMPRSS6 antibody on HAMP promoter activity over a range of antibody concentrations. FIG. 2B shows effects of the MWTx-002 anti-TMPRSS6 antibody on HAMP promoter activity over a range of antibody concentrations. FIG. 2C shows effects of the MWTx-003 anti-TMPRSS6 antibody on HAMP promoter activity over a range of antibody concentrations. FIG. 2D shows effects of the hzMWTx-001Var anti-TMPRSS6 antibody on HAMP promoter activity over a range of antibody concentrations. FIG. 2E shows effects of the hzMWTx-002Var anti-TMPRSS6 antibody on HAMP promoter activity over a range of antibody concentrations. FIG. 2F shows effects of the HzMWTx-003Var anti-TMPRSS6 antibody on HAMP promoter activity over a range of antibody concentrations.

FIGS. 3A-3M show results of determinations of binding affinity of anti-TMPRSS6 antibodies. FIGS. 3A-3F show results of determinations of anti-TMPRSS6 antibody binding affinity for human TMPRSS6 expressed on HEK293T cells using two different methods. In each plot, open circles represent results using an anti-TMPRSS6 antibody over a range of concentrations, and open squares represents results using the same concentration of mouse IgG as a negative control. FIGS. 3A-3C show results using cell surface ELISA (measuring HRP-labelled secondary antibody) to measure binding of MWTx-001 (FIG. 3A), MWTx-002 (FIG. 3B), and MWTx-003 (FIG. 3C) to human TMPRSS6, with calculated $EC_{50}$ values for each antibody used as an estimate of binding affinity. FIGS. 3D-3F show results using FACS (measuring APC-conjugated secondary antibody) to measure binding of MWTx-001 (FIG. 3D), MWTx-002 (FIG. 3E), and MWTx-003 (FIG. 3F) to human TMPRSS6, with calculated $EC_{50}$ values for each antibody used as an estimate of binding affinity. FIGS. 3G-3M show results of determinations of anti-TMPRSS6 antibody affinity and binding kinetics for human ecto-TMPRSS6-FLAG using the Octet® RED96e with analyte concentrations of 50 nM, 25 nM, 12.5 nM, 6.25 nM, 3.13 nM, 1.56 nM and 0.78 nM. FIG. 3G shows binding kinetics of MWTx-001 anti-TMPRSS6 antibody towards ecto-TMPRSS6-FLAG. FIG. 3H shows binding kinetics of MWTx-002 anti-TMPRSS6 antibody towards ecto-TMPRSS6-FLAG. FIG. 3I shows binding kinetics of MWTx-003 anti-TMPRSS6 antibody towards ecto-TMPRSS6-FLAG. FIG. 3J shows binding kinetics of hzMWTx-001Var anti-TMPRSS6 antibody towards ecto-TMPRSS6-FLAG. FIG. 3K shows binding kinetics of hzMWTx-002Var anti-TMPRSS6 antibody towards ecto-TMPRSS6-FLAG. FIG. 3L shows binding kinetics of hzMWTx-003Var anti-TMPRSS6 antibody towards ecto-TMPRSS6-FLAG. FIG. 3M summaries affinity measurements of all anti-TMPRSS6 antibodies.

FIGS. 4A-4U show results of determinations of cross-reactivity of anti-TMPRSS6 antibodies. FIGS. 4A-4I show results of determinations of the cross-reactivity of anti-TMPRSS6 antibodies MWTx-001, MWTx-002, and MWTx-003 to human TMPRSS6 and non-human TMPRSS6 expressed on HEK293T cells. Each histogram plot shows FACS results for a single antibody incubated with HEK293T cells expressing a TMPRSS6 target (thinner line and lighter fill; indicated with antibody name) and the same antibody incubated with control HEK293T cells that do not express a TMPRSS6 protein (thicker line, darker fill; indicated with Ctrl). FIGS. 4A-4C show results using HEK293T cells stably expressing human TMPRSS6 (HuTMPRSS6-(His)$_6$) with MWTx-001 (FIG. 4A), MWTx-002 (FIG. 4B), and MWTx-003 (FIG. 4C). FIGS. 4D-4F show results using HEK293T cells stably expressing mouse TMPRSS6 (MoTMPRSS6-(His)$_6$) with MWTx-001 (FIG. 4D), MWTx-002 (FIG. 4E), and MWTx-003 (FIG. 4F). FIGS. 4G-4I show results using HEK293T cells transiently expressing cynomolgus monkey TMPRSS6 (CynoTMPRSS6-(His)$_6$) with MWTx-001 (FIG. 4G), MWTx-002 (FIG. 4H), and MWTx-003 (FIG. 4I). FIGS. 4J-4U show results of cross-reactivity of anti-TMPRSS6 antibodies to non-human (mouse (FIGS. 4J, 4L, 4N, 4P, 4R, 4T) or cynomolgus monkey (FIGS. 4K, 4M, 4O, 4Q, 4S, 4U)) TMPRSS6 expressed on HEK293T cells using cell surface ELISA (measuring HRP-labelled secondary antibody) to measure binding of MWTx-001 anti-TMPRSS6 antibody (FIGS. 4J-4K), MWTx-002 anti-TMPRSS6 antibody (FIGS. 4L-4M), MWTx-003 anti-TMPRSS6 antibody (FIGS. 4N-4O), hzMWTx-001Var anti-TMPRSS6 antibody (FIGS. 4P-4Q), hzMWTx-002Var anti-TMPRSS6 antibody (FIGS. 4R-4S) and hzMWTx-003Var anti-TMPRSS6 antibody (FIG. 4T-4U) to non-human TMPRSS6. In each plot, open circles represent results using an anti-TMPRSS6 antibody, and open squares represents results of mouse IgG or human IgG1 as a negative (nonspecific binding) control, with calculated $EC_{50}$ values for each antibody used as an estimate of binding affinity.

FIGS. 5A-5R. show results of FACS analysis of binding of anti-TMPRSS6 monoclonal antibodies MWTx-001 (FIGS. 5A-5C), MWTx-002 (FIGS. 5D-5F), MWTx-003 (FIGS. 5G-5I) anti-TMPRSS6 antibodies and their humanized variants hzMWTx-001Var (FIGS. 5J-5L), hzMWTx-002Var (FIGS. 5M-5O), hzMWTx-003Var (FIGS. 5P-5R) anti-TMPRSS6 antibodies to HEK293T cells expressing homologous matriptases. HEK293T cells stably expressing human TMPRSS6 (matriptase-2) (FIGS. 5A, 5D, 5G, 5J, 5M, 5P) were used as a positive control, and HEK293T cells over-expressing matriptase (ST14) (FIGS. 5B, 5E, 5H, 5K, 5N, 5Q) and/or matriptase-3 (TMPRSS7) (FIGS. 5C, 5F, 5I, 5L, 5O, 5R) proteins were used to test binding to homologous matriptases. In each panel (FIGS. 5A-5R) HEK293T cells not expressing matriptase (HEK293T) were used as a negative control, with control (Ctrl) results clearly indicated.

FIGS. 6A-6L show anti-TMPRSS6 antibody treatment increases hepcidin expression in mouse in a dose-dependent manner. FIGS. 6A-6C show effects of MWTx-003 anti-TMPRSS6 antibody (FIGS. 6A-6B) or its humanized variant hzMWTx-003Var anti-TMPRSS6 antibody (FIG. 6C) on serum iron. FIG. 6D shows effect of GFP-TMPRSS6 on serum hepcidin. FIGS. 6D-6F show effects of MWTx-003 anti-TMPRSS6 antibody (FIGS. 6D-6E) or its humanized variant hzMWTx-003Var anti-TMPRSS6 antibody (FIG. 6F) on serum hepcidin. FIG. 6G shows effect of GFP-TMPRSS6 on liver hepcidin RNA. FIGS. 6O-6I show effects of MWTx-003 anti-TMPRSS6 antibody (FIGS. 6G-6H) or its humanized variant hzMWTx-003Var anti-TMPRSS6 antibody (FIG. 6I) on liver hepcidin RNA. FIGS. 6J-6L show serum concentrations of MWTx-003 anti-TMPRSS6 antibody (FIGS. 6J-6K) or its humanized variant hzMWTx-003Var anti-TMPRSS6 antibody (FIG. 6L). Mouse IgG2b (MoIG2b) (FIGS. 6A-6B, 6D-6E, 6G-6H, 6J-6K) or human IgG1 (HuIgg1) (FIGS. 6C, 6F, 6I, 6L) was used as an isotype control, PBS was used as a vehicle control, and GFP vector was used as a vector control (FIGS. 6A, 6D, 6G, 6J).

FIGS. 7A-7D show effects of MWTx-003 anti-TMPRSS6 antibody on RBC (FIG. 7A), HGB (FIG. 7B), HCT (FIG. 7C) and RDW (FIG. 7D) using Th3/+ mice. FIGS. 7L-7M show effect of MWTx-003 anti-TMPRSS6 antibody on erythropoiesis using bone marrow from Th3/+ mice. FIGS. 7O-7P show effect of MWTx-003 anti-TMPRSS6 antibody on erythropoiesis using splenocytes from Th3/+ mice. Representative plots in FIGS. 7K-7P show with four distinct cell clusters (I: basophilic erythroblasts; II: polychromatic erythroblasts; III: orthochromatic erythroblasts and nonnucleated reticulocytes and IV: mature red cells) and their corresponding percentages of cell numbers are highlighted. Wildtype mice were used as a positive control (FIGS. 7A-7J, 7K, 7N), and mouse IgG2b (MoIgG2b) was used as isotype control in the treatment (FIGS. 7A-7J, 7L, 7O). Bar graphs in FIGS. 7Q-7R show average results for cell clusters I, II, III, and IV in bone marrow (FIG. 7Q) and spleen (FIG. 7R) for each treatment regime (WT, Th3/+ w/MoIgG2b, Th3/+ w/MWTx-003) after 4 weeks, where comparisons allow identification of shifts in each population, most notably a shift to mature red blood cells (cluster IV) after MWTx-003 treatment.

FIGS. 8A-8D show results of epitope binning of MWTx-001, MWTx-002 and MWTx-003 anti-TMPRSS6 antibodies for human ecto-TMPRSS6-FLAG using the Octet® RED96e. FIG. 8A shows epitope binning of MWTx-001 anti-TMPRSS6 antibody towards ecto-TMPRSS6-FLAG. FIG. 8B shows epitope binning of MWTx-002 anti-TMPRSS6 antibody towards ecto-TMPRSS6-FLAG. FIG. 8C shows epitope binning of MWTx-003 anti-TMPRSS6 antibody towards ecto-TMPRSS6-FLAG. FIG. 8D summarizes association signals for MWTx-001, MWTx-002 and MWTx-003 anti-TMPRSS6 antibodies.

DETAILED DESCRIPTION

Figure 2A:
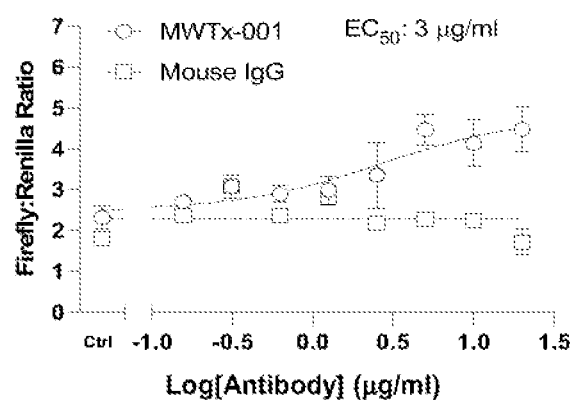
FIGS. 2A-2F show effects of anti-TMPRSS6 antibodies on HAMP promoter activity measured by a dual luciferase reporter assay carried out in HepG2 cells, for a range of antibody concentrations. In each plot, open circles represent results using an anti-TMPRSS6 antibody, and open squares represents results using the same concentration of mouse IgG or human IgG1 as a negative (nonspecific binding) control.

The invention relates to novel antibodies and antigen-binding fragments thereof that bind TMPRSS6, and methods of making and using the same.

Terminology/Definitions

Scientific and technical terms used in connection with the present invention shall have the meanings that are commonly understood by those of ordinary skill in the art, unless otherwise defined. Use of singular terms ("a" or "an" or "the" or other use of a term in the singular) include plural reference, and plural terms shall include the singular, unless the context clearly dictates otherwise. Thus, for example, reference to "an antibody" includes "one or more" antibodies or a "plurality" of such antibodies. All publications mentioned herein are hereby incorporated by reference in their entirety.

Generally, nomenclature and techniques of molecular biology, microbiology, cell and tissue culture, protein and nucleotide chemistry, and recombinant DNA techniques available to one of skill of the art can be employed for the antibodies, antigen-binding fragments, compositions, and methods disclosed herein. Techniques and procedures described herein are generally performed according to conventional methods well known in the art and as described in various general and more specific references, inter alia, Sambrook et al. (1989) MOLECULAR CLONING: A LABORATORY MANUAL (2nd ed., Cold Spring Harbor Laboratory Press. Cold Spring Harbor, N.Y.) and Ausubel et al. (1994) CURRENT PROTOCOLS IN MOLECULAR BIOLOGY, Volumes I-III (John Wiley & Sons, N.Y.). Enzymatic reactions and purification techniques are performed according to manufacturer's specifications or as commonly accomplished in the art or as described herein, unless otherwise specified herein. Techniques and methods for pharmaceutical preparation and formulation, and treatment of subjects, are described herein using conventional nomenclature.

"Antibody" refers in the broadest sense to a polypeptide or combination of polypeptides that recognizes and binds to an antigen through one or more immunoglobulin variable regions, where the immunoglobulin variable regions may be naturally occurring or non-naturally occurring, e.g., as a result of engineering, chimerization, humanization, optimization, CDR-grafting, or affinity maturation.

An "antibody" as disclosed herein can be a whole (intact, full length) antibody, a single chain antibody, or an antigen binding fragment with one or two chains, and can be naturally occurring and non-naturally occurring. An antibody comprises at least sufficient complementarity determining regions (CDR), interspersed with framework regions (FR), for the antibody to recognize and bind to an antigen. An anti-TMPRSS6 antibody disclosed herein may be, but is not limited to, at least one of a monoclonal antibody, a polyclonal antibody, a humanized antibody, a chimeric antibody, a single chain antibody, a Fab fragment, a single-chain variable fragment (scFv), an aptamer, a single-domain antibody (VHH or nanobody), a recombinant antibody, a modified antibody having peptide/other moieties attached to antibody and/or additional amino acids added the N- or C-terminus, or other TMPRSS6-binding fragment or variant. Whole antibody, full length antibody, intact antibody, naturally occurring antibody, or equivalent terms are understood to refer to a polypeptide, in particular a glycoprotein, comprising at least two heavy chains (HCs) and two light chains (LCs) interconnected by disulfide bonds. Each HC is comprised of a heavy chain variable region (VH) and an HC constant region (CH), and each light chain is comprised of a light chain variable region (VL) and an LC constant region (CL). The HC and LC variable regions, VH and VL, include a binding domain that interacts with an antigen. The VH and VL regions can be further subdivided into CDR regions characterized by hypervariability, interspersed with FR regions that are typically more conserved. Each VH and VL is typically composed of three CDRs and four FRs arranged from amino-terminus to carboxy-terminus in the following order: FR1, CDR1, FR2, CDR2, FR3, CDR3, FR4. The constant regions of the antibodies may mediate the binding of the immunoglobulin to host tissues or factors, including various cells of the immune system and the classical complement system. Typically, an antibody comprises at least heavy chain (HC) CDR1, CDR2, and CDR3 and light chain (LC) CDR1, CDR2, and CDR3 sequences, where any one of these sequences may be naturally or non-naturally occurring. An antibody may comprise fewer CDR sequences, as long as the antibody can recognize and bind an antigen.

An anti-TMPRSS6 antibody disclosed herein may be a variant comprising at least one altered CDR or framework sequence, wherein CDR and/or framework sequences may by optimized by mutating a nucleic acid molecule encoding such framework sequence. Variants may be constructed with HC and LC portions derived independently from different sources. Techniques for generating variants include but are not limited to conservative amino acid substitution, computer modeling, screening candidate polypeptides alone or in combinations, and codon optimization, and it is understood that a skilled person is capable of generating antibody variants as may be needed. An anti-TMPRSS6 antibody disclosed herein may be a fragment. Antigen binding functions of an antibody can be performed by fragments such as: a Fab fragment; a monovalent fragment consisting of the VL, VH, CL and CH1 domains; a F(ab)$_2$ fragment; a bivalent fragment comprising two Fab fragments linked by a disulfide bridge at the hinge region; an Fd fragment consisting of the VH and CH1 domains; a single-chain variable fragment (scFv) consisting of the VL and VH domains of a single arm of an antibody; a single domain antibody (dAb) fragment which consists of a VH domain; and an isolated CDR (VHH, nanobody), or an aptamer. Antigen binding portions can be incorporated into single domain antibodies, maxibodies, minibodies, nanobodies, intrabodies, diabodies, triabodies, tetrabodies, v-NAR and bis-scFv (see, e.g., Hollinger and Hudson, 2005, Nature Biotechnology, 23, 9, 1126-1136). Antigen binding portions of antibodies can be grafted into scaffolds based on polypeptides to form monobodies (see, e.g., U.S. Pat. No. 6,703,199, which describes fibronectin polypeptide monobodies).

The term antibody encompasses various broad classes of polypeptides that can be distinguished biochemically. The "class" of an antibody refers to the type of constant domain or constant region possessed by its heavy chain. Those skilled in the art understand that there are five major classes of antibodies, viz., IgA, IgD, IgE, IgG, and IgM, and several of these may be further divided into subclasses (isotypes), e.g., IgG1, IgG2, IgG3, IgG4, IgA1, and IgA2, each of which is well characterized and known to confer functional specialization. Modified versions of each of these classes and isotypes are readily discernable and within the scope of the instant disclosure. While all immunoglobulin classes are within the scope of the present disclosure, the present disclosure will be directed largely to the IgG class of immunoglobulin molecules.

The term "chimeric" antibody refers to an antibody in which a portion of the heavy chain (HC) and/or light chain (LC) involved in forming the immunoreactive site is derived from a particular source or species, while the remainder of the HC and/or LC is derived from a different source or species. In certain embodiments the target binding region or site will be from a non-human source (e.g., mouse or non-human primate) and the constant region is human.

As used herein, the phrase "humanized antibody" refers to an antibody or antibody variant derived from a non-human antibody, typically a mouse monoclonal antibody, where CDRs from the parental, non-human antibody are grafted (fused) in a framework comprising variable regions derived from a human immunoglobulin framework, in particular an acceptor human framework or a human consensus framework. Techniques and principles for designing, making, and testing humanized antibodies are known (Jones P T, Dear P H, Foote J, Neuberger M S, Winter G. Replacing the complementarity-determining regions in a human antibody with those from a mouse. *Nature*. 1986 May 29-Jun. 4; 321(6069):522-5; Almagro J C, Fransson J. Humanization of antibodies. *Front Biosci*. 2008 Jan. 1; 13:1619-33). It is understood that changes can be made to an acceptor framework at multiple locations in order to develop a humanized antibody having improved features according to the desired use, e.g., high affinity for target, low clearance, low toxicity, etc. An anti-TMPRSS6 antibody disclosed herein may be a humanized variant.

"Affinity" refers to the strength of the sum total of noncovalent interactions between a single binding site of a molecule (e.g., an antibody) and its binding partner (e.g., an antigen). Unless indicated otherwise, binding affinity as used herein refers to intrinsic binding affinity which reflects a 1:1 interaction between members of a binding pair (e.g., antibody and antigen). Affinity can be measured by common methods known in the art, including those described herein. The calculated concentration at which approximately 50% of maximal binding (the calculated $EC_{50}$) can be used as an estimate of affinity. The affinity of a molecule X for its partner Y can generally be represented by the dissociation constant (Kd or KD, representing $k_{off}/k_{on}$ measured for the interaction).

A "subject" is a mammal, where mammals include but are not limited to primates (e.g., humans and non-human primates such as monkeys), domesticated animals (e.g., cows, sheep, cats, dogs, pigs, llamas, and horses), rabbits, and rodents (e.g., mice and rats). In certain embodiments, the subject is a human. The phrases "to a subject in need thereof" or "to a patient in need thereof" or "to a patient in need of treatment" or "a subject in need of treatment" may include subjects that would benefit from administration of the anti-TMPRSS6 antibodies disclosed herein, for treatment of an iron overload disorder. It is understood that administration of anti-TMPRSS6 antibodies encompasses administration to "a subject in need thereof" can be interpreted as referring to a subject known or suspected to have an iron overload disorder, in particular a β-thalassemia, based on indicators such as symptoms, family history, or genotype. It is further understood that anti-TMPRSS6 antibodies can be administered to a subject that is not known or suspected to have a disorder of iron metabolism, for purposes that may include but are not limited to, preventative or prophylactic purposes, for screening, for diagnostics, for research purposes, or to achieve results distinct from treating a disorder.

An "effective amount" of an anti-TMPRSS6 antibody, e.g., in a pharmaceutical formulation, refers to an amount effective, at dosages and for periods of time necessary, to achieve the desired therapeutic or prophylactic result. It is understood that "effective amount" is intended to refer to the amount of an anti-TMPRSS6 antibody or a pharmaceutical composition comprising an anti-TMPRSS6 antibody that will elicit the biological response of, or desired therapeutic effect on, a cell, a tissue, a system, a non-human animal subject, a non-human mammal subject, or a human subject that is being measured. The terms "therapeutically effective amount", "pharmacologically effective amount", and "physiologically effective amount" are used interchangeably to refer to the amount of an anti-TMPRSS6 antibody that is needed to provide a threshold level of active agents in the bloodstream or in the target tissue. The precise amount will depend upon numerous factors, e.g., the particular anti-TMPRSS6 antibody (active agent), the components and physical characteristics of the composition, intended population of subjects/patients to be treated, considerations such as the disease state, age, sex, and weight of a subject, and the like, and can readily be determined by one skilled in the art, based upon the information provided herein or otherwise available in the relevant literature. The terms, "improve", "increase" or "reduce", as used in this context, indicate values or parameters relative to a baseline measurement, such as a measurement in the same subject prior to initiation of the treatment described herein, or a measurement in a control individual (or multiple control individuals) in the absence of the treatment described herein.

The term "pharmaceutical composition" or "pharmaceutical formulation" refers to a preparation which is in such form as to permit the biological activity of an active ingredient contained therein to be effective, in particular an anti-TMPRSS6 antibody. It is understood that a pharmaceutical composition may contain more than one active ingredient, e.g., more than one anti-TMPRSS6 antibody, or a combination of an anti-TMPRSS6 antibody with another active ingredient that acts on a different target, where such combinations can be but are not limited to, a combination of an antiTMPRSS6 antibody with another active ingredient having a desired effect on hematopoietic processes, in particular erythropoiesis, a combination of an anti-TMPRSS6 antibody with gene therapy agents such as agents to carry out gene therapy targeting the HBB gene, or a combination of an anti-TMPRSS6 antibody with Fc-fusion proteins that target TGF superfamily ligands to stimulate erythropoiesis. A "pharmaceutically acceptable carrier" refers to an ingredient in a pharmaceutical formulation, other than an active ingredient, which is nontoxic to a subject. It is understood that a pharmaceutically acceptable carrier can be, but is not limited to, a buffer, excipient, stabilizer, an adjuvant, or preservative.

The term "treat" or "treating" or similar terms as used herein, can refer to an outcome that is deemed beneficial for a particular subject in a defined set of circumstances. Treating a disorder of iron metabolism may refer non-exclusively to any of reducing, ameliorating, slowing, interrupting, arresting, alleviating, stopping, or reversing the progression or severity of an existing symptom, disorder, condition, or disease, and may further encompass prevention or delay of the onset of one or more symptoms of an iron overload disorder, and/or lessening of the severity or frequency of one or more symptoms of an iron overload disorder. The terms "treating" or "method of treating" or equivalents can encompass one or more uses of anti-TMPRSS6 antibodies disclosed herein, including but not limited to therapeutic, prophylactic, preventive, diagnostic, imaging, and screening uses.

The term "vector," as used herein, refers to a nucleic acid molecule capable of propagating a nucleic acid to which the vector sequence is linked, in a host cell in which the vector is introduced. Vectors capable of directing the expression of nucleic acids to which they are operatively linked are referred to herein as "expression vectors."

Anti-TMPRSS6 Antibodies

Antibodies and antigen-binding fragments are provided that are capable of binding TMPRSS6 on the surface of a cell and modulating the activity of at least one component involved in iron metabolism, in particular at least one component involved in iron overload disorders associated with abnormal suppression of hepcidin expression. Anti-TMPRSS6 antibodies that are capable of binding TMPRSS6 on the surface of a cell and modulating the activity of at least one component involved in regulating hepcidin expression can be used in methods for treating iron overload disorders associated with abnormal suppression of hepcidin expression. Anti-TMPRSS6 antibodies that are capable of binding TMPRSS6 on the surface of a cell and modulating TMPRSS6 suppression of hepcidin expression can be used to therapeutically target TMPRSS6 in methods for treating iron overload disorders associated with abnormal suppression of hepcidin expression.

Once antibodies or fragments specific for TMPRSS6, in particular human TMPRSS6 expressed on the surface of a cell, have been obtained, the desired biological activity of modulating the activity of at least one component involved in iron metabolism thereof can be tested by several methods known to the skilled person.

It is understood that "modulate" or "modulating" or similar terms as used herein can refer to one or more effects that can result when an anti-TMPRSS6 antibody disclosed herein binds its target. "Modulating" and its equivalents can refer to different modes of action and effects depending on the component under consideration, i.e., modulating can refer to neutralizing, reversing, inhibiting, blocking, reducing, antagonizing, or otherwise interfering with the activity of certain components involved in iron metabolism, while for other components involved in iron metabolism the term modulating can refer to increasing, enhancing, or having an agonist effect on these components.

It is understood that the term "component" can refer not only to target molecule TMPRSS6, but also to a downstream process or pathway involved in iron metabolism. Thus, a component within the meaning of a process or pathway can be, but is not limited to, regulation of hepcidin expression, TMPRSS6 suppression of hepcidin expression, the process of hepcidin expression, regulation of hepcidin levels, increasing hepcidin levels, the activity of the hepcidin promoter, or TMPRSS6 suppression of the BMP/SMAD pathway-induced expression of hepcidin, regulation of liver non-heme iron levels, one or more processes involved in splenomegaly, or one or more hematopoietic processes involved in regulation of red blood count (RBC), hematocrit (HCT), red cell distribution width (RDW), and erythropoiesis, in particular production of mature red cells.

Anti-TMPRSS6 antibodies as disclosed herein can be used to therapeutically target at least one component involved in iron metabolism, in particular at least one component involved in iron overload disorders. In certain embodiments, anti-TMPRSS6 antibodies as disclosed herein can be used to therapeutically target at least one component involved in regulating hepcidin expression, and modulate the activity of the component to achieve increased hepcidin expression. In certain embodiments, anti-TMPRSS6 antibodies as disclosed herein can be used to modulate the activity of the hepcidin promoter to achieve increased hepcidin expression. It is understood that anti-TMPRSS6 antibodies as disclosed herein can be used to therapeutically target TMPRSS6 and thereby modulate the downstream activity of other components of hepcidin expression, including but not limited to, regulation of liver non-heme iron levels, one or more processes involved in splenomegaly, or one or more hematopoietic processes involved in regulation of red blood count (RBC), hematocrit (HCT), red cell distribution width (RDW), and erythropoiesis, in particular production of mature red cells.

Using anti-TMPRSS6 antibodies as disclosed herein to therapeutically target at least one component involved in iron metabolism, allows precise modulation of the targeted component. It is understood that by using anti-TMPRSS6 antibodies as disclosed herein to precisely target TMPRSS6 and its downstream effects on at least one component involved in regulating hepcidin expression, it is possible to avoid undesirable effects, difficulties with delivery and/or effectiveness, and regulatory hurdles associated with other approaches to treating iron overload disorders that are currently in use or under development, e.g., blood transfusions that can further exacerbate iron overload, iron chelation with poor patient compliance, intrusive phlebotomy or splenectomy that only manage symptoms, gene therapy targeting the HBB gene with potential permanent pleiotropic effects in multiple systems, gene therapy and gene editing with unknown off-target effects, Fc-fusion proteins targeting TGF superfamily ligands to inhibit SMAD signaling that do not reduce the need for iron chelation therapy to manage iron overload, and other approaches that are difficult to control or deliver such as hepcidin mimetics, and antisense or iRNA drugs targeting TMPRSS6. It is understood that using anti-TMPRSS6 antibodies for precise therapeutic targeting does not exclude the possibility of using anti-TMPRSS6 antibodies in methods and compositions for combination treatments. e.g., in combination with another active ingredient that acts on a different target, in combination with an antibody that binds a different target, in combination with gene therapy agents and methods for targeting the HBB gene, or in combination with Fe-fusion proteins that target TGF superfamily ligands to stimulate erythropoiesis.

Anti-TMPRSS6 antibodies disclosed herein allow the development of treatments that can be tailored to each subject (e.g., dosage, frequency of administration), where they can be continued and discontinued with ease, and combined with other therapies. In certain strategic embodiments, anti-TMPRSS6 antibodies disclosed herein can be combined with other therapies that may address multiple therapeutic targets and/or address deficits or undesirable effects of one of the therapies in the combination therapy.

Exemplary Embodiments of Anti-TMPRSS6
Antibodies and Uses Thereof

Non-limiting exemplary embodiments of anti-TMPRSS6 antibodies of the invention are presently disclosed, in particular in the Examples, Tables, and Figures.

Antibodies Capable of Binding TMPRSS6

As demonstrated in the Examples, a functional cascade can be used to identify and characterize anti-TMPRSS6 antibodies of the present invention, where a first step in the cascade involves screening for antibodies capable of binding to human TMPRSS6 on the surface of a cell expressing TMPRSS6 (Example 1, FIG. 1), followed by a second step to identify antibodies capable of binding to human TMPRSS6 on the surface of a cell expressing TMPRSS6 and modulating the activity of a component involved in iron metabolism, in this case testing for the ability to increase hepcidin (HAMP) promoter activity (Example 2). As demonstrated by exemplary embodiments shown in FIG. 1, the first step identified 143 antibodies (clones) capable of binding to human TMPRSS6 on the surface of a cell expressing TMPRSS6, and the second step identified ten (10) of the antibodies (out of 143 screened) as "active" antibodies (clones) that were able to increase hepcidin (HAMP) promoter activity.

In a third step of the functional cascade (FIG. 1), the ten (10) "active" antibodies were tested for cross-reactivity with non-human TMPRSS6 targets from sources that would be relevant for further studies, viz., testing for cross-reactivity with mouse TMPRSS6 relevant to preclinical efficacy studies in a mouse model, and testing for cross-reactivity with cynomolgus monkey TMPRSS6 relevant to toxicity (safety) trials. As demonstrated by exemplary embodiments shown in FIG. 1, demonstrated in Example 4 and illustrated in FIG. 4, three (3) clones (out of 10 screened) showed cross-reactivity with at least one non-human TMPRSS6 and were designated MWTx-001, MWTx-002, and MWTx-003. Each of the monoclonal antibodies was sequenced and CDRs on each HC and LC were identified (Kabat numbering). HC and LC sequences were identified as follows for: MWTx-001 (SEQ ID NOs: 61(HC) and 63(LC)); MWTx-002 (SEQ ID NOs: 65 (HC) and 67 (LC)); and MWTx-003 9SEQ ID NOs: 69(HC) and 71 (LC)). A hybridoma cell line producing the MWTx-001 monoclonal antibody has been deposited with the American Type Culture Collection (ATCC®), 10801 University Boulevard, Manassas, Virginia, 20110, United States of America, on May 27, 2020, under the terms of the Budapest Treaty, under ATCC Accession No. PTA-126759. A hybridoma cell line producing the MWTx-002 monoclonal antibody has been deposited with the American Type Culture Collection (ATCC®), 10801 University Boulevard, Manassas, Virginia, 20110, United States of America, on May 27, 2020, under the terms of the Budapest Treaty, under ATCC Accession No. PTA-126760. A hybridoma cell line producing the MWTx-003 monoclonal antibody has been deposited with the American Type Culture Collection (ATCC®), 10801 University Boulevard, Manassas, Virginia, 20110, United States of America, on May 27, 2020, under the terms of the Budapest Treaty, under ATCC Accession No. PTA-126761.

Humanized Variants

Humanized antibodies comprising CDRs derived from a non-human source grafted into a human-derived antibody framework are expected to be non-immunogenic when administered to a human subject. As demonstrated by exemplary embodiments disclosed in Example 2, humanized anti-TMPRSS6 antibody variants were successfully generated, tested, optimized, and selected. Multiple candidate HC and LC variants were developed wherein each HC or LC variant had the same CDR sequences but the variable region frameworks sequences could vary at over 90% of the framework positions, and these variants tested in different HC/LC combinations to identify combinations having desired features. After initial design and testing, variants that showed desired antigen binding affinity were selected for further evaluation and development, including but not limited to modification of some parental CDR sequences to avoid potential unwanted events such as aspartate isomerization, and modification of some constant regions (Fc) to achieve desired functions such as minimizing antibody-dependent cellular cytotoxicity (ADCC), to arrive at humanized variants hzMWTx-001Var (SEQ ID NOs: 73 (HC) and 75 (LC)), hzMWTx-002Var (SEQ ID NOs: 77(HC) and 79 (LC)), and hzMWTx-003Var (SEQ ID NOs: 81(HC) and 83(LC)).

Anti-TMPRSS6 Antibodies that Increase Hepcidin Promoter Activity

As disclosed herein, antibodies for use in treating iron overload disorders characterized by reduced hepcidin expression may modulate the activity of at least one component involved in hepcidin expression, where the component may be activity of the hepcidin promoter. As demonstrated by exemplary embodiments using an in vitro assay disclosed in Example 2, anti-TMPRSS6 antibodies MWTx-001, MWTx-002, MWTx-003, hzMWTx-001Var, hzMWTx-002Var, and hzMWTx-003Var increased HAMP promoter activity in a dose-dependent manner (FIGS. 2A-2F), while isotype controls at the same concentrations did not increase HAMP promoter activity.

Anti-TMPRSS6 Antibodies Having High Affinity for a Target in a Relevant Biological Context Anti-TMPRSS6 antibodies showed high affinity for a biologically appropriate target, i.e., human TMPRSS6 expressed on the surface of a cell. As demonstrated by exemplary embodiments of affinity measurements using three different methods disclosed in Example 3 and FIG. 3M, monoclonal antibodies MWTx-001, MWTx-002, and MWTx-003, and humanized variants hzMWTx-00Var, hzMWTx-002Var, and hzMWTx-003Var consistently exhibited favorable affinity characteristics for therapeutically effective antibodies or antibody fragments.

Anti-TMPRSS6 Antibodies Having Cross-Reactivity with Non-Human Targets

It is desirable for therapeutically useful antibodies or antibody fragments to have sufficient cross-reactivity with non-human targets (non-human homologues) from sources that would be relevant for further studies such as preclinical efficacy studies, animal models of disease, toxicology studies, etc., such that the antibodies or antibody fragments should recognize, e.g., a mouse homologue and/or a primate homologue such as from cynomolgus monkey. As demonstrated by exemplary embodiments disclosed in Example 4, MWTx-001, hzMWTx-001Var, MWTx-003, and hzMWTx-003Var showed detectable cross-reactivity with mouse TMPRSS6, while MWTx-001, MWTx-002, MWTx-003, hzMWTx-001Var, hzMWTx-002Var, and hzMWTx-003Var showed detectable cross-reactivity with cynomolgus monkey TMPRSS6.

Anti-TMPRSS6 Antibodies Specifically Bind TMPRSS6 (Matriptase-2)

Antibodies with a high level of specific binding to a target protein and low cross-reactivity with homologous proteins in the same organism, are expected to have reduced or no off-target effects. Anti-TMPRSS6 antibodies provided here show high specificity for human TMPRSS6 (matriptase-2), making them suitable for use in targeted compositions and methods. As demonstrated by exemplary embodiments disclosed in Example 5 and illustrated in FIGS. 5A-R, monoclonal antibodies MWTx-001, MWTx-002, and MWTx-003, and their humanized variants hzMWTx-001Var, hzMWTx-002Var, and hzMWTx-003Var show specific binding to human TMPRSS6 (matriptase-2) and did not show detectable cross-reactivity with homologous human matriptases, i.e., these antibodies did not show detectable binding to matriptase-1 (ST14) or matriptase-3 (TMPRSS7).

Anti-TMPRSS6 Antibodies Having In Vivo Dose-Dependent Effects on Hormones and Symptoms Associated with Iron Overload Disorder Antibodies that can increase the level of serum hepcidin, a hormone that controls iron absorption and mobilization from iron stores, are expected to reduce, ameliorate, or prevent symptoms of iron overload disorder, in particular to reduce, ameliorate, or prevent symptoms of elevated levels of serum iron. As demonstrated by exemplary embodiments shown in Example 6, administration of anti-TMPRSS6 monoclonal antibody MWTx-003 or humanized variant hzMWTx-003Var to wildtype subjects, i.e., subject that is not known or suspected to have an iron overload, resulted in an increase in serum hepcidin levels (FIGS. 6A-6C), a decrease in serum iron levels (FIGS. 6D to 6F), and an increase in liver hepcidin RNA levels (FIGS. 6G-6I) compared with isotype controls. These effects were dose-dependent, which can be interpreted as indicating, without wishing to be bound by a mechanism of action, that the dose-dependent in vivo effects of anti-TMPRSS6 antibodies indicate that a skilled person can determine an effective amount (dosage) for a given subject.

Anti-TMPRSS6 Antibodies Having In Vivo Efficacy in a β-Thalassemia Disease Model Antibodies and antibody fragments that can relieve one or more symptoms of an iron overload disorder in vivo when administered to a subject exhibiting an animal model of the disease, i.e., a subject that is known or suspected to have an iron overload disorder, are expected to have therapeutic effectiveness for clinical use. As demonstrated by exemplary embodiments shown in Example 7 using the Th3/+ mouse model of β-thalassemia, administration of the anti-TMPRSS6 monoclonal antibody MWTx-003 resulted in multiple effects including but not limited to reducing liver non-heme iron, increasing serum hepcidin, increasing liver hepcidin RNA, reducing splenomegaly, increasing red blood count (RBC), increasing hematocrit (HCT), reducing red cell distribution width (RDW), and increased production of mature red cells (increased erythropoiesis), compared with isotype controls. Each of these effects can be understood as an amelioration of a symptom of the disorder. Symptoms of the disorder are manifested in multiple biological systems that include but are not limited to effects in the liver (effects on liver non-heme iron, liver hepcidin RNA), in the blood (effects on serum iron levels, circulating hormone levels in particular serum hepcidin levels, RBC, HCT, RDW), spleen size and function (splenomegaly), and erythropoiesis in multiple sites including but not limited to bone marrow and spleen (effects on abundance of different precursor cell types and abundance of mature red cells in erythropoietic sites). Administration of anti-TMPRSS6 antibodies ameliorated multiple symptoms throughout the disease model subject, shifting the measured symptom levels away from levels seen in isotype controls for the disease model (untreated disease) and towards the levels seen in wildtype littermates that represent normal levels in a genetically similar subject that is not known or suspected to have the disease. Without wishing to be bound by a theory or mechanism of action, it is understood that ineffective erythropoiesis is a driving force for abnormal hepcidin suppression leading to increased iron absorption and iron overload, such that a treatment that improves erythroblast differentiation and maturation into red cells should be therapeutically beneficial for treating an iron overload disorder. The present non-limiting exemplary embodiment discloses an anti-TMPRSS6 antibody therapy that increased erythroblast differentiation and maturation into red cells and also decreased iron loading.

Compositions

Compositions are provided that comprise the anti-TMPRSS6 antibody of the present invention with safe and effective amounts and pharmaceutically acceptable carrier(s) or excipient(s) suitable for the intended use(s) of each composition. Such carriers include but are not limited to: saline, buffer, glucose, water, glycerol, ethanol, excipient, stabilizer, preservative, or combinations thereof. It is understood that the pharmaceutical preparation should match the administration mode.

Anti-TMPRSS6 antibodies disclosed herein can be administered by any suitable means, including but not limited to injection or parenteral infusion. Parenteral infusion can include intramuscular, intravenous, intraarterial, intraperitoneal, subcutaneous administration, or parenteral delivery to the liver. Anti-TMPRSS6 antibodies disclosed herein can be formulated for introduction into hepatic tissue or vasculature for delivery localized to target tissues. Anti-TMPRSS6 antibodies disclosed herein can be administered using a device, or as a depot, or in a sustained-release preparations (e.g., semipermeable matrices of solid hydrophobic polymers containing the antibody, or microcapsules) to allow slow and/or measured and/or localized delivery. Anti-TMPRSS6 antibodies disclosed herein can be formulated and administered using colloidal drug delivery systems (for example, liposomes, albumin microspheres, microemulsions, nano-particles and nanocapsules) or in macroemulsions.

Methods

Methods are provided for treating a disorder of iron metabolism using an effective amount of an anti-TMPRSS6 antibody disclosed herein. Without wishing to be bound by a particular mechanism of action, methods provided for targeting TMPRSS6 using anti-TMPRSS6 antibodies disclosed herein result in multiple downstream effects, in particular effects on components (molecules, systems, processes) involved in iron metabolism and erythropoiesis. Without wishing to be bound by a particular mechanism of action, methods are provided for treating a disorder of iron metabolism using an effective amount of an anti-TMPRSS6 antibody disclosed herein to modulate the activity of a component involved in iron metabolism. In particular, methods are provided for treating iron overload disorders associated with excess iron accumulation in tissues and organs, including disorders related to or characterized by ineffective erythropoiesis that may include but are not limited to β-thalassemia, in particular non-transfusion dependent thalassemia, MDS (myelodysplastic syndrome), dyserythropoietic anemia, and sideroblastic anemia. Without being limited to a single mechanism of action, methods are provided for treating an iron overload disorders associated with low hepcidin levels, in particular disorders associated with suppressed hepcidin expression, including a disease or state in which abnormal suppression of hepcidin expression is involved, by administering anti-TMPRSS6 antibodies capable of increasing hepcidin expression.

Methods for treating a disorder of iron metabolism as provided herein comprise administering an effective amount of an anti-TMPRSS6 antibody disclosed herein to a subject in need thereof, wherein administration of the effective amount of anti-TMPRSS6 antibody ameliorates at least one biological effect (symptom) associated with the disorder. Methods for treating a disorder of iron metabolism associated with suppressed hepcidin levels are provided wherein administration of an effective amount of an anti-TMPRSS6 antibody disclosed herein to a subject in need thereof, results in at least one of increased hepcidin promoter activity, increased hepcidin transcription, increased hepcidin RNA levels, and increased hepcidin levels, in particular serum hepcidin levels. Methods for treating a subject known or suspected to have an iron overload disorder are provided wherein administration of an effective amount of anti-TMPRSS6 antibody results in one or more biological effects including but not limited to reducing liver non-heme iron, increasing serum hepcidin, increasing liver hepcidin RNA, reducing splenomegaly, increasing red blood count (RBC), increasing hematocrit (HCT), reducing red cell distribution width (RDW), and increased production of mature red cells (increased erythropoiesis). Methods for treating a subject known or suspected to have an iron overload disorder characterized by ineffective erythropoiesis are provided wherein administration of an effective amount of anti-TMPRSS6 antibody results in one or more biological effects including but not limited to reducing liver non-heme iron, increasing serum hepcidin, increasing liver hepcidin RNA, reducing splenomegaly, increasing red blood count (RBC), increasing hematocrit (HCT), reducing red cell distribution width (RDW), and increased production of mature red cells (increased erythropoiesis).

Methods and compositions are provided for treating a disorder of iron metabolism, in particular an iron overload disorder, even more particularly an iron overload disorder characterized by ineffective erythropoiesis, wherein administration of an effective amount of an anti-TMPRSS6 antibody results in treating or ameliorating more than one biological effect or symptom associated with the disorder. Without wishing to be bound by a theory or mechanism of action, it is understood that ineffective erythropoiesis characterized by erythroid precursor apoptosis resulting in few mature red cells produced in the bone marrow, is a driving force for abnormal hepcidin suppression leading to increased iron absorption and iron overload. In accordance with this understanding, a treatment that improves erythroblast differentiation and maturation into red cells should be therapeutically beneficial for treating an iron overload disorder. The effectiveness of anti-TMPRSS6 antibody therapy to increase erythroblast differentiation and maturation into red cells, decrease iron loading, increase hepcidin expression, etc., maximizes the therapeutic benefit of the methods and compositions using anti-TMPRSS6 antibodies disclosed herein.

The following examples are offered to illustrate, but not to limit, the claimed invention.

EXAMPLES

Example 1: Antibody Production and Identification of Antibodies that Bind TMPRSS6

The production of novel monoclonal antibodies against TMPRSS6 was carried out under contract by the LakePharma Discovery Immunology group (LakePharma, Inc. San Carlos, CA), utilizing in vivo rodent immunization and hybridoma technology. DNA-based immunization via hydrodynamic gene transfer tail vein injection was performed in B6:SJL mice (The Jackson Laboratories) using a mixture of pLEV113_huTMPRSS6 and pLEV113_moTMPRSS6-TCE plasmid DNA (cloned at LakePharma, Inc). Sufficient plasma titers as determined by fluorescence-activated cell sorting (FACS) were obtained, triggering downstream antibody recovery and screening activities. Electrofusion using a NEPA GENE ECFG21 Super Electro Cell Fusion Generator (Nepa Gene Co., Ltd., Ichikawa-City, Chiba, Japan) was performed with pooled splenocytes from 2 immunized mice and a myeloma fusion partner. Fusion material was plated in a total of ten (10) 384-well plates in hypoxanthine-aminopterin-thymidine medium, which specifically selects for hybridomas over unfused myeloma partner cells. Hybridoma supernatants were initially screened for HuTMPRSS6 reactivity by FACS measurement to detect supernatants that gave a positive staining signal on TMPRSS6-expressing HEK293T cells (a plasmid encoding huTMPRSS6-(His)$_6$ (SEQ ID NO: 97) was transfected in HEK293T cells, TMPRSS6-expressing HEK293T cells were selected) and negative staining on parentals (HEK293T) on day 10 post-fusion. Hybridoma supernatants giving a positive staining signal on TMPRSS6-expressing HEK293 cells and negative staining on parentals were designated as "hits" for further screening. 192 hits were identified in the primary FACS screen and 143 hits were confirmed in secondary and tertiary FACS screens.

Example 2. Functional Screening of ANTI-TMPRSS6 Antibodies: Identification, Generation, and Sequencing of Monoclonal ANTI-TMPRSS6 Antibodies and Humanized Variants HAMP-Luciferase Reporter Assay A hepcidin promoter-luciferase reporter assay was used to measure responses of the HAMP promoter to various anti-TMPRSS6 antibodies (Du, X. et al., 2008. *Science* 320: 1088-1092; modified to use human HAMP promoter instead of mouse Hamp promoter as originally disclosed). For the HAMP-luciferase report assay, a 2.5 kb HAMP promoter fragment (Reference Genome GRCh38) was spliced upstream from a sequence encoding firefly luciferase. A control construct encoding *Renilla* luciferase, driven by a thymidine kinase promoter (Promega, E6931) was used as an internal control. These constructs were co-transfected into HepG2 cells (ATCC, HB-8065), together with constructs encoding TMPRSS6. Transfected HepG2 cells expressing TMPRSS6 were pre-treated with various concentrations of purified mAb diluted in starvation medium containing minimum essential medium (MEM, ATCC)+1% heat inactivated fetal bovine serum (FBS, Gibco)+1 mM sodium pyruvate+non-essential amino acids solution (Gibco)+10 mM HEPES (Gibco)+1% Pen/Strep (Gibco) for about 3 hrs before treatment with recombinant hBMP6 (R&D Systems) at a final concentration of 25-60 ng/ml to trigger BMP-SMAD-mediated signaling. Purified mouse IgG (Sigma-Aldrich) or human IgG1 (BioXcell) was used as a control. Upon an overnight treatment of hBMP6, cells were lysed and luciferase substrate were added. Luminescence readings from firefly luciferase and *Renilla* luciferase were each recorded by measuring total luminescence. Activity was calculated as the ratio of firefly luciferase luminescence to *Renilla* luciferase luminescence (control). Results for these assays are shown in FIGS. 2A-2F.

Functional Screening In Vitro

To screen for functionally active hybridomas, the HAMP-luciferase reporter assay described above was used to test all 143 HuTMPRSS6 binding hybridomas ("hits"). Supernatants of ten (10) out of 143 HuTMPRSS6 binding hybridomas increased HAMP promoter activity (data not shown), and were identified as "active clones" to undergo further testing. These ten (10) active clones were tested for cross reactivity against murine target MoTMPRSS6 as described in Example 4 below, and three (3) showed binding towards both HuTMPRSS6 and MoTMPRSS6 as measured by FACS. These three cross-reactive clones were further plated at a density of 1 cell/well in 192 wells of 384-well plates to generate monoclonal hybridoma clones, the resulting subclones that exhibited desired functional activity and cross-reactivity against non-human targets, e.g. murine TMPRSS6 (moTMPRSS6) and/or cynomolgus monkey TMPRSS6 (cynoTMPRSS6) were identified as MWTx-001, MWTx-002, and MWTx-003.

Sequences of anti-TMPRSS6 Antibodies MWTx-001, MWTx-002, and MWTx-003

Sequences of MWTx-001, MWTx-002, and MWTx-003 were determined by isolating mRNAs from each hybridoma sample, carrying out reverse transcription polymerase chain reaction (RT-PCR) with unique mouse IgG-specific primer sets to amplify the target variable regions for sequencing. A unique heavy chain and a unique light chain were identified for each anti-TMPRSS6 antibody. The nucleotide sequence of each heavy chain and each light chain was determined. Amino acid sequences encoded by the nucleotide sequences were determined, CDR regions were identified using the Kabat numbering system. Table 1 presents heavy chain and light chain variable region amino acid sequences, and amino acid sequences of identified CDRs (based on Kabat numbering) and heavy chain and light chain variable region nucleotide sequences for each of MWTx-001, MWTx-002, and MWTx-003.

TABLE 1

Sequences of variable regions of anti-TMPRSS6 monoclonal antibodies MWTx-001, MWTx-002, and MWTx-003

MWTx-001
Heavy chain of MWTx-001:
Protein sequence of the variable region:
QVQLQQPGAELAKPGASVKMSCKASGYTFTSYWITWVKQRPGQDLEWIGNIYPGSGST
YYNEKFKSKATLTVDTSSRTAYMQLSSLTSADSAVYYCAPYDSDYAMDYWGQGTSVT
VSS (SEQ ID NO: 1)

| HC CDR-1 | HC CDR-2 | HC CDR-3 |
| --- | --- | --- |
| GYTITSYW (SEQ ID NO: 2) | IYPGSGST (SEQ ID NO: 3) | APYDSDYAMDY (SEQ ID NO: 4) |

Nucleotide sequence of the variable region:
CAGGTCCAACTGCAGCAGCCTGGGGCTGAGCTTGCGAAGCCTGGGGCTTCAGTGAA
GATGTCCTGCAAGGCTTCTGGCTACACCTTCACCAGCTACTGGATAACCTGGGTGA
AGCAGAGGCCTGGACAAGACCTTGAGTGGATTGGAAATATTTATCCTGGTAGTGGT
AGTACTTACTACAATGAGAAGTTCAAGAGCAAGGCCACACTGACTGTAGACACATC
CTCCAGAACAGCCTACATGCAGCTCAGCAGTCTGACATCTGCGGACTCTGCGGTCT
ATTACTGTGCCCCCTATGATTCCGACTATGCTATGGACTACTGGGGTCAAGGAACCT
CAGTCACCGTCTCCTCA (SEQ ID NO: 5)

Light chain of MWTx-001:
Protein sequence of the variable region:
DIKMTQSPSSMYASLGERVTITCKASQDINNYLSWFQQKPGKSPKTLIYRANRLVDGVP
SRVSGSGSGQDYSLTISSLEYEDVGIYFCLQYDEFPLTFGAGTKLELK (SEQ ID NO: 6)

| LC CDR-1 | LC CDR-2 | LC CDR-3 |
| --- | --- | --- |
| QDINNY (SEQ ID NO: 7) | RAN (SEQ ID NO: 8) | LQYDEFPLT (SEQ ID NO: 9) |

Nucleotide sequence of the variable region
GACATCAAGATGACCCAGTCTCCATCTTCCATGTATGCATCTCTAGGAGAGAGAGT
CACTATCACTTGCAAGGCGAGTCAGGACATTAATAACTATTTAAGCTGGTTCCAGC
AGAAACCAGGGAAATCTCCTAAGACCCTGATCTATCGTGCAAACAGATTGGTAGAT
GGGGTCCCATCAAGGGTCAGTGGCAGTGGATCTGGGCAAGATTATTCTCTCACCAT
CAGCAGCCTGGAGTATGAAGATGTGGGAATTTATTTTTGTCTACAGTATGATGAGTT
TCCTCTCACGTTCGGTGCTGGGACCAAGCTGGAGCTGAAA (SEQ ID NO: 10)

MWTx-002
Heavy chain of MWTx-002:
Protein sequence of the variable region:
EVQLQQSGAELVKPGASVKLSCTASGFNIKDYYIHWVKERTEQGLEWFGRIDPEDGES
EYAPKFQGKATLTADTSSNTAYLQLSSLTSEDTAVYYCTRGDSMMVTYFDYWGQGTT
LTVSSE (SEQ ID NO: 11)

TABLE 1-continued

Sequences of variable regions of anti-TMPRSS6 monoclonal
antibodies MWTx-001, MWTx-002, and MWTx-003

| HC CDR-1 | HC CDR-2 | HC CDR-3 |
|---|---|---|
| GFNIKDYY (SEQ ID NO: 12) | IDPEDGES (SEQ ID NO: 13) | TRGDSMMVTYFDY (SEQ ID NO: 14) |

Nucleotide sequence of the variable region:
GAGGTTCAGCTGCAGCAGTCTGGGGCAGAACTTGTGAAGCCAGGGGCCTCAGTCAA
GTTGTCCTGCACAGCCTCTGGCTTCAACATTAAAGACTACTATATACACTGGGTGAA
AGAGAGGACTGAACAGGGCCTGGAGTGGTTTGGAAGGATTGATCCTGAGGATGGT
GAAAGTGAATATGCCCCGAAATTCCAGGGCAAGGCCACTTTAACAGCAGACACATC
CTCCAATACAGCCTACCTGCAGCTCAGCAGCCTGACATCTGAGGACACTGCCGTCT
ATTACTGTACTAGAGGAGACTCTATGATGGTTACCTACTTTGACTACTGGGGCCAA
GGCACCACTCTCACGGTCTCCTCA (SEQ ID NO: 15)

Light chain of MWTx-002:
Protein sequence of the variable region:
DIVMTQSHKFMSTSVGDRVSITCKASQDVSTAVAWYQQKPGQSPKLLIYWAFTRHTGV
PDRFTSTGSGTDYALTISSVQAEDLALYYCQQHYRSPWTFGGGTKLEIK (SEQ ID NO:
16)

| LC CDR-1 | LC CDR-2 | LC CDR-3 |
|---|---|---|
| QDVSTA (SEQ ID NO: 17) | WAF (SEQ ID NO: 18) | QQHYRSPWT (SEQ ID NO: 19) |

Nucleotide sequence of the variable region:
GACATTGTGATGACCCAGTCTCACAAATTCATGTCCACATCAGTAGGAGACAGGGT
CAGCATCACCTGCAAGGCCAGTCAGGATGTGAGTACTGCTGTAGCCTGGTATCAAC
AAAAACCAGGGCAATCTCCTAAACTACTGATTTACTGGGCTITCACCCGTCACACT
GGAGTCCCTGATCGCTTCACAAGCACTGGATCTGGGACAGATTATGCTCTCACCAT
CAGCAGTGTGCAGGCTGAAGACCTGGCACTTTATTACTGTCAGCAACATTATCGCA
GTCCGTGGACGTTCGGTGGAGGCACCAAACTGGAAATCAAA(SEQ ID NO: 20)

MWTx-003
Heavy chain of MWTx-003:
Protein sequence of the variable region:
EVQLQQSGAELVKPGASVKLSCTASGFNIEDYYIHWVKERTEQGLEWIGRIDPEDGETT
YAPQFQGKATIIPDTSSNTAYMQLSSLTSEDAAVYYCARSIYLDPMDYWGQGTSVTSS
(SEQ ID NO: 21)

| HC CDR-1 | HC CDR-2 | HC CDR-3 |
|---|---|---|
| GFNIEDYY (SEQ ID NO: 22) | IDPEDGET (SEQ ID NO: 23) | ARSIYLDPMDY (SEQ ID NO: 24) |

Nucleotide sequence of the variable region:
GAAGTTCAGCTGCAGCAGTCTGGGGCAGAACTTGTGAAGCCAGGGGCCTCAGTCAA
GTTGTCCTGCACAGCTTCTGGCTTCAACATTGAAGACTACTATATACACTGGGTGAA
GGAGAGGACTGAACAGGGCCTGGAGTGGATTGGAAGGATTGATCCTGAGGATGGT
GAAACTACATATGCCCCGCAGTTCCAGGGCAAGGCCACTATAATACCAGACACATC
CTCCAACACAGCCTACATGCAGCTCAGCAGCCTGACATCTGAGGACGCTGCCGTCT
ATTACTGTGCTAGATCGATCTACCTTGATCCTATGGACTACTGGGGTCAAGGAACCT
CAGTCACCGTCTCCTCA (SEQ ID NO: 25)

Light chain of MWTx-003:
Protein sequence of the variable region:
DIVMTQSHKFMSTSVGDRVSITCKASQDVTTAVAWYQQKPGQSPKILIYWATTRHTGV
PDRFTGSISGTTYILTISSVQAEDLALYYCQQHYSTPYTFGGGTKLEIK (SEQ ID
NO: 26)

| LC CDR-1 | LC CDR-2 | LC CDR-3 |
|---|---|---|
| QDVTTA (SEQ ID NO: 27) | WAT (SEQ ID NO: 28) | QQHYSTPYT (SEQ ID NO: 29) |

Nucleotide sequence of the variable region:
GACATTGTGATGACCCAGTCTCACAAATTCATGTCCACATCAGTAGGAGACAGGGT
CAGCATCACCTGCAAGGCCAGTCAGGATGTGACTACTGCTGTCGCCTGGTATCAAC
AAAAACCAGGACAGTCTCCTAAAATACTGATTTACTGGGCAACCACCCGGCACACT
GGAGTCCCTGATCGCTTCACAGGCAGTATATCTGGGACAACTTATATTCTCACCATC
AGTAGTGTGCAGGCTGAAGACCTGGCACTTTATTACTGTCAGCAACATTATAGCAC
TCCGTACACGTTCGGAGGGGGGACCAAGCTGGAAATAAAA (SEQ ID NO: 30)

Generation and Screening of Humanized Anti-TMPRSS6 Antibody Variants

Humanization of the parental antibody was performed utilizing CDR grafting onto human antibody frameworks. Homology modeling of the parental antibody's 3-dimensional structure was first performed to establish a structural model of the parental antibody. Amino acid sequences for the variable fragment framework were identified based on the overall sequence identity, matching VH-VL interface positions, similarly classed CDR canonical positions, and removal of potential N-glycosylation sites. Humanized antibodies were designed by creating multiple hybrid sequences that fuse selected parts of the parental antibody sequence with the human framework sequences. The isotypes chosen to format humanized antibody were IgG1 for the heavy chain and IgG1 kappa for the light chain. Using the 3D model, these humanized sequences were methodically analyzed by eye and computer modeling to isolate the sequences that would most likely retain antigen binding. The goal was to maximize the amount of human sequence in the final humanized antibodies while retaining the original antibody specificity. Humanized variants, pairing the humanized VH and VL were then expressed and purified for affinity analysis.

In one round of designing, generating, and testing variants as part of an affinity analysis, four VH variants were generated with the VH-CDRs of the parental antibody MWTX-003 in corresponding positions in four different human IgG1-derived frameworks (SEQ ID NOS: 89-92), and four VL (VK) variants were generated with the VL-CDRs of the parental antibody MWTX-003 in corresponding positions in four different human IgG1 kappa-derived frameworks (SEQ ID NOS: 93-96). A total of sixteen (16) humanized variants representing every combination of the VH and VL (VK) variants were prepared according to a 4VH×4VK matrix, evaluated for antigen binding characteristics ($k_{on}$, $k_{off}$, KD) and found to have KD values in the nanomolar range, from 4.16E-07 (to 1.09E-08.

Variants that showed desired antigen binding affinity were selected for further evaluation and development. In some cases, parental CDR sequences were modified to avoid potential unwanted events such as aspartate isomerization.

To silence antibody effector function, in particular to silence antibody-dependent cellular cytotoxicity (ADCC), critical amino acid residues in the Fc region were identified and mutated (substituted) for all of the humanized antibody variants. Guidance available in the published literature concerning Fc mutations to achieve the goal of abolishing ADCC was used to inform the present mutations, for example removal of the native Fc N-linked glycosylation site (N297A mutation) in hIgG1, or substitutions of leucine at positions 234 and 235 of the lower hinge region in the Fc (LALA double mutation) as described by (Tamm A, Schmidt R E. IgG binding sites on human Fc gamma receptors. *Int Rev Immunol.* 1997; 16(1-2):57-85. doi: 10.3109/08830189709045703; Jefferis R, Lund J. Interaction sites on human IgG-Fc for FegammaR: current models. *Immunol Lett.* 2002 Jun. 3; 82(1-2):57-65. doi: 10.1016/s0165-2478 (02)00019-6). In the present variants, the N297A mutation was introduced in the Fc of the hzMWTx-001Var and hzMWTx-002Var antibodies, and the LALA mutation was introduced into the Fc of the hzMWTx-003Var antibody, to achieve the same goal of reducing or silencing ADCC (Table 3, SEQ ID NOs: 73, 77, 81).

After evaluation, humanized anti-TMPRSS6 antibody variants hzMWTx-001Var, hzMWTx-002Var, and hzMWTx-003Var were selected for further testing. Sequences and features of humanized variants are shown in Tables 2 and 3 below.

Recombinant Production of Humanized Anti-TMPRSS6 Antibody Variants

Expression constructs for humanized anti-TMPRSS6 antibody variants were engineered with internal ribosome entry site (IRES) between LC- and HC-coding DNA sequences, codon optimized by Geneart DNA synthesis and cloned into pcDNA3.4 mammalian expression vector (ThermoFisher). The sequences of DNA inserts were verified by sequencing. For recombinant antibody production, the expression constructs were used for transient transfection using ExpiCHO expression system (ThermoFisher) following manufacturer's instruction. The expressed antibodies were purified by Protein A affinity chromatography. The yield of antibody production from transient transfection ranged from 50 mg to 300 mg per liter, with purity >95% and <1 EU/ml endotoxin level.

Sequences of Humanized Anti-TMPRSS6 Antibody Variants hzMWTx-001Var, hzMWTx-002Var, and hzMWTx-003Var Humanized anti-TMPRSS6 antibody variants hzMWTx-001Var, hzMWTx-002Var, and hzMWTx-003Var were selected for further testing. Sequences of the variable region of each variable region are shown in Table 2 below, where identified CDRs are indicated by underlining and changes made in the humanized variant CDR sequences relative to the parental antibody are indicated and discussed.

TABLE 2

Amino acid and nucleotide sequences of variable regions of humanized anti-TMPRSS6 antibody variants hzMWTx-001Var, hzMWTx-002Var, and hzMWTx-003Var hzMWTx-001Var
Heavy chain of hzMWTx-001Var:
Protein sequence of variable region (CDR residues that differ from parental sequence in bold):
EVQLVQSGAEVKKPGASVKVSCKASGYTFTSYWITWVRQAPGQRLEWIGNIYPGSGST
YYNEKFKSKATITRDTSSRTAYMELSSLRSEDTAVYYCAPYDADYAMDYWGQGTLVT
VSS (SEQ ID NO: 31)

| hzMWTx-001Var<br>HC CDR-1 | hzMWTx-001Var<br>HC CDR-2 | hzMWTx-001Var<br>HC CDR-3 |
|---|---|---|
| GYTFTSYW<br>(SEQ ID NO: 32) | IYPGSGST<br>(SEQ ID NO: 33) | APYDADYAMDY<br>(SEQ ID NO: 34) |

Comment on underlined sequence DA in hzMWTx-001Var HC CDR-2:
Original sequence in parental antibody is DS here. It was determined that DS is a critical TABLE 2-continued Amino acid and nucleotide sequences of variable regions of humanized anti-TMPRSS6 antibody variants hzMWTx-001Var, hzMWTx-002Var, and hzMWTx-003Var combination that could result in aspartate isomerization, so S (Serine) at this position was changed to A (Alanine).

Nucleotide sequence of the variable region:
GAAGTGCAGCTGGTGCAATCTGGCGCCGAAGTGAAGAAACCTGGCGCCTCTGTGAA
GGTGTCCTGCAAGGCTTCCGGCTACACCTTTACCAGCTACTGGATCACCTGGGTCCG
ACAGGCTCCTGGCCAGAGACTGGAATGGATCGGCAACATCTACCCTGGCTCCGGCT
CCACCTACTACAACGAGAAGTTCAAGTCCAAGGCCACAATCACCCGGGACACCTCT
TCCAGAACCGCCTACATGGAACTGTCCAGCCTGAGATCTGAGGACACCGCCGTGTA
CTACTGCGCCCCTTACGACGCCGACTACGCCATGGATTATTGGGGCCAGGGCACCC
TGGTCACCGTGTCCTCT (SEQ ID NO: 35)

Light chain of hzMWTx-001Var:
Protein sequence of variable region (CDR residues that differ from parental sequence in bold):
DIQMTQSPSSLSASVGDRVTITCKASQDISNYLSWFQQKPGKAPKLLIYRANRLVEGVPS
RFSGSGSGTDFTLTISSLQPEDFATYFCLQYDEFPLTFGGGTKVEIK (SEQ ID NO: 36)

| hzMWTx-001Var LC CDR-1 | hzMWTx-001Var LC CDR-2 | hzMWTx-001Var LC CDR-3 |
| --- | --- | --- |
| QDISNY (SEQ ID NO: 37) | RAN (SEQ ID NO: 38) | LQYDEFPLT (SEQ ID NO: 39) |

Comment on underlined sequence SN in hzMWTx-001Var LC CDR-1:
Original sequence in parental antibody is NN here. It was determined that NN is a critical combination that could result in asparagine deamidation, so N (Asparagine) at this position was changed to S (Serine).

Nucleotide sequence of the variable region:
GACATCCAGATGACCCAGTCTCCATCCTCTCTGTCCGCCTCTGTGGGCGACAGAGTG
ACCATCACATGCAAGGCCAGCCAGGACATCTCCAACTACCTGTCCTGGTTCCAGCA
GAAGCCTGGCAAGGCTCCCAAGCTGCTGATCTACAGAGCCAACAGACTGGTGGAA
GGCGTGCCCTCCAGATTCTCCGGATCTGGCTCTGGCACCGACTTTACCCTGACAATC
TCCAGCCTGCAGCCTGAGGACTTCGCTACCTACTTCTGCCTGCAATACGACGAGTTC
CCTCTGACCTTTGGCGGAGGCACCAAGGTGGAAATCAAG (SEQ ID NO: 40)

hzMWTx-002Var
Heavy chain of hzMWTx-002Var:
Protein sequence of variable region (CDR residues that differ from parental sequence in bold):
EVQLVQSGAEVKKPGASVKVSCKASGFNIKDYYIHWVRQATGQGLEWMGRIDPEDAE
SEYAPKFQGRVTITADTSTDTAYMELSSLRSEDTAVYYCTRGDSMMVTYFDYWGQGT
LVTVSS (SEQ ID NO: 41)

| hzMWTx-002Var HC CDR-1 | hzMWTx-002Var HC CDR-2 | hzMWTx-002Var HC CDR-3 |
| --- | --- | --- |
| GFNIKDYY (SEQ ID NO: 42) | IDPEDAES (SEQ ID NO: 43) | TRGDSMMVTYFDY (SEQ ID NO: 44) |

Comment on underlined sequence DA in hzMWTx-002Var HC CDR-2:
Original sequence in parental antibody is DG here. It was determined that DG is a critical combination that could likely result in aspartate isomerization, so G (Glycine) at this position was changed to A (Alanine).

Nucleotide sequence of the variable region:
GAAGTGCAGCTGGTGCAATCTGGCGCCGAAGTGAAGAAACCTGGCGCCTCTGTGAA
GGTGTCCTGCAAGGCCTCTGGCTTCAACATCAAGGACTACTACATCCACTGGGTCC
GACAGGCTACCGGACAGGGACTTGAGTGGATGGGCAGAATCGACCCTGAGGACGC
CGAGTCTGAGTACGCCCCTAAGTTTCAGGGCAGAGTGACCATCACCGCCGACACCT
CTACCGACACCGCCTACATGGAACTGTCCAGCCTGAGATCTGAGGACACCGCCGTG
TACTACTGCACCAGAGGCGACTCCATGATGGTTACCTACTTCGACTACTGGGGCCA
GGGCACCCTGGTCACAGTTTCTTCC (SEQ ID NO: 45)

Light chain of hzMWTx-002Var:
Protein sequence of variable region:
DIQMTQSPSSLSASVGDRVTITCKASQDVSTAVAWYQQKPGKAPKLLIYWAFTRHTGV
PSRFSGSGSGTDYALTISSLQPEDFATYYCQQHYRSPWTFGGGTKVEIK (SEQ ID NO: 46)

| hzMWTx-002Var LC CDR-1 | hzMWTx-002Var LC CDR-2 | hzMWTx-002Var LC CDR-3 |
| --- | --- | --- |
| QDVSTA (SEQ ID NO: 47) | WAF (SEQ ID NO: 48) | QQHYRSPWT (SEQ ID NO: 49) |

TABLE 2-continued

Amino acid and nucleotide sequences of variable regions of humanized anti-TMPRSS6 antibody variants hzMWTx-001Var, hzMWTx-002Var, and hzMWTx-003Var Nucleotide sequence of the variable region:
GACATCCAGATGACCCAGTCTCCATCCTCTCTGTCCGCCTCTGTGGGCGACAGAGTG
ACCATCACATGCAAGGCCTCTCAGGACGTGTCCACCGCCGTTGCTTGGTATCAGCA
GAAGCCTGGCAAGGCCCCTAAGCTGCTGATCTACTGGGCCTTCACCAGACACACCG
GCGTGCCCTCTAGGTTCTCCGGCTCTGGCTCTGGCACCGATTACGCTCTGACAATCT
CCAGCCTGCAGCCTGAGGACTTCGCCACCTACTACTGCCAGCAGCACTACAGAAGC
CCCTGGACATTTGGCGGAGGCACCAAGGTGGAAATCAAG (SEQ ID NO: 50)

hzMWTx-003Var
Heavy chain of hzMWTx-003Var:
Protein sequence of variable region (CDRs indicated by underlining; CDR residues that differ from parental CDR sequence indicated in bold):
QVQLVQSGAEVKKPGASVKVSCKAS<u>GFNIEDYY</u>MHWVRQAPGQRLEWMG<u>RIDPEDA
ET</u>TYSPKFQGRVTIIPDTSANTAYMELSSLRSEDTAVYYC<u>ARSIYLDPMDY</u>WGQGTLVT
VSS (SEQ ID NO: 51)

| hzMWTx-03Var HC CDR-1 | hzMWTx-003Var HC CDR-2 | hzMWTx-003Var HC CDR-3 |
|---|---|---|
| GFNIEDYY (SEQ ID NO: 52) | IDPEDAET (SEQ ID NO: 53) | ARSIYLDPMDY (SEQ ID NO: 54) |

Comment on underlined sequence DA in hzMWTx-003Var HC CDR-2:
Original sequence in parental antibody is DG here. It was determined that DG is a critical combination that could likely result in aspartate isomerization, so G (Glycine) at this position was changed to A (Alanine).

Nucleotide sequence of the variable region:
CAGGTGCAGCTGGTGCAGTCTGGCGCCGAAGTGAAAAAGCCTGGCGCCTCTGTGAA
GGTGTCCTGCAAGGCCTCTGGCTTCAACATCGAGGACTACTACATGCACTGGGTCC
GACAGGCCCCTGGCCAGAGATTGGAATGGATGGGCAGAATCGACCCCGAGGACGC
CGAGACAACCTACTCTCCTAAGTTCCAGGGCGCGTGACAATCATCCCTGACACCT
CTGCCAACACCGCCTACATGGAACTGTCCAGCCTGAGATCTGAGGACACCGCCGTG
TACTACTGCGCCCGGTCTATCTACCTGGACCCTATGGACTATTGGGGCCAGGGCAC
CCTGGTCACAGTGTCCTCT (SEQ ID NO: 55)

Light chain of hzMWTx-003Var:
Protein sequence of variable region:
DIQMTQSPKSLSASVGDRVTITCRAS<u>QDVTTA</u>LAWYQQKPGQSPKLLIY<u>WAT</u>TRHSGV
PSRFSGSGSGTDFTLTISSLQPEDFATYYC<u>QQHSTPYT</u>FGQGTKLEIK (SEQ ID NO: 56)

| hzMWTx-003Var LC CDR-1 | hzMWTx-003Var LC CDR-2 | hzMWTx-003Var LC CDR-3 |
|---|---|---|
| QDVTTA (SEQ ID NO: 57) | WAT (SEQ ID NO: 58) | QQHYSTPYT (SEQ ID NO: 59) |

Nucleotide sequence of the variable region:
GACATCCAGATGACCCAGTCTCCAAAGTCTCTGTCCGCCTCCGTGGGCGACAGAGT
GACCATCACCTGTAGAGCCTCTCAGGACGTGACCACCGCTCTGGCTTGGTATCAGC
AGAAGCCTGGCCAGTCTCCTAAGCTGCTGATCTACTGGGCCACCACCAGACACTCT
GGCGTGCCCTCTAGATTCTCCGGCTCTGGCTCTGGCACCGACTTTACCCTGACAATC
TCCAGCCTGCAGCCTGAGGACTTCGCCACCTACTACTGCCAGCAGCACTACAGCAC
CCCTTACACCTTTGGCCAGGGCACCAAGCTGGAAATCAAG (SEQ ID NO: 60)

Table 3 shows complete heavy chain and light chain protein and nucleotide sequences of anti-TMPRSS6 monoclonal antibodies MWTx-001, MWTx-002, and MWTx-003, and humanized anti-TMPRSS6 antibody variants hzMWTx-001Var, hzMWTx-002Var, and hzMWTx-003Var. Heavy chain protein sequences of humanized anti-TMPRSS6 antibody variants hzMWTx-001Var, hzMWTx-002Var, and hzMWTx-003Var show the location of mutations (changes) introduced to reduce ADCC as described above.

TABLE 3

Heavy chain and light chain sequences of anti-TMPRSS6 monoclonal antibodies MWTx-001, MWTx-002, and MWTx-003, and humanized anti-TMPRSS6 antibody variants hzMWTx-001Var, hzMWTx-002Var, and hzMWTx-003Var Anti-TMPRSS6 monoclonal antibodies MWTx-001
Heavy chain of MWTx-001:
Protein sequence (Constant region indicated by italics):
QVQLQQPGAELAKPGASVKMSCKASGYTFTSYWITWVKQRPGQDLEWIGNIYPGSGST TABLE 3-continued Heavy chain and light chain sequences of anti-TMPRSS6 monoclonal
antibodies MWTx-001, MWTx-002, and MWTx-003, and humanized anti-
TMPRSS6 antibody variants hzMWTx-001Var, hzMWTx-002Var, and hzMWTx-003Var YYNEKFKSKATLTVDTSSRTAYMQLSSLTSADSAVYYCAPYDSDYAMDYWGQGTSVT
VSSAKTTAPSVYPLAPVCGDTTGSSVTLGCLVKGYFPEPVTLTWNSGSLSSGVHTFPAVLQSD
LYTLSSSVTVTSSTWPSQSITCNVAHPASSTKVDKKIEPRGPTIKPCPPCKCPAPNLLGGPSVFI
FPPKIKDVLMISLSPIVTCVVVDVSEDDPDVQISWFVNNVEVHTAQTQTHREDYNSTLRVVSA
LPIQHQDWMSGKEFKCKVNNKDLPAPIERTISKPKGSVRAPQVYVLPPPEEEMTKKQVTLTC
MVTDFMPEDIYVEWTNNGKTELNYKNTEPVLDSDGSYFMYSKLRVEKKNWVERNSYSCSVV
HEGLHNHHTTKSFSRTPG (SEQ ID NO: 61)

Nucleotide sequence:
CAGGTCCAACTGCAGCAGCCTGGGGCTGAGCTTGCGAAGCCTGGGGCTTCAGTGAAGA
TGTCCTGCAAGGCTTCTGGCTACACCTTCACCAGCTACTGGATAACCTGGGTGAAGCAG
AGGCCTGGACAAGACCTTGAGTGGATTGGAAATATTTATCCTGGTAGTGGTAGTACTTA
CTACAATGAGAAGTTCAAGAGCAAGGCCACACTGACTGTAGACACATCCTCCAGAACA
GCCTACATGCAGCTCAGCAGTCTGACATCTGCGGACTCTGCGGTCTATTACTGTGCCCCC
TATGATTCCGACTATGCTATGGACTACTGGGGTCAAGGAACCTCAGTCACCGTCTCCTC
AGCTAAAACAACAGCCCCATCGGTCTATCCACTGGCCCCTGTGTGTGGAGATACAACTG
GCTCCTCGGTGACTCTAGGATGCCTGGTCAAGGGTTATTTCCCTGAGCCAGTGACCTTG
ACCTGGAACTCTGGTTCCCTGTCCAGTGGTGTGCACACCTTCCCAGCTGTCCTGCAGTCT
GACCTCTACACCCTCAGCTCAAGCGTGACTGTAACCAGCTCGACCTGGCCCAGCCAGTC
CATCACCTGCAATGTGCCCACCCGGCAAGCAGCACCAAGGTGGACAAGAAAATTGAG
CCCAGAGGGCCCACAATCAAGCCCTGTCCTCCATGCAAATGCCCAGCACCTAACCTCTT
GGGTGGACCATCCGTCTTCATCTTCCCTCCAAAGATCAAGGATGTACTCATGATCTCCCT
GAGCCCCATAGTCACATGTGTAGTCGTTGATGTGAGCGAGGATGACCCAGATGTCCAGA
TCAGCTGGTTTGTGAACAACGTGGAAGTGCACACTGCTCAGACAGACGCATAGAGA
GGATTACAACAGTACTCTCCGGGTTGTCAGTGCCCTCCCCATCCAGCACCAGGACTGGA
TGAGTGGCAAGGAGTTCAAATGCAAGGTCAACAACAAAGACCTCCCAGCGCCCATCGA
GAGAACCATCTCAAAACCCAAAGGGTCAGTAAGAGCTCCACAGGTATATGTCTTGCCTC
CACCAGAAGAGGAGATGACTAAGAAACAGGTCACTCTGACCTGCATGGTCACAGACTT
CATGCCTGAAGACATTTACGTGGAGTGGACCAACAACGGGAAAACAGAGCTAAACTAC
AAGAACACTGAACCAGTCCTGGACTCTGATGGTTCTTACTTCATGTACAGCAAGCTGAG
AGTGGAGAAGAAGAACTGGGTGGAGAGAAATAGCTACTCCTGTTCAGTGGTCCACGAG
GGTCTGCACAATCACCACACGACTAAGAGCTTCTCCCGGACTCCGGGTTAGTAA (SEQ
ID NO: 62)

Light chain of MWTx-001:
Protein sequence (Constant region indicated by italics):
DIKMTQSPSSMYASLGERVTITCKASQDINNYLSWFQQKPGKSPKTLIYRANRLVDGVP
SRVSGSGSGQDYSLTISSLEYEDVGIYFCLQYDEFPLTFGAGTKLELKRADAAPTVSIFPPS
SEQLTSGGASVVCFLNNFYPKDINVKWKIDGSERQNGVLNSWTDQDSKDSTYSMSSTLTLTK
DEYERHNSYTCEATHKTSTSPIVKSFNRNEC (SEQ ID NO: 63)

Nucleotide sequence:
GACATCAAGATGACCCAGTCTCCATCTTCCATGTATGCATCTCTAGGAGAGAGAGTCAC
TATCACTTGCAAGGCGAGTCAGGACATTAATAACTATTTAAGCTGGTTCCAGCAGAAAC
CAGGGAAATCTCCTAAGACCCTGATCTATCGTGCAAACAGATTGGTAGATGGGGTCCCA
TCAAGGGTCAGTGGCAGTGGATCTGGGCAAGATTATTCTCTCACCATCAGCAGCCTGGA
GTATGAAGATGTGGGAATTTATTTTTGTCTACAGTATGATGAGTTTCCTCTCACGTTCGG
TGCTGGGACCAAGCTGGAGCTGAAAAGAGCTGACGCCGCTCCTACCGTGTCCATCTTTC
CACCTAGCAGCGAGCAGCTGACAAGCGGCGGAGCCAGCGTCGTGTGCTTCCTGAACAA
CTTCTACCCCAAGGACATCAACGTGAAGTGGAAGATCGACGGCAGCGAGAGACAGAAC
GGCGTGCTGAATAGCTGGACCGACCAGGACAGCAAGGACTCCACCTACAGCATGTCCA
GCACACTGACCCTGACCAAGGACGAGTACGAGCGGCACAACAGCTACACATGCGAGGC
CACACACAAGACCAGCACAAGCCCCATCGTGAAGTCCTTCAACCGGAACGAGTGC (SEQ
ID NO: 64)

MWTx-002
Heavy chain of MWTx-002:
Protein sequence (Constant region indicated by italics):
EVQLQQSGAELVKPGASVKLSCTASGFNIKDYYIHIWVKERTEQGLEWFGRIDPEDGESE
YAPKFQGKATLTADTSSNTAYLQLSSLTSEDTAVYYCTRGDSMMVTYFDYWGQGTTL
TVSSKTTPPSVYPLAPGCGDTTGSSVTLGCLVKGFPESVTVTWNSGSLSSSVHTFPALLQSGL
YTMSSSVTVPSSTWPSQTVTCSVAHPASSTTVDKKLEPSGPISTINPCPPCKECHKCPAPNLEG
GPSVFIFPPNIKDVLMISLTPKVTCVVVDVSEDDPDVQISWFVNNVEVHTAQTQTHREDYNST
IRVVSTLPIQHQDWMSGKEFKCKVNNKDLPSPIERTISKIKGLVRAPQVYILPPPAEQLSRKDV
SLTCLVVGFNPGDISVEWTSNGHTEENYKDTAPVLDSDGSYFIYSKLNMKTSKWEKTDSFSCN
VRHEGLKNYYLKKTISRSPGK (SEQ ID NO: 65)

Nucleotide sequence:
GAGGTTCAGCTGCAGCAGTCTGGGGCAGAACTTGTGAAGCCAGGGGCCTCAGTCAAGT
TGTCCTGCACAGCTTCTGGCTTCAACATTAAAGACTACTATATACACTGGGTGAAAGAG
AGGACTGAACAGGGCCTGGAGTGGTTTGGAAGGATTGATCCTGAGGATGGTGAAAGTG
AATATGCCCCGAAATTCCAGGGCAAGGCCACTTTAACAGCAGACACATCCTCCAATACA
GCCTACCTGCAGCTCAGCAGCCTGACATCTGAGGACACTGCCGTCTATTACTGTACTAG
AGGAGACTCTATGATGGTTACCTACTTTGACTACTGGGGCCAAGGCACCACTCTCACGG
TCTCCTCAAAGACCACACCTCCAGCGTGTACCCTCTGGCTCCTGGCTGTGGCGATACA
ACAGGCAGCTCTGTGACACTGGGCTGCCTGGTCAAGGGCTACTTTCCTGAGAGCGTGAC TABLE 3-continued Heavy chain and light chain sequences of anti-TMPRSS6 monoclonal
antibodies MWTx-001, MWTx-002, and MWTx-003, and humanized anti-
TMPRSS6 antibody variants hzMWTx-001Var, hzMWTx-002Var, and hzMWTx-003Var

```
AGTGACCTGGAACAGCGGCAGCCTGTCTAGCAGCGTGCACACCTTTCCAGCTCTGCTCC
AGAGCGGCCTGTACACCATGTCCTCTAGTGTGACCGTGCCTAGCAGCACCTGGCCTAGC
CAGACAGTGACATGTAGCGTGGCCCATCCTGCCAGCAGCACAACCGTGGACAAGAAGC
TGGAACCTAGCGGCCCCATCAGCACCATCAATCCCTGTCCTCCATGCAAAGAATGCCAC
AAGTGCCCCGCTCCTAACCTGGAAGGTGGCCCAAGCGTGTTCATCTTCCCACCTAACAT
CAAGGACGTGCTGATGATCAGCCTGACACCTAAAGTGACCTGCGTGGTGGTGGACGTGT
CCGAGGATGATCCCGATGTGCAGATCAGTTGGTTCGTGAACAACGTGGAAGTGCACAC
AGCCCAGACACAGACCCACAGAGAGGACTACAATAGCACCATTCGCGTGGTGTCCACA
CTGCCTATCCAGCACCAGGATTGGATGAGCGGCAAAGAGTTCAAGTGCAAAGTGAACA
ACAAGGACCTGCCTTCTCCAATCGAGCGGACCATCAGCAAGATCAAGGGACTCGTCAG
AGCCCCTCAGGTGTACATCTTGCCTCCACCAGCCGAGCAGCTGAGCAGAAAGGATGTGT
CCGTGACCTGTCTGGTCGTGGGCTTCAACCCTGGCGACATCAGCGTGGAATGGACCAGC
AATGGCCACACCGAGGAAAACTACAAGGACACAGCCCCTGTGCTGGACAGCGACGGCA
GCTACTTCATCTACAGCAAGCTGAACATGAAGACCAGCAAGTGGGAGAAAACCGACAG
CTTCTCCTGCAACGTGCGGCACGAGGGCCTGAAGAACTACTACCTGAAGAAACCATCT
CTCGGAGCCCCGGCAAG (SEQ ID NO: 66)
```

Light chain of MWTx-002:
Protein sequence (Constant region indicated by italics):
DIVMTQSHKFMSTSVGDRVSITCKASQDVSTAVAWYQQKPGQSPKLLIYWAFTRHTGV
PDRFTSTGSGTDYALTISSVQAEDLALYYCQQHYRSPWTFGGGTKLEIK*RADAAPTVSIF*
*PPSSEQLTSGGASVVCFLNNFYPKDINVKWKIDGSERQNGVLNSWTDQDSKDSTYSMSSTLTL*
*TKDEYERHNSYTCEATHKTSTSPIVKSFNRNEC* (SEQ ID NO: 67)

Nucleotide sequence:
```
GACATTGTGATGACCCAGTCTCACAAATTCATGTCCACATCAGTAGGAGACAGGGTCAG
CATCACCTGCAAGGCCAGTCAGGATGTGAGTACTGCTGTAGCCTGGTATCAACAAAAAC
CAGGGCAATCTCCTAAACTACTGATTTACTGGGCTTTCACCCGTCACACTGGAGTCCCTG
ATCGCTTCACAAGCACTGGATCTGGGACAGATTATGCTCTCACCATCAGCAGTGTGCAG
GCTGAAGACCTGGCACTTTATTACTGTCAGCAACATTATCGCAGTCCGTGGACGTTCGG
TGGAGGCACCAAACTGGAAATCAAAAGAGCTGACGCCGCTCCTACCGTGTCCATCTTTC
CACCTAGCAGCGAGCAGCTGACAAGCGGCGGAGCCAGCGTCGTGTGCTTCCTGAACAA
CTTCTACCCCAAGGACATCAACGTGAAGTGGAAGATCGACGGCAGCGAGAGACAGAAC
GGCGTGCTGAATAGCTGGACCGACCAGGACAGCAAGGACTCCACCTACAGCATGTCCA
GCACACTGACCCTGACCAAGGACGAGTACGAGCGGCACAACAGCTACACATGCGAGGC
CACACACAAGACCAGCACAAGCCCCATCGTGAAGTCCTTCAACCGGAACGAGTGC
(SEQ ID NO: 68)
```

MWTx-003
Heavy chain of MWTx-003:
Protein sequence (Constant region indicated by italics):
EVQLQQSGAELVKPGASVKLSCTASGFNIEDYYIHWVKERTEQGLEWIGRIDPEDGETT
YAPQFQGKATIIPDTSSNTAYMQLSSLTSEDAAVYYCARSIYLDPMDYWGQGTSVTVSS
*KTTPPSVYPLAPGCGDTTGSSVTLGCLVKGYFPESVTVTWNSGSLSSSVHTFPALLQSGLYTMS*
*SSVTVPSSTWPSQTVTCSVAHPASSTTVDKKLEPSGPISTINPCPPCKECHKCPAPNLEGGPSV*
*FIFPPNIKDVLMISLTPKVTCVVVDVSEDDPDVQISWFVNNVEVHTAQTQTHREDYNSTIRVV*
*STLPIQHQDWMSGKEFKCKVNNKDLPSPIERTISKIKGLVRAPQVYILPPPAEQLSRKDVSLTC*
*LVVGFNPGDISVEWTSNGHTEENYKDTAPVLDSDGSYFIYSKLNMKTSKWEKTDSFSCNVRH*
*EGLKNYYLKKTISRSPGK* (SEQ ID NO: 69)

Nucleotide sequence:
```
GAGGTTCAGCTGCAGCAGTCTGGCGCCGAGCTTGTGAAACCTGGCGCCTCTGTGAAGCT
GAGCTGTACCGCCAGCGGCTTCAACATCGAGGACTACATCCACTGGGTCAAAGAGC
GGACCGAGCAGGGACTCGAGTGGATCGGAAGAATCGACCCCGAGGACGGCGAGACAA
CATACGCCCCTCAGTTTCAGGGCAAAGCCACAATCATCCCCGACACCAGCAGCAACACC
GCCTACATGCAACTGAGCAGCCTGACCTCTGAAGATGCCGCCGTGTACTACTGCGCCCG
GTCCATCTATCTGGACCCCATGGATTATTGGGCCAGGGCACAAGCGTGACCGTGTCCT
CTAAGACCACACCTCCTAGCGTGTACCCTCTGGCTCCTGGCTGTGGCGATACAACAGGC
AGCTCTGTGACACTGGGCTGCCTGGTCAAGGGCTACTTTCCTGAGAGCGTGACAGTGAC
CTGGAACAGCGGCAGCCTGTCTAGCAGCGTGCACACCTTTCCAGCTCTGCTCCAGAGCG
GCCTGTACACCATGTCCTCTAGTGTGACCGTGCCTAGCAGCACCTGGCCTAGCCAGACA
GTGACATGTAGCGTGGCCCATCCTGCCAGCAGCACAACCGTGGACAAGAAGCTGGAAC
CTAGCGGCCCCATCAGCACCATCAATCCCTGTCCTCCATGCAAAGAATGCCACAAGTGC
CCCGCTCCTAACCTGGAAGGTGGCCCAAGCGTGTTCATCTTCCCACCTAACATCAAGGA
CGTGCTGATGATCAGCCTGACACCTAAAGTGACCTGCGTGGTGGTGGACGTGTCCGAGG
ATGATCCCGATGTGCAGATCAGTTGGTTCGTGAACAACGTGGAAGTGCACACAGCCCAG
ACACAGACCCACAGAGAGGACTACAATAGCACCATTCGCGTGGTGTCCACACTGCCTAT
CCAGCACCAGGATTGGATGAGCGGCAAAGAGTTCAAGTGCAAAGTGAACAACAAGGAC
CTGCCTTCTCCAATCGAGCGGACCATCAGCAAGATCAAGGGACTCGTCAGAGCCCCTCA
GGTGTACATCTTGCCTCCACCAGCCGAGCAGCTGAGCAGAAAGGATGTGTCCCTGACCT
GTCTGGTCGTGGGCTTCAACCCTGGCGACATCAGCGTGGAATGGACCAGCAATGGCCAC
ACCGAGGAAAACTACAAGGACACAGCCCCTGTGCTGGACAGCGACGGCAGCTACTTCA
TCTACAGCAAGCTGAACATGAAGACCAGCAAGTGGGAGAAAACCGACAGCTTCTCCTG
CAACGTGCGGCACGAGGGCCTGAAGAACTACTACCTGAAGAAACCATCTCTCGGAGC
CCCGGCAAG (SEQ ID NO: 70)
```

TABLE 3-continued

Heavy chain and light chain sequences of anti-TMPRSS6 monoclonal
antibodies MWTx-001, MWTx-002, and MWTx-003, and humanized anti-
TMPRSS6 antibody variants hzMWTx-001Var, hzMWTx-002Var, and hzMWTx-003Var Light chain of MWTx-003:
Protein sequence (Constant region indicated by italics):
DIVMTQSHKFMSTSVGDRVSITCKASQDVTTAVAWYQQKPGQSPKILIYWATTRHTGV
PDRFTGSISGTTYILTISSVQAEDLALYYCQQHYSTPYTFGGGTKLEIK*RADAAPTVSIFPP*
*SSEQLTSGGASVVCFLNNFYPKDINVKWKIDGSERQNGVLNSWTDQDSKDSTYSMSSTLTLTK*
*DEYERHNSYTCEATHKTSTSPIVKSFNRNEC* (SEQ ID NO: 71)

Nucleotide sequence:
GACATCGTGATGACCCAGAGCCACAAGTTCATGAGCACCAGCGTGGGCGACAGAGTGT
CCATCACCTGTAAAGCCAGCCAGGACGTGACAACAGCCGTGGCCTGGTATCAGCAGAA
GCCTGGCCAGTCTCCTAAGATCCTGATCTACTGGGCCACCACCAGACACACCGGCGTGC
CAGATAGATTCACCGGCAGCATCAGCGGCACCACCTACATCCTGACAATCAGCTCTGTG
CAGGCCGAGGATCTGGCCCTGTACTACTGTCAGCAGCACTACAGCACCCCTTACACCTT
TGGCGGAGGCACCAAGCTGGAAATCAAGAGAGCTGACGCCGCTCCTACCGTGTCCATCT
TTCCACCTAGCAGCGAGCAGCTGACAAGCGGCGGAGCCAGCGTCGTGTGCTTCCTGAAC
AACTTCTACCCCAAGGACATCAACGTGAAGTGGAAGATCGACGGCAGCGAGAGACAGA
ACGGCGTGCTGAATAGCTGGACCGACCAGGACAGCAAGGACTCCACCTACAGCATGTC
CAGCACACTGACCCTGACCAAGGACGAGTACGAGCGGCACAACAGCTACACATGCGAG
GCCACACACAAGACCAGCACAAGCCCCATCGTGAAGTCCTTCAACCGGAACGAGTGC
(SEQ ID NO: 72)

Humanized anti-TMPRSS6 antibody variants hzMWTx-001Var
Heavy chain of hzMWTx-001Var:
Protein sequence (Constant region indicated by italics;
N297A mutation indicated by bold):
EVQLVQSGAEVKKPGASVKVSCKASGYTFTSYWITWVRQAPGQRLEWIGNIYPGSGST
YYNEKFKSKATITRDTSSRTAYMELSSLRSEDTAVYYCAPYDADYAMDYWGQGTLVT
*VSSASTKGPSVFPLAPSSKSTSGGTAALGCLVKDYFPEPVTVSWNSGALTSGVHTFPAVLQSS*
*GLYSLSSVVTVPSSSLGTQTYICNVNHKPSNTKVDKKVEPKSCDKTHTCPPCPAPELLGGPSV*
*FLFPPKPKDTLMISRTPEVTCVVVDVSHEDPEVKFNWYVDGVEVHNAKTKPREEQY**A**STYRV*
*VSVLTVLHQDWLNGKEYKCKVSNKALPAPIEKTISKAKGQPREPQVYTLPPSRDELTKNQVSL*
*TCLVKGFYPSDIAVEWESNGQPENNYKTTPPVLDSDGSFFLYSKLTVDKSRWQQGNVFSCSV*
*MHEALHNHYTQKSLSLSPG* (SEQ ID NO: 73)

Nucleotide sequence:
GAAGTGCAGCTGGTGCAATCTGGCGCCGAAGTGAAGAAACCTGGCGCCTCTGTGAAGG
TGTCCTGCAAGGCTTCCGGCTACACCTTTACCAGCTACTGGATCACCTGGGTCCGACAG
GCTCCTGGCCAGAGACTGGAATGGATCGGCAACATCTACCCTGGCTCCGGCTCCACCTA
CTACAACGAGAAGTTCAAGTCCAAGGCCACAATCACCCGGGACACCTCTTCCAGAACC
GCCTACATGGAACTGTCCAGCCTGAGATCTGAGGACACCGCCGTGTACTACTGCGCCCC
TTACGACGCCGACTACGCCATGGATTATTGGGGCCAGGGCACCCTGGTCACCGTGTCCT
CTGCTTCTACCAAGGGACCCAGCGTGTTCCCTCTGGCTCCTTCCAGCAAGTCTACCTCTG
GCGGAACAGCTGCTCTGGGCTGCCTGGTCAAGGACTACTTTCCTGAGCCTGTGACCGTG
TCTTGGAACTCTGGCGCTCTGACATCCGGCGTGCACACATTTCCAGCTGTGCTGCAGTCC
TCCGGCCTGTACTCTCTGTCCTCTGTCGTGACCGTGCCTTCCTCTAGCCTGGGCACCCAG
ACCTACATCTGCAATGTGAACCACAAGCCTTCCAACACCAAGGTGGACAAGAAGGTGG
AACCCAAGTCCTGCGACAAGACCCACACCTGTCCTCCATGTCCTGCTCCAGAACTGCTC
GGCGGACCTTCCGTGTTCCTGTTTCCTCCAAAGCCTAAGGACACCCTGATGATCTCTCG
ACCCCTGAAGTGACCTGCGTGGTGGTGGATGTGTCTCACGAGGACCCAGAAGTGAAGTT
CAATTGGTACGTGGACGGCGTGGAAGTGCACAACGCCAAGACCAAGCCTAGAGAGGAA
CAGTACGCCAGCACCTACAGAGTGGTGTCCGTGCTGACAGTGCTGCACCAGGATTGGCT
GAACGGCAAAGAGTACAAGTGCAAGGTGTCCAACAAGGCCCTGCCTGCTCCTATCGAA
AAGACCATCAGCAAGGCCAAGGGCCAGCCTAGAGAACCCCAGGTTTACACCTTGCCTC
CATCTCGGGACGAGCTGACCAAGAACCAGGTGTCCCTGACCTGTCTCGTGAAGGGCTTC
TACCCCTCCGACATCGCCGTGGAATGGGAGTCTAATGGCCAGCCAGAGAACAACTACA
AGACAACCCCTCCTGTGCTGGACTCCGACGGCTCATTCTTCCTGTACTCCAAGCTGACCG
TGGACAAGTCCAGATGGCAGCAGGGCAACGTGTTCTCCTGCTCCGTGATGCACGAGGCC
CTGCACAATCACTACACACAGAAGTCCCTGTCTCTGTCCCCTGGC (SEQ ID NO: 74)

Light chain of hzMWTx-001Var:
Protein sequence (Constant region indicated by italics):
DIQMTQSPSSLSASVGDRVTITCKASQDISNYLSWFQQKPGKAPKLLIYRANRLVEGVPS
RFSGSGSGTDFTLTISSLQPEDFATYFCLQYDEFPLTFGGGTKVEIK*RTVAAPSVFIFPPSD*
*EQLKSGTASVVCLLNNFYPREAKVQWKVDNALQSGNSQESVTEQDSKDSTYSLSSTLTLSKAD*
*YEKHKVYACEVTHQGLSSPVTKSFNRGEC* (SEQ ID NO: 75)

Nucleotide sequence:
GACATCCAGATGACCCAGTCTCCATCCTCTCTGTCCGCCTCTGTGGGCGACAGAGTGAC
CATCACATGCAAGGCCAGCCAGGACATCTCCAACTACCTGTCCTGGTTCCAGCAGAAGC
CTGGCAAGGCTCCCAAGCTGCTGATCTACAGAGCCAACAGACTGGTGGAAGGCGTGCC
CTCCAGATTCTCCGGATCTGGCTCTGGCACCGACTTTACCCTGACAATCTCCAGCCTGCA
GCCTGAGGACTTCGCTACCTACTTCTGCCTGCAATACGACGAGTTCCCTCTGACCTTTGG
CGGAGGCACCAAGGTGGAAATCAAGCGGACAGTGGCCGCTCCTTCCGTGTTCATCTTCC
CACCTTCCGACGAGCAGCTGAAGTCCGGCACAGCTTCTGTCGTGTGCCTGCTGAACAAC TABLE 3-continued Heavy chain and light chain sequences of anti-TMPRSS6 monoclonal
antibodies MWTx-001, MWTx-002, and MWTx-003, and humanized anti-
TMPRSS6 antibody variants hzMWTx-001Var, hzMWTx-002Var, and hzMWTx-003Var TTCTACCCTCGGGAAGCCAAGGTGCAGTGGAAGGTGGACAATGCCCTGCAGTCCGGCA
ACTCCCAAGAGTCTGTGACCGAGCAGGACTCCAAGGACAGCACCTACAGCCTGTCCTCC
ACACTGACCCTGTCCAAGGCCGACTACGAGAAGCACAAGGTGTACGCCTGCGAAGTGA
CCCATCAGGGCCTGTCTAGCCCTGTGACCAAGTCTTTCAACCGGGGCGAGTGT (SEQ ID
NO: 76)

hzMWTx-002Var
Heavy chain of hzMWTx-002Var:
Protein sequence (Constant region indicated by italics;
N297A mutation indicated by bold):
EVQLVQSGAEVKKPGASVKVSCKASGFNIKDYYIHWVRQATGQGLEWMGRIDPEDAE
SEYAPKFQGRVTITADTSTDTAYMELSSLRSEDTAVYYCTRGDSMMVTYFDYWGQGT
LVTVS*SASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAKTKPREEQAST
YRVVSVLTVLHQDWLNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLTVDKSRWQQGNVFS
CSVMHEALHNHYTQKSLSLSPG* (SEQ ID NO: 77)

Nucleotide sequence:
GAAGTGCAGCTGGTGCAATCTGGCGCCGAAGTGAAGAAACCTGGCGCCTCTGTGAAGG
TGTCCTGCAAGGCCTCTGGCTTCAACATCAAGGACTACTACATCCACTGGGTCCGACAG
GCTACCGGACAGGGACTTGAGTGGATGGGCAGAATCGACCCTGAGGACGCCGAGTCTG
AGTACGCCCCTAAGTTTCAGGGCAGAGTGACCATCACCGCCGACACCTCTACCGACACC
GCCTACATGGAACTGTCCAGCCTGAGATCTGAGGACACCGCCGTGTACTACTGCACCAG
AGGCGACTCCATGATGGTTACCTACTTCGACTACTGGGGCCAGGGCACCCTGGTCACAG
TTTCTTCCGCTTCCACCAAGGGACCCAGCGTGTTCCCTCTGGCTCCTTCCAGCAAGTCTA
CCTCTGGCGGAACAGCTGCTCTGGGCTGCCTGGTCAAGGATTACTTCCCTGAGCCTGTG
ACCGTGTCCTGGAACTCTGGCGCTCTGACATCCGGCGTGCACACCTTTCCAGCTGTGCTG
CAATCCTCCGGCCTGTACTCTCTGTCCTCCGTCGTGACCGTGCCTTCTAGCTCTCTGGGC
ACCCAGACCTACATCTGCAATGTGAACCACAAGCCTTCCAACACCAAGGTGGACAAGA
AGGTGGAACCCAAGTCCTGCGACAAGACCCACACCTGTCCTCCATGTCCTGCTCCAGAA
CTGCTCGGCGGACCTTCCGTGTTCCTGTTTCCTCCAAAGCCTAAGGACACCCTGATGATC
TCTCGGACCCCTGAAGTGACCTGCGTGGTGGTGGATGTGTCTCACGAGGACCCAGAAGT
GAAGTTCAATTGGTACGTGGACGGCGTGGAAGTGCACAACGCCAAGACCAAGCCTAGA
GAGGAACAGTACGCCTCCACCTACAGAGTGGTGTCCGTGCTGACAGTGCTGCACCAGG
ATTGGCTGAACGGCAAAGAGTACAAGTGCAAGGTGTCCAACAAGGCACTGCCCGCTCC
TATCGAAAAGACCATCTCCAAGGCCAAGGGCCAGCCTAGAGAACCCCAGGTTTACACC
TTGCCTCCATCTCGGGACGAGCTGACCAAGAACCAGGTGTCCCTGACCTGTCTCGTGAA
GGGCTTCTACCCCTCCGACATCGCCGTGGAATGGGAGTCTAATGGCCAGCCAGAGAACA
ACTACAAGACAACCCCTCCTGTGCTGGACTCCGACGGCTCATTCTTCCTGTACTCCAAGC
TGACCGTGGACAAGTCCAGATGGCAGCAGGGCAACGTGTTCTCCTGCTCCGTGATGCAC
GAGGCCCTGCACAATCACTACACACAGAAGTCTCTGTCCCTGTCTCCTGGC (SEQ ID NO:
78)

Light chain of hzMWTx-002Var:
Protein sequence (Constant region indicated by italics):
DIQMTQSPSSLSASVGDRVTITCKASQDVSTAVAWYQQKPGKAPKLLIYWAFTRHTGV
PSRFSGSGSGTDYALTISSLQPEDFATYYCQQHYRSPWTFGGGTKVEIKR*TVAAPSVFIFP
PSDEQLKSGTASVVCLLNNFYPREAKVQWKVDNALQSGNSQESVTEQDSKDSTYSLSSTLTLS
KADYEKHKVYACEVTHQGLSSPVTKSFNRGEC* (SEQ ID NO: 79)

Nucleotide sequence:
GACATCCAGATGACCCAGTCTCCATCCTCTCTGTCCGCCTCTGTGGGCGACAGAGTGAC
CATCACATGCAAGGCCTCTCAGGACGTGTCCACCGCCGTTGCTTGGTATCAGCAGAAGC
CTGGCAAGGCCCCTAAGCTGCTGATCTACTGGGCCTTCACCAGACACACCGGCGTGCCC
TCTAGGTTCTCCGGCTCTGGCTCTGGCACCGATTACGCTCTGACAATCTCCAGCCTGCAG
CCTGAGGACTTCGCCACCTACTACTGCCAGCAGCACTACAGAAGCCCCTGGACATTTGG
CGGAGGCACCAAGGTGGAAATCAAGCGGACAGTGGCCGCTCCTTCCGTGTTCATCTTCC
CACCTTCCGACGAGCAGCTGAAGTCCGGCACAGCTTCTGTCGTGTGCCTGCTGAACAAC
TTCTACCCTCGGGAAGCCAAGGTGCAGTGGAAGGTGGACAATGCCCTGCAGTCCGGCA
ACTCCCAAGAGTCTGTGACCGAGCAGGACTCCAAGGACAGCACCTACAGCCTGTCCTCC
ACACTGACCCTGTCCAAGGCCGACTACGAGAAGCACAAGGTGTACGCCTGCGAAGTGA
CCCATCAGGGCCTGTCTAGCCCTGTGACCAAGTCTTTCAACCGGGGCGAGTGT (SEQ ID
NO: 80)

hzMWTx-003Var
Heavy chain of hzMWTx-003Var:
Protein sequence (Constant region indicated by italics;
LALA mutation indicated by bold):
QVQLVQSGAEVKKPGASVKVSCKASGFNIEDYYMHWVRQAPGQRLEWMGRIDPEDA
ETTYSPKFQGRVTIIPDTSANTAYMELSSLRSEDTAVYCARSIYLDPMDYWGQGTLVT
VS*SASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPEAAGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSREEMTKNQVS*

TABLE 3-continued

Heavy chain and light chain sequences of anti-TMPRSS6 monoclonal
antibodies MWTx-001, MWTx-002, and MWTx-003, and humanized anti-
TMPRSS6 antibody variants hzMWTx-001Var, hzMWTx-002Var, and hzMWTx-003Var

*LTCLVKGFYPSDIAVEWESNGQPENNYKTTPPVLDSDGSFFLYSKLTVDKSRWQQGNVFSCS*
*VMHEALHNHYTQKSLSLSPG* (SEQ ID NO: 81)

Nucleotide sequence:
CAGGTGCAGCTGGTGCAGTCTGGCGCCGAAGTGAAAAAGCCTGGCGCCTCTGTGAAGG
TGTCCTGCAAGGCCTCTGGCTTCAACATCGAGGACTACTACATGCACTGGGTCCGACAG
GCCCCTGGCCAGAGATTGGAATGGATGGGCAGAATCGACCCCGAGGACGCCGAGACAA
CCTACTCTCCTAAGTTCCAGGGCCGCGTGACAATCATCCCTGACACCTCTGCCAACACC
GCCTACATGGAACTGTCCAGCCTGAGATCTGAGGACACCGCCGTGTACTACTGCGCCCG
GTCTATCTACCTGGACCCTATGGACTATTGGGGCCAGGGCACCCTGGTCACAGTGTCCT
CTGCTTCTACCAAGGGACCCAGCGTGTTCCCTCTGGCTCCTTCCAGCAAGTCTACCTCTG
GCGGAACAGCTGCTCTGGGCTGCCTGGTCAAGGACTACTTTCCAGAGCCTGTGACCGTG
TCCTGGAACTCTGGCGCTCTGACATCTGGCGTGCACACCTTTCCAGCTGTGCTGCAGTCC
TCCGGCCTGTACTCTCTGTCCTCTGTCGTGACCGTGCCTTCCAGCTCTCTGGGAACCCAG
ACCTACATCTGCAATGTGAACCACAAGCCTTCCAACACCAAGGTGGACAAGAAGGTGG
AACCCAAGTCCTGCGACAAGACCCACACCTGTCCTCCATGTCCTGCTCCAGAAGCTGCT
GGCGGCCCTTCCGTGTTTCTGTTCCCTCCAAAGCCTAAGGACACCCTGATGATCTCTCGG
ACCCCTGAAGTGACCTGCGTGGTGGTGGATGTGTCTCACGAGGACCCAGAAGTGAAGTT
CAATTGGTACGTGGACGGCGTGGAAGTGCACAACGCCAAGACCAAGCCTAGAGAGGAA
CAGTACAACTCCACCTACAGAGTGGTGTCCGTGCTGACCGTGCTGCACCAGGATTGGCT
GAACGGCAAAGAGTACAAGTGCAAGGTGTCCAACAAGGCACTGCCCGCTCCTATCGAA
AAGACCATCTCCAAGGCCAAGGGCCAGCCTAGGGAACCCCAGGTTTACACCCTGCCTCC
AAGCCGGGAAGAGATGACCAAGAACCAGGTGTCCCTGACCTGCCTCGTGAAGGGCTTC
TACCCTTCCGACATCGCCGTGGAATGGGAGAGCAATGGCCAGCCAGAGAACAACTACA
AGACAACCCCTCCTGTGCTGGACTCCGACGGCTCATTCTTCCTGTACTCCAAGCTGACA
GTGGACAAGTCCAGATGGCAGCAGGGCAACGTGTTCTCCTGCTCCGTGATGCACGAGGC
CCTGCACAATCACTACACACAGAAGTCCCTGTCTCTGTCCCCTGGC (SEQ ID NO: 82)

Light chain of hzMWTx-003Var:
Protein sequence (Constant region indicated by italics):
DIQMTQSPKSLSASVGDRVTITCRASQDVTTALAWYQQKPGQSPKLLIYWATTRHSGV
PSRFSGSGSGTDFTLTISSLQPEDFATYYCQQHYSTPYTFGQGTKLEIK*RTVAAPSVFIFPP*
*SDEQLKSGTASVVCLLNNFYPREAKVQWKVDNALQSGNSQESVTEQDSKDSTYSLSSTLTLSK*
*ADYEKHKVYACEVTHQGLSSPVTKSFNRGEC* (SEQ ID NO: 83)

Nucleotide sequence:
GACATCCAGATGACCCAGTCTCCAAAGTCTCTGTCCGCCTCCGTGGGCGACAGAGTGAC
CATCACCTGTAGAGCCTCTCAGGACGTGACCACCGCTCTGGCTTGGTATCAGCAGAAGC
CTGGCCAGTCTCCTAAGCTGCTGATCTACTGGGCCACCACCAGACACTCTGGCGTGCCC
TCTAGATTCTCCGGCTCTGGCTCTGGCACCGACTTTACCCTGACAATCTCCAGCCTGCAG
CCTGAGGACTTCGCCACCTACTACTGCCAGCAGCACTACAGCACCCCTTACACCTTTGG
CCAGGGCACCAAGCTGGAAATCAAGCGGACAGTGGCCGCTCCTTCCGTGTTCATCTTCC
CACCTTCCGACGAGCAGCTGAAGTCCGGCACAGCTTCTGTCGTGTGCCTGCTGAACAAC
TTCTACCCTCGGGAAGCCAAGGTGCAGTGGAAGGTGGACAATGCCCTGCAGTCCGGCA
ACTCCCAAGAGTCTGTGACCGAGCAGGACTCCAAGGACAGCACCTACAGCCTGTCCTCC
ACACTGACCCTGTCCAAGGCCGACTACGAGAAGCACAAGGTGTACGCCTGCGAAGTGA
CCCATCAGGGCCTGTCTAGCCCTGTGACCAAGTCTTTCAACCGGGGCGAGTGT (SEQ ID
NO: 84)

Dose-Dependent Effects of Anti-TMPRSS6 Antibodies on HAMP Promoter Activity

Figure 2B:
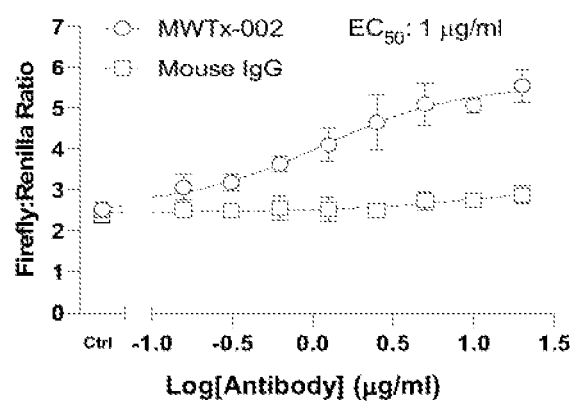
Figure 2C:
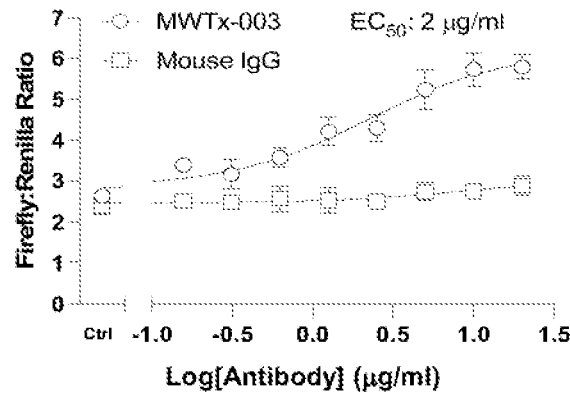
Figure 2D:
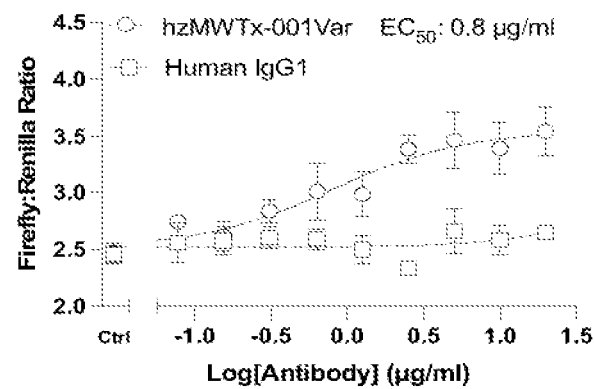
Figure 2E:
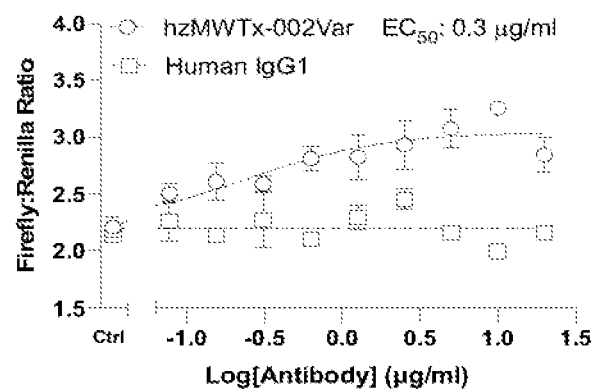
Figure 2F:
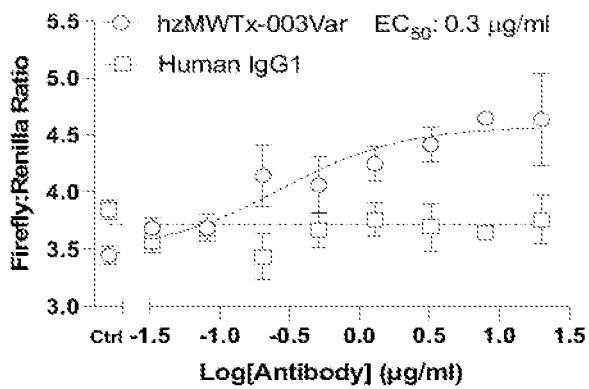

FIGS. 2A-2F show the results from using the HAMP-luciferase report assay described above to test MWTx-001, MWTx-002, MWTx-003 and their humanized variants hzMWTx-001Var, hzMWTx-002Var, hzMWTx-M003Var, respectively, at the indicated concentrations. Each of MWTx-001 (FIG. 2A), MWTx-002 (FIG. 2B), MWTx-003 (FIG. 2C) and humanized variants hzMWTx-001Var (FIG. 2D), hzMWTx-002Var (FIG. 2E), hzMWTx-003Var (FIG. 2F) increases HAMP promoter activity in a dose-dependent manner. The $EC_{50}$ for MWTx-001 was calculated to be 3 µg/ml (FIG. 2A). The $EC_{50}$ for MWTx-002 was calculated to be 1 µg/ml (FIG. 2B). The $EC_{50}$ for MWTx-003 was calculated to be 2 µg/ml (FIG. 2C). The $EC_{50}$ for hzMWTx-001Var was calculated to be 0.8 µg/ml (FIG. 2D). The $EC_{50}$ for hzMWTx-002Var was calculated to be 0.3 µg/ml (FIG. 2E). The $EC_{50}$ for hzMWTx-003Var was calculated to be 0.3 µg/ml (FIG. 2F).

Example 3. Binding Affinity of ANTI-TMPRSS6 Antibodies

The binding affinity of various anti-TMPRSS6 antibodies to human TMPRSS6 expressed on HEK293T cells was measured using three different methods: cell surface ELISA (FIGS. 3A-3C), FACS (FIGS. 3D-3F), and Bio-Layer Interferometry (FIGS. 3G-3M).

Anti-TMPRSS6 mAb Binding Affinity Measurement Using Cell Surface ELISA

Figure 3A:
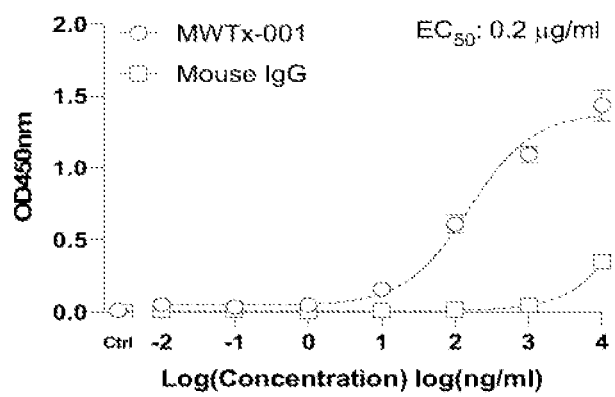
Figure 3B:
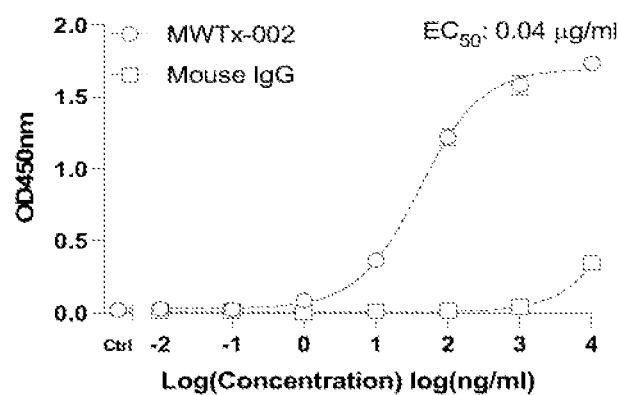
Figure 3C:
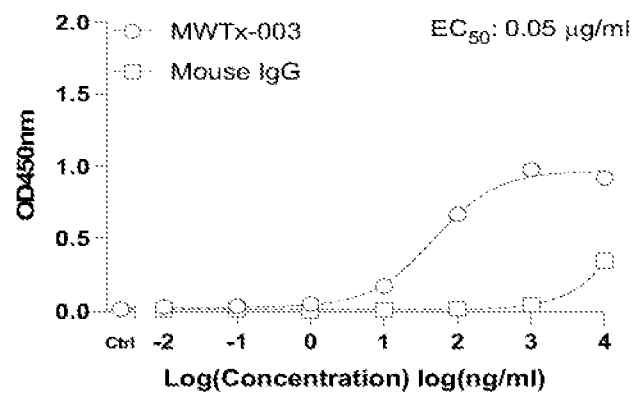

HEK293T cells stably expressing human TMPRSS6 (generated by LakePharma Inc as described above; SEQ ID NO: 97) were fixed with 4% paraformaldehyde (PFA), and washed with dPBS (Dulbeccos phosphate-buffered saline, Corning Cellgro) before incubation with various concentrations of anti-TMPRSS6 antibodies diluted in BSA medium (DMEM÷1% Pen/Strep+10 mM HEPES÷1 mg/ml BSA (Sigma-Aldrich). Purified mouse IgG was used as a control (Sigma-Aldrich). After incubation, cells were washed with BSA medium and then incubated with goat anti-mouse IgG conjugated with HRP as a 2° antibody (Invitrogen). At last, cells were washed with dPBS to remove unbound antibody and color developed with ELISA liquid substrate (Sigma-Aldrich), followed by stopping the reaction with addition of the same volume of ELISA liquid substrate of 1M $H_2SO_4$. Bound antibody was measured by absorbance at $OD_{450\ nm}$. Results for these assays are shown in FIGS. 3A-3C.

Anti-TMPRSS6 mAb Binding Affinity Measurement Using FACS

Figure 3D:
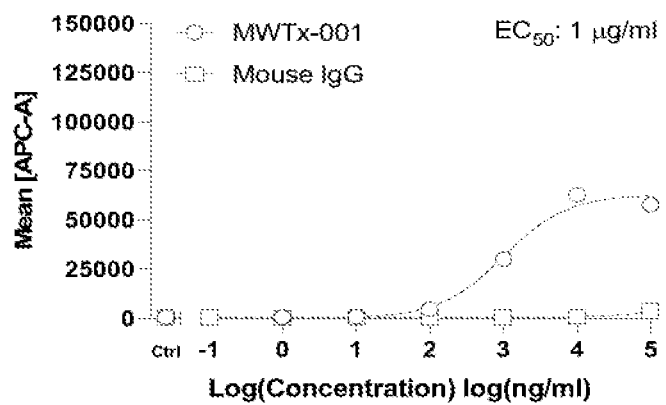
Figure 3E:
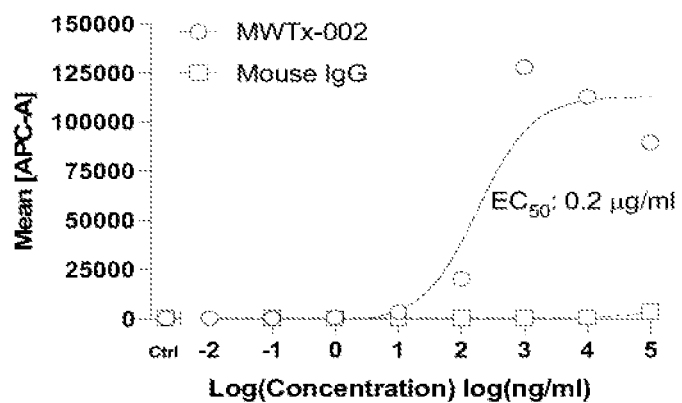
Figure 3F:
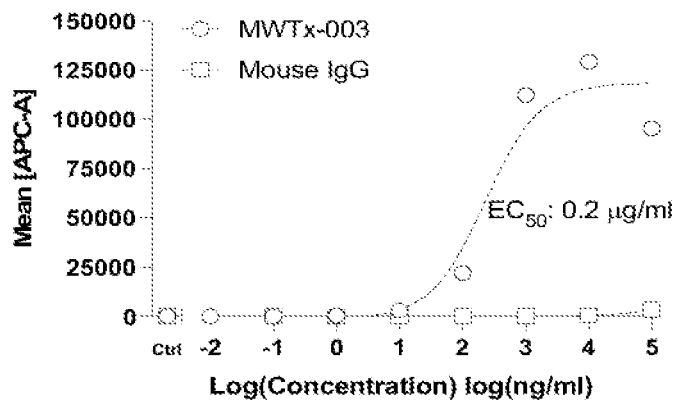
Figure 3G:
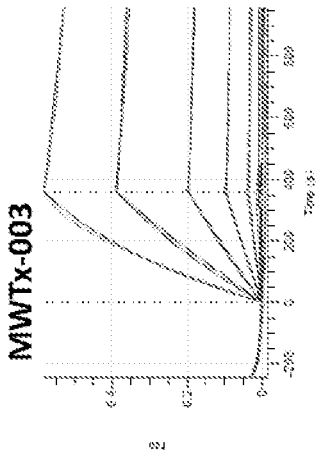
Figure 3H:
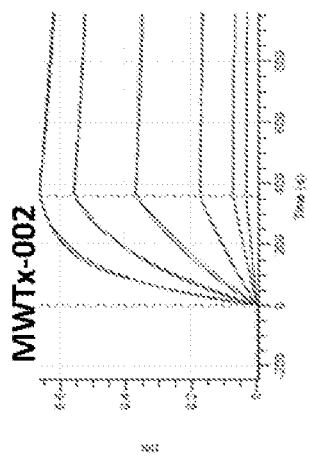
Figure 3I:
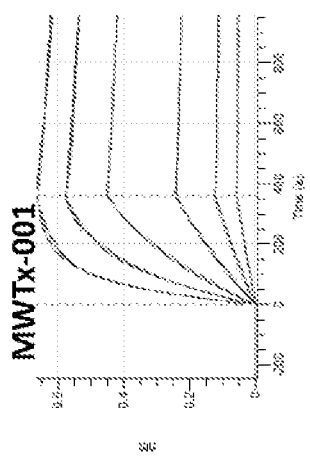
Figure 3J:
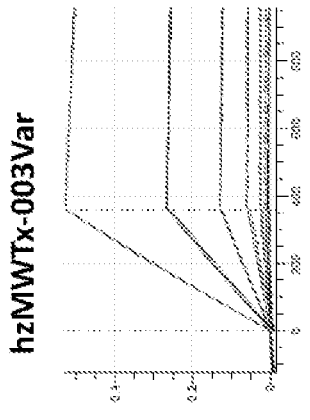
Figure 3K:
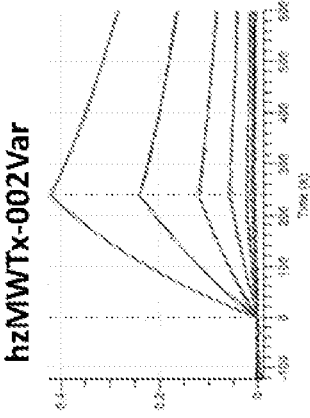
Figure 3L:
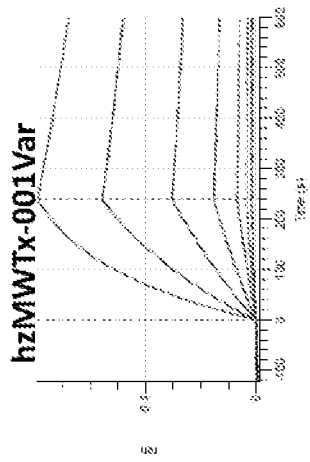

HEK293T cells stably expressing human TMPRSS6 were collected, and blocked with dPBS+3% BSA before incubation with various concentrations of anti-TMPRSS6 antibodies diluted in dPBS+3% BSA. Purified mouse IgG was used as a control. After incubation, cells were washed with dPBS and then incubated with goat anti-mouse IgG conjugated with APC as a 2° antibody (Jackson ImmunoResearch Inc). At last, cells were washed with dPBS to remove unbound antibody, re-suspended with dPBS+1 mM EDTA, and then subjected to FACS analysis using a NOVOCYTE® Flow Cytometer (ACEA Biosciences, Inc., San Diego CA). Bound antibody was determined by measuring mean APC intensity after excitation at 640 nm and measurement of emission (fluorescence) at 675 nm. Results for these assays are shown in FIGS. 3D-3F.

Anti-TMPRSS6 Antibody Affinity and Binding Kinetics Measurement Using Bio-Layer Interferometry Bio-Layer Interferometry technology was used for anti-TMPRSS6 antibody affinity measurement and binding kinetics determinations with Octet® RED96e system (Sartorius AG). Pre-hydrated Anti-Mouse IgG Fc Capture (AMC) biosensors (for MWTx-001, MWTx-002 and MWTx-003 anti-TMPRSS6 antibodies, FIGS. 3G-3I) or Anti-Human IgG Fc Capture (AHC) biosensors (for hzMWTx-001Var, hzMWTx-002Var and hzMWTx-003Var anti-TMPRSS6 antibodies, FIGS. 3J-3L) were first equilibrated in 1×KB (Kinetic Buffer, 1×PBS pH 7.4+0.02% Tween-20+0.1% BSA) for 120 sec for the first baseline, followed by loading with 10 mg/ml anti-TMPRSS6 antibody (MWTx-001, FIG. 3G; MWTx-002, FIG. 3H; MWTx-003, FIG. 3I; hzMWTx-001Var, FIG. 3J; hzMWTx-002Var, FIG. 3K; hzMWTx-003Var, FIG. 3L) onto AMC or AHC biosensors for 240 sec. Then, the second baseline signal was established for 120 sec before association with various concentrations of human ecto-TMPRSS6-FLAG (SEQ ID NO: 102) (generated in house by fusing extracellular domain of human TMPRSS6 with a FLAG-tag at C-terminus) for 240 sec. At last, analyte was dissociated in 1×KB for 360 sec. Data analysis was done using Octet Data Analysis HT Software. KD, $k_{on}$, $k_{off}$ and $R^2$ were summarized in FIG. 3M.

Example 4: Cross-Reactivity: Anti-TMPRSS6 Antibody Binding to Human TMPRSS6 and Non-Human TMPRSS6

Cross-Reactivity Determination by FACS

Selected anti-TMPRSS6 antibodies were tested to determine whether any are capable of binding to TMPRSS6 from mouse and/or cynomolgus monkey. HEK293T cells stably expressing human TMPRSS6 (HuTMPRSS6-$(His)_6$) (generated by LakePharma Inc as described above), HEK293T cells stably expressing mouse TMPRSS6 (MoTMPRSS6-$(His)_6$) (SEQ ID NO: 98) (generated by LakePharma Inc as described above) and HEK293T cells transiently expressing cynomolgus monkey TMPRSS6 (CynoTMPRSS6-$(His)_6$) (SEQ ID NO: 99) (generated in house) were collected. HEK293T cells stably expressing human TMPRSS6 were used as a positive control and HEK293T cells were used as a negative control (as described above). Cells were blocked with dPBS+3% BSA before incubation with anti-TMPRSS6 antibodies diluted in dPBS+3% BSA. After incubation, cells were washed with dPBS and followed by another incubation with goat anti-mouse IgG conjugated with AlexaFluor-488 as a 2° antibody (Invitrogen). At last, cells were washed with dPBS to remove unbound antibody, re-suspended with dPBS+1 mM EDTA, and then subjected to FACS analysis using a NOVOCYTE® Flow Cytometer (ACEA Biosciences, Inc., San Diego CA). Bound antibody was determined by excitation at 488 nm and measurement of emission (FITC-A) at 530 nm. Results for these assays are shown in histogram plots in FIGS. 4A-4I. Cross-reactivity with mouse TMPRSS6 was observed for MWTx-001 (FIG. 4D) and MWTx-003 (FIG. 4F), whereas MWTx-002 (FIG. 4E) did not show detectable cross-reactivity with mouse TMPRSS6. Cross-reactivity with cynomolgus monkey TMPRSS6 was observed for MWTx-001 (FIG. 4G), MWTx-002 (FIG. 4H) and MWTx-003 (FIG. 4I).

Cross-Reactivity Determination by Cell Surface ELISA

HEK293T cells stably expressing mouse TMPRSS6 (generated by LakePharma Inc as described above, FIGS. 4J, 4L, 4N, 4P, 4R, 4T) or cynomolgus monkey (generated in house as described above, FIGS. 4K, 4M, 4O, 4Q, 4S, 4U) were fixed with methanol (100%), and washed with dPBS (Dulbecco's phosphate-buffered saline, Corning Cellgro) before incubation with various concentrations of anti-TMPRSS6 antibodies and their humanized variants diluted in BSA medium (DMEM+1% Pen/Strep+10 mM HEPES+1 mg/ml BSA (Sigma-Aldrich)). Purified mouse IgG (FIGS. 4J-4O) or Human IgG1 (FIGS. 4P-4U) was used as a control. After incubation, cells were washed with BSA medium and then incubated with goat anti-mouse (Invitrogen, FIGS. 4J-4O) or anti-human (Millipore, FIGS. 4P-4U) IgG conjugated with HRP as a 2° antibody. Finally, cells were washed with dPBS to remove unbound antibody and color developed with ELISA liquid substrate (Sigma-Aldrich), followed by stopping the reaction with addition of the same volume of ELISA liquid substrate of 1M $H_2SO_4$. Bound antibody was measured by absorbance at $OD_{450\ nm}$. Results for these assays are shown in FIGS. 4J-4U. Cross-reactivity with mouse TMPRSS6 was observed for MWTx-001 (FIG. 4J) and MWTx-003 (FIG. 4N) anti-TMPRSS6 antibodies and their humanized variants hzMWTx-001Var (FIG. 4P), and hzMWTx-003Var (FIG. 4T) anti-TMPRSS6 antibodies, whereas MWTx-002 (FIG. 4L) anti-TMPRSS6 antibody or its humanized variant hzMWTx-002Var (FIG. 4R) anti-TMPRSS6 antibody did not show detectable cross-reactivity with mouse TMPRSS6. Cross-reactivity with cynomolgus monkey TMPRSS6 was observed for MWTx-001 (FIG. 4K), MWTx-002 (FIG. 4M), and MWTx-003 (FIG. 4O) anti-TMPRSS6 antibodies and their humanized variants hzMWTx-001Var (FIG. 4Q), hzMWTx-002Var (FIG. 4S), and hzMWTx-003Var (FIG. 4U) anti-TMPRSS6 antibodies.

Example 5: Target Specificity: Anti-TMPRSS6 Anybody Binding to Homologous Matriptases To determine if anti-TMPRSS6 antibodies bind to homologous matriptases, HEK293T cells over-expressing matriptase (ST14) (SEQ ID NO: 100) (FIGS. 5B, 5E, 5H, 5K, 5N, 5Q), and HEK293T cells over-expressing matriptase-3 (TMPRSS7) (SEQ ID NO: 101) (FIGS. 5C, 5F, 5I, 5L, 5O, 5R) were collected (generated in house). HEK293T cells stably expressing human TMPRSS6 (matriptase-2)(SEQ ID NO:97) (generated by LakePharma Inc as described above, FIGS. 5A, 5D, 5G, 5J, 5M, 5P) were used as a positive control and HEK293T cells (FIGS.

5A-5R) were used as a negative control (as described above). Cells were blocked and permeabilized with dPBS+ 3% BSA+0.1% Tween-20 before incubation with various anti-TMPRSS6 antibodies diluted in dPBS+3% BSA+0.1% Tween-20. Cells were incubated with anti-TMPRSS6 antibodies and their humanized variants at a concentration of roughly 1 μg/ml for 1 hr. After incubation, cells were washed with dPBS and incubated with goat anti-mouse IgG conjugated with AlexaFluor-488 (invitrogen, FIGS. 5A-5I) or goat anti-human IgG conjugated with Allophycocyanin (APC) (Jackson Immuno Research, FIGS. 5J-5R) as a 2° antibody. At last, cells were washed with dPBS and re-suspended with dPBS+1 mM EDTA, and then subjected to FACS analysis using a NOVOCYTE® Flow Cytometer. Bound antibody was determined by excitation at 488 nm and measurement of emission (FITC-A) at 530 nm (FIGS. 5A-5I) or by excitation at 640 nm and measurement of emission (APC-A) at 675 nm (FIGS. 5J-5R). Results for these assays are shown in histogram plots in FIGS. 5A-5R. All of the antibodies showed binding to human TMPRSS6 (matriptase-2) (FIGS. 5A, 5D, 5G, 5J, 5M, 5P) and none of the antibodies showed binding to homologous matriptases ST14 (FIGS. 5B, 5E, 5H, 5K, 5N, 5Q) or TMPRSS7 (FIGS. 5C, 5F, 5I, 5L, 5O, 5R). MWTx-001 anti-TMPRSS6 antibody and its humanized variant hzMWTx-001Var anti-TMPRSS6 antibody showed binding to human TMPRSS6 (FIGS. 5A, 5J) and did not show binding to matriptase (ST14) (FIGS. 5B, 5K) or matriptase-3 (TMPRSS7) (FIGS. 5C, 5L). MWTx-002 anti-TMPRSS6 antibody and its humanized variant hzMWTx-002Var anti-TMPRSS6 antibody showed binding to human TMPRSS6 (matriptase-2) (FIGS. 5D, 5M) and did not show binding to matriptase (ST14) (FIGS. 5E, 5N) or matriptase-3 (TMPRSS7) (FIGS. 5F, 5O). MWTx-003 anti-TMPRSS6 antibody and its humanized variant hzMWTx-003Var anti-TMPRSS6 antibody showed binding to human TMPRSS6 (matriptase-2) (FIGS. 5G, 5P) and did not show binding to matriptase (ST14) (FIGS. 5H, 5Q) or matriptase-3 (TMPRSS7) (FIGS. 5I, 5R).

Example 6. Treatment with Anti-TMPRSS6 Antibodies in a Mouse Pharmacodynamic Model In order to study the in vivo pharmacodynamic responses of anti-TMPRSS6 antibodies, 2-10 mg/kg of MWTx-003 anti-TMPRSS6 antibody (FIGS. 6A-6B, 6D-6E, 6G-6H, 6J-6K) or its humanized variant hzMWTx-003Var anti-TMPRSS6 antibody (FIGS. 6C, 6F, 6I, 6L) was injected intraperitoneally into wildtype C57BL/6J mouse. Mouse IgG2b (BioXcell, FIGS. 6A-6B, 6D-6E, 6G-6H, 6J-6K) or human IgG1 (BioXcell, FIGS. 6C, 6F, 6I, 6L) was used as isotype control. 20 hours post injection, 50 μg of GFP-TMPRSS6 plasmid DNA (generated in house by inserting human TMPRSS6 into a GFP vector) was delivered into each mouse by hydrodynamic tail vein injection. 44 hours post hydrodynamic injection, mice were euthanized, liver tissues and blood were collected. Liver RNA was purified by EZgene Total RNA Purification Plus from Biomiga (San Diego, CA) according to the manufacturer's instructions. Mouse serum was obtained by centrifugation of whole blood at 1500×g, 10 min.

Effects of Treatment with Anti-TMPRSS6 Antibodies on Serum Iron

Serum iron was measured by a chromogenic assay developed in house (FIGS. 6A-6C). Briefly, mouse serum or iron standard (31-500 μg/dL) was mixed with Mixed Acid Solution (0.6M Trichloroacetic acid, 0.4M Thioglycolic sodium, 1M HCl) by vertexing for 30 sec. The mixtures were incubated for 10 min at 37° C. before centrifugation at 10,000×g for 10 min followed by color development in Color Solution (1.5M Sodium Acetate, 0.5 mM Bathophenanthroline disulfonic salt). The absorbance was then read at $OD_{535\ nm}$. The serum iron concentration was calculated from linear iron standard curve. Treatment of 10 mg/kg MWTx-003 anti-TMPRSS6 antibody (FIGS. 6A-6B) and its humanized variant hzMWTx-003Var anti-TMPRSS6 antibody (FIG. 6C) significantly reduced serum iron.

Effects of Treatment with Anti-TMPRSS6 Antibodies on Serum Hepeidin

Serum hepcidin was measured by Hepcidin-Murine Compete ELISA kit purchased from Intrinsic Lifesciences (La Jolla, CA) according to the manufacturer's instructions (FIGS. 6D-6F). Briefly, diluted mouse serum or hepcidin standard was mixed with hepcidin biotin conjugate before adding to the plate coated with an anti-murine hepcidin antibody. Serum hepcidin or hepcidin standard competes with hepcidin biotin conjugate for binding to coated anti-hepcidin antibody. The bound hepcidin biotin conjugate was detected with streptavidin conjugated horseradish peroxidase (HRP), and color developed with TMB followed by stop solution. The absorbance was then read at $OD_{450\ nm}$. The data was analyzed with Graphpad Prism 8 using a four-parameter logistic (4-PL) curve-fit, and serum hepcidin concentration was interpolated. Hydrodynamic delivery of GFP-TMPRSS6 significantly reduced serum hepcidin level (FIG. 6D), whereas treatment with 10 mg/kg MWTx-003 anti-TMPRSS6 antibody (FIGS. 6D-6E) and its humanized variant hzMWTx-003Var anti-TMPRSS6 antibody (FIG. 6F) reversed the repression of hepcidin and significantly increased serum hepcidin level.

Effects of Treatment with Anti-TMPRSS6 Antibodies on Liver Hepeidin RNA

Liver hepcidin RNA was quantified by real-time qPCR (FIGS. 6G-6I). Briefly, cDNA was first synthesized from liver RNA using iScript Reverse Transcription Supermix (Bio-Rad) according to the manufacturer's instructions. Hepcidin transcripts were amplified with specific primers listed below in Table 4, and detected using SsoAdvanced™ Universal SYBR® Green Supermix (Bio-Rad) according to the manufacturer's instructions on Bio-Rad CFX96 qPCR instrument. Samples were analyzed in triplicate, and results are normalized to β-actin RNA levels (measured by transcription, amplification with primers listed in Table 4, and quantification as described above). Hydrodynamic delivery of GFP-TMPRSS6 significantly reduced liver hepcidin RNA (FIG. 6G). Treatment of 10 mg/kg MWTx-003 anti-TMPRSS6 antibody (FIGS. 6G-6H) and its humanized variant hzMWTx-003Var anti-TMPRSS6 antibody (FIG. 6I) reversed the repression of Hamp and significantly increased liver hepcidin RNA levels. The following primers were used for RNA quantification by real-time qPCR: Hepcidin forward primer: 5'-AAG CAG GGC AGA CAT TGC GAT-3' (SEQ ID NO: 85); Hepcidin is reverse primer: 5'-CAG GAT GTG GCT CTA GGC TAT-3' (SEQ ID NO: 86); β-actin forward primer: 5'-ACC CAC ACT GTG CCC ATC TA-3' (SEQ ID NO: 87); β-actin reverse primer: 5'-CAC GCT CGG TCA GGA TCT TC-3' (SEQ ID NO: 88).

Serum concentration of MWTx-003 anti-TMPRSS6 antibody or its humanized variant hzMWTx-003Var anti-TMPRSS6 antibody was quantified by cell surface ELISA developed in house (as described above, FIG. 6J-6L). Briefly, diluted mouse serum or anti-TMPRSS6 antibody standard were incubated with 100% methanol fixed HEK293T cells stably expressing human TMPRSS6

(HEK293T cells were used as background control). Bound MWTx-003 anti-TMPRSS6 antibody was detected with goat anti-mouse IgG conjugated with HRP, and bound hzMWTx-003Var anti-TMPRSS6 antibody was detected with goat anti-human IgG conjugated with HRP. Color was developed with TMB followed by stop solution. The absorbance was then read at $OD_{450\ nm}$. Samples were analyzed in triplicate, and results are normalized to HEK293T control. The data was analyzed with Graphpad Prism 8 using a four-parameter logistic (4-PL) curve-fit, and serum anti-TMPRSS6 antibody concentration was interpolated.

Example 7. In Vivo Efficacy of ANTI-TMPRSS6 Antibody Using Beta-Thalassemia Mouse Model In order to study in vivo efficacy of anti-TMPRSS6 antibody, a β-thalassemia mouse model (B6.129P2-Hbb-b1$^{tm1Unc}$ Hbb-b2$^{tm1Unc}$/J, JAX Stock No: 002683, The Jackson Laboratories, Bar Harbor ME) was chosen, herein referred to as Th3/+ mouse. 4-5 weeks old Th3/+ mice and their wildtype (WT) littermates were put on an iron sufficient diet (Teklad TD.80394) and Th3/+ mice were treated with 10 mg/kg MWTx-003 anti-TMPRSS6 antibody or mouse IgG2b isotype control every three days for 4 weeks, while WT littermates did not receive treatments. At the end of the treatment course, mice were euthanized, and spleen, liver, femur and blood samples were collected. Liver total RNA was purified, and serum was collected as described above.
Effects on Blood Counts, Splenomegaly, Serum Iron, Serum Hepcidin, Liver Hepcidin RNA Complete Blood Count (CBC) was performed by VETSCAN HM5 automated hematology analyzer (FIGS. 7A-7D). MWTx-003 anti-TMPRSS6 antibody treatment significantly increased Red Blood Count (RBC, FIG. 7A) and hematocrit (HCT, FIG. 7C), and reduced Red Cell Distribution Width (RDW, FIG. 7D), but had no apparent effect on Hemoglobin (HGB, FIG. 7B) in Th3/+ mice.

Figure 7A:
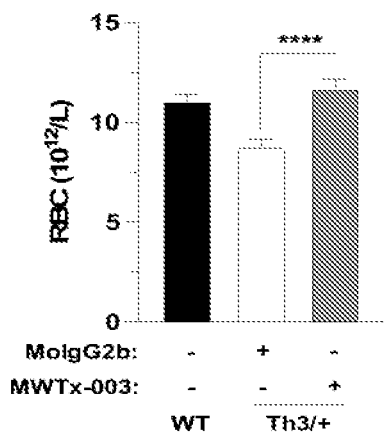
FIGS. 7A-7R show in vivo efficacy of anti-TMPRSS6 antibody using a β-thalassemia mouse model.
Figure 7B:
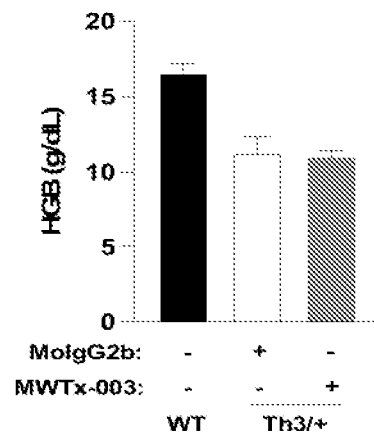
Figure 7C:
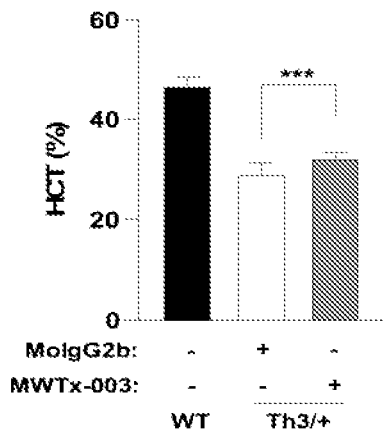
Figure 7D:
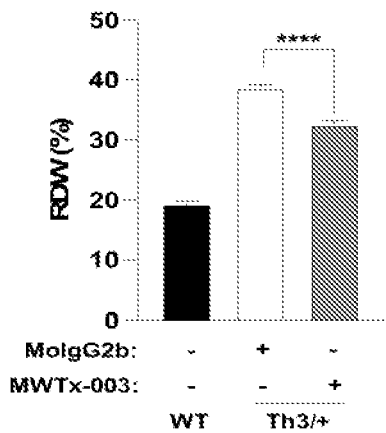
Figure 7E:
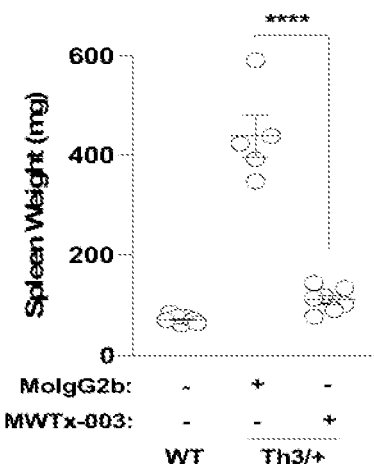
FIG. 7E shows effect of MWTx-003 anti-TMPRSS6 antibody on spleen weight using Th3/+ mice.

Spleen weight was measured, and MWTx-003 anti-TMPRSS6 antibody treatment significantly reduced splenomegaly for Th3/+ mice (FIG. 7E).

Figure 7F:
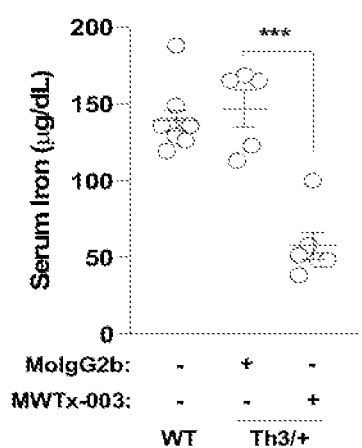
FIG. 7F shows effect of MWTx-003 anti-TMPRSS6 antibody on serum iron using Th3/+ mice.
Figure 7G:
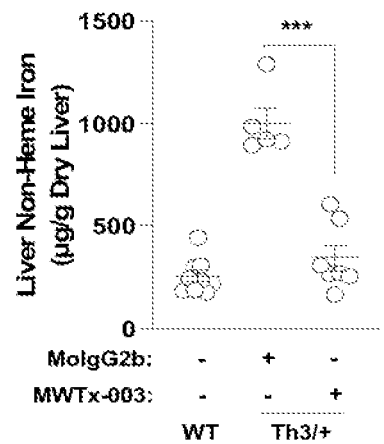
FIG. 7G shows effect of MWTx-003 anti-TMPRSS6 antibody on liver non-heme iron using Th3/+ mice.

Serum iron was measured as described above. Treatment with MWTx-003 anti-TMPRSS6 antibody significantly reduced serum iron (FIG. 7F). Liver non-heme iron was measured using a similar chromogenic assay (FIG. 7G). Briefly, minced small liver tissue was dried at 65° C. for overnight followed by digestion with mixed acid (3M HCl, 10% Trichloroacetic acid) at 65° C. for 20 hr. Then, digestion supernatant was collected for color development in Color Solution (1.5M sodium acetate, 0.5 mM bathophenanthroline disulfonic salt). The absorbance was then read at $OD_{535\ nm}$. Treatment with MWTx-003 anti-TMPRSS6 antibody significantly reduced liver non-heme iron (FIG. 7G).

Figure 7H:
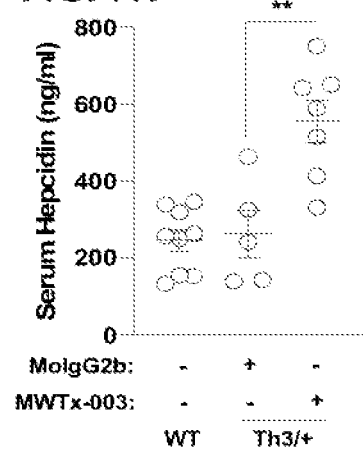
FIG. 7H shows effect of MWTx-003 anti-TMPRSS6 antibody on serum hepcidin using Th3/+ mice.

Serum hepcidin was measured by Hepcidin-Murine Compete ELISA kit as described above. Treatment with MWTx-003 anti-TMPRSS6 antibody significantly increased serum hepcidin (FIG. 7H).

Figure 7I:
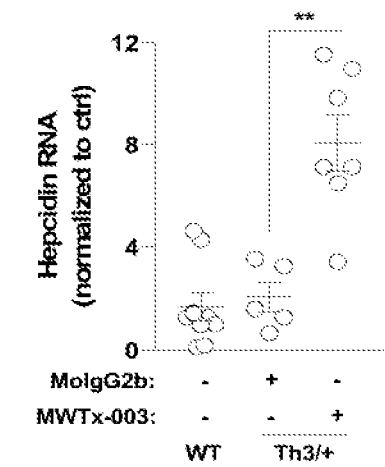
FIG. 7I shows effect of MWTx-003 anti-TMPRSS6 antibody on liver hepcidin RNA using Th3/+ mice.

Liver hepcidin RNA was quantified by real-time qPCR as described above. Treatment with MWTx-003 anti-TMPRSS6 antibody significantly increased liver hepcidin RNA (FIG. 7I).

Figure 7J:
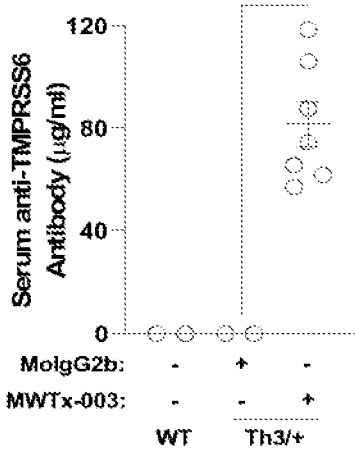
FIG. 7J shows serum concentration of MWTx-003 anti-TMPRSS6 antibody using Th3/+ mice.
Figure 7Q:
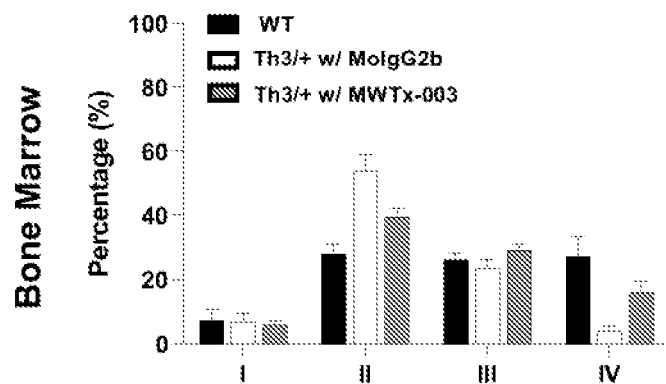
Figure 7R:
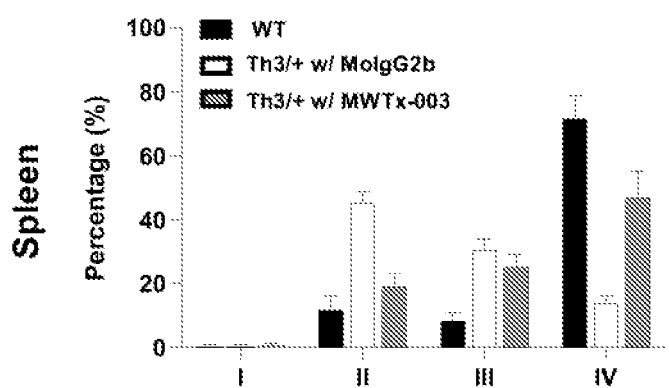

Serum concentration of MWTx-003 anti-TMPRSS6 antibody was quantified by cell surface ELISA developed in-house as described above (FIG. 7J).
Effects on Erythropoiesis In order to study effects of MWTx-003 anti-TMPRSS6 antibody on erythropoiesis in Th3/+ mice, bone marrow was harvested from femur (see FIGS. 7K-7M) and splenocytes were harvested from spleen (see FIGS. 7N-7P), and analyzed. Harvested cells were blocked with rat anti-mouse CD16/CD32 (BD Biosciences) for 15 min followed by staining with rat anti-mouse TER119 conjugated with FITC (BD Biosciences) and rat anti-mouse CD44 conjugated with APC (Invitrogen) for 30 min on ice. Washed cells were stained with the viability marker 7-AAD (BD Biosciences) for 10 min on ice before FACS analysis using a NOVOCYTE® Flow Cytometer. Ter119$^+$, 7-ADD$^-$ cells were selected, and density plots were graphed with anti-mouse CD44 over cell size (FSC-H). Plots were analyzed to identify cell types (cell clusters) and determine the abundance of each type (cluster) Representative plots in FIGS. 7K-7P show that four distinct cell clusters were distinguished from top to bottom, corresponding to successive stages in erythroid differentiation and identified as: basophilic erythroblasts (cluster I), polychromatic erythroblasts (cluster II), orthochromatic erythroblasts and nonnucleated reticulocytes (cluster III) and mature red cells (cluster IV). Percentage (%) value of each cluster in a sample was calculated as a measure of the abundance of cell type(s) in that cluster, as shown in FIGS. 7K-7P. The % value for each cell cluster (I), (II), (III), (IV) was calculated for each sample (bone marrow, spleen) from each animal in each treatment course, as follows: WT (no treatment) N=9; disease model Th3/+ mouse treated with IgG2b isotype control (Th3+w/MoIgG2b), N=5; disease model Th3/+ mouse treated with MWTx-003 anti-TMPRSS6 antibody (Th3+w/MWTx-003), N=7 and average values were then calculated. On average, populations of basophilic erythroblasts (I) showed a 7.58% (Th3+w/MoIgG2b) to 6.52% (Th3+w/MWTx-003) shift (7.96% for WT), polychromatic erythroblasts (II) showed a 54.20% (Th3+w/MoIgG2b) to 40.01% (Th3+w/MWTx-003) shift (28.53% for WT), orthochromatic erythroblasts and nonnucleated reticulocytes (III) showed a 24.06% (Th3+w/MoIgG2b) to 29.73% (Th3+w/MWTx-003) shift (26.67% for WT) and mature red cells (IV) showed a 4.54% (Th3+w/MoIgG2b) to 16.44% shift (27.66% for WT) in bone marrow cells after four weeks. On average, populations of basophilic erythroblasts (I) showed a 0.71% (Th3+w/MoIgG2b) to 0.91% (Th3+w/MWTx-003) shift (0.46% for WT), polychromatic erythroblasts (II) showed a 45.76% (Th3+w/MoIgG2b) to 19.25% (Th3+w/MWTx-003) shift (12.23% for WT), orthochromatic erythroblasts and nonnucleated reticulocytes (III) showed a 31.16% (Th3+w/MoIgG2b) to 28.72% (Th3+w/MWTx-003) shift (8.67% for WT) and a mature red cells (IV) showed a 14.13% (Th3+w/MoIgG2b) to 44.38% (Th3+w/MWTx-003) shift (72.17% for WT) in spleen after found weeks. These results are shown in a bar graph in FIG. 7Q for bone marrow, and FIG. 7R for spleen.

In Th3/+ mice, treatment with MWTx-003 anti-TMPRSS6 antibody improved ineffective erythropoiesis, with a significant proportion of erythroblasts differentiated and matured into red blood cells.

Example 8. ANTI-TMPRSS6 Antibodies Epitope Binning

OCTET® RED96e was used for epitope binning of MWTx-001 (FIG. 8A), MWTx-002 (FIG. 8B) and MWTx-003 (FIG. 8C) anti-TMPRSS6 antibodies. First, ecto-TMPRSS6-FLAG (as described above) was labelled with biotin by Biotinylation Kit (Abcam). Pre-hydrated streptavidin (SA) biosensors were equilibrated in 1×KB (as described above) for 60 sec for the first baseline, followed by loading with 10 mg/mL of biotinylated ecto-TMPRSS6-FLAG onto the SA biosensors for 300 sec. Then, the second baseline signal was established for 60 sec before saturation with 50 mg/ml of antibody (MWTx-001, FIG. 8A; MWTx-002, FIG. 8B; MWTx-003, FIG. 8C) in 1×KB for 600 sec. At last, the third baseline signal was established for 60 sec before competition with 50 µg/ml of MWTx-001, MWTx-002 or MWTx-003 in 1×KB for 300 sec. MWTx-001 anti-TMPRSS6 antibody binding towards ecto-TMPRSS6-FLAG was not competed with MWTx-002 anti-TMPRSS6 antibody or MWTx-003 anti-TMPRSS6 antibody (FIG. 8A). MWTx-002 anti-TMPRSS6 antibody binding towards ecto-TMPRSS6-FLAG was not competed with MWTx-001 anti-TMPRSS6 antibody but was competed with MWTx-003 anti-TMPRSS6 antibody (FIG. 8B). MWTx-003 anti-TMPRSS6 antibody binding towards ecto-TMPRSS6-FLAG was not competed with MWTx-001 anti-TMPRSS6 antibody but was competed with MWTx-002 anti-TMPRSS6 antibody (FIG. 8C). Data analysis was done using Octet Data Analysis HT Software. Association signals were summarized in FIG. 8D.

---

SEQUENCE LISTING

```
<160> NUMBER OF SEQ ID NOS: 102

<210> SEQ ID NO 1
<211> LENGTH: 118
<212> TYPE: PRT
<213> ORGANISM: Mus musculus

<400> SEQUENCE: 1

Gln Val Gln Leu Gln Gln Pro Gly Ala Glu Leu Ala Lys Pro Gly Ala
1               5                   10                  15

Ser Val Lys Met Ser Cys Lys Ala Ser Gly Tyr Thr Phe Thr Ser Tyr
            20                  25                  30

Trp Ile Thr Trp Val Lys Gln Arg Pro Gly Gln Asp Leu Glu Trp Ile
        35                  40                  45

Gly Asn Ile Tyr Pro Gly Ser Gly Ser Thr Tyr Tyr Asn Glu Lys Phe
    50                  55                  60

Lys Ser Lys Ala Thr Leu Thr Val Asp Thr Ser Ser Arg Thr Ala Tyr
65                  70                  75                  80

Met Gln Leu Ser Ser Leu Thr Ser Ala Asp Ser Ala Val Tyr Tyr Cys
                85                  90                  95

Ala Pro Tyr Asp Ser Asp Tyr Ala Met Asp Tyr Trp Gly Gln Gly Thr
            100                 105                 110

Ser Val Thr Val Ser Ser
        115

<210> SEQ ID NO 2
<211> LENGTH: 8
<212> TYPE: PRT
<213> ORGANISM: Mus musculus

<400> SEQUENCE: 2

Gly Tyr Thr Phe Thr Ser Tyr Trp
1               5

<210> SEQ ID NO 3
<211> LENGTH: 8
<212> TYPE: PRT
<213> ORGANISM: Mus musculus

<400> SEQUENCE: 3

Ile Tyr Pro Gly Ser Gly Ser Thr
1               5

<210> SEQ ID NO 4
<211> LENGTH: 11
<212> TYPE: PRT
<213> ORGANISM: Mus musculus

<400> SEQUENCE: 4

Ala Pro Tyr Asp Ser Asp Tyr Ala Met Asp Tyr
```

<210> SEQ ID NO 5
<211> LENGTH: 354
<212> TYPE: DNA
<213> ORGANISM: Mus musculus

<400> SEQUENCE: 5

```
caggtccaac tgcagcagcc tggggctgag cttgcgaagc ctggggcttc agtgaagatg      60
tcctgcaagg cttctggcta caccttcacc agctactgga taacctgggt gaagcagagg     120
cctggacaag accttgagtg gattggaaat atttatcctg gtagtggtag tacttactac     180
aatgagaagt tcaagagcaa ggccacactg actgtagaca catcctccag aacagcctac     240
atgcagctca gcagtctgac atctgcggac tctgcggtct attactgtgc ccctatgat     300
tccgactatg ctatggacta ctggggtcaa ggaacctcag tcaccgtctc ctca           354
```

<210> SEQ ID NO 6
<211> LENGTH: 107
<212> TYPE: PRT
<213> ORGANISM: Mus musculus

<400> SEQUENCE: 6

```
Asp Ile Lys Met Thr Gln Ser Pro Ser Ser Met Tyr Ala Ser Leu Gly
1               5                   10                  15
Glu Arg Val Thr Ile Thr Cys Lys Ala Ser Gln Asp Ile Asn Asn Tyr
            20                  25                  30
Leu Ser Trp Phe Gln Gln Lys Pro Gly Lys Ser Pro Lys Thr Leu Ile
        35                  40                  45
Tyr Arg Ala Asn Arg Leu Val Asp Gly Val Pro Ser Arg Val Ser Gly
    50                  55                  60
Ser Gly Ser Gly Gln Asp Tyr Ser Leu Thr Ile Ser Ser Leu Glu Tyr
65                  70                  75                  80
Glu Asp Val Gly Ile Tyr Phe Cys Leu Gln Tyr Asp Glu Phe Pro Leu
                85                  90                  95
Thr Phe Gly Ala Gly Thr Lys Leu Glu Leu Lys
            100                 105
```

<210> SEQ ID NO 7
<211> LENGTH: 6
<212> TYPE: PRT
<213> ORGANISM: Mus musculus

<400> SEQUENCE: 7

```
Gln Asp Ile Asn Asn Tyr
1               5
```

<210> SEQ ID NO 8
<211> LENGTH: 3
<212> TYPE: PRT
<213> ORGANISM: Mus musculus

<400> SEQUENCE: 8

```
Arg Ala Asn
1
```

<210> SEQ ID NO 9
<211> LENGTH: 9
<212> TYPE: PRT
<213> ORGANISM: Mus musculus

```
<400> SEQUENCE: 9

Leu Gln Tyr Asp Glu Phe Pro Leu Thr
1               5

<210> SEQ ID NO 10
<211> LENGTH: 321
<212> TYPE: DNA
<213> ORGANISM: Mus musculus

<400> SEQUENCE: 10
gacatcaaga tgacccagtc tccatcttcc atgtatgcat ctctaggaga gagagtcact      60
atcacttgca aggcgagtca ggacattaat aactatttaa gctggttcca gcagaaacca     120
gggaaatctc ctaagaccct gatctatcgt gcaaacagat tggtagatgg ggtcccatca     180
agggtcagtg gcagtggatc tgggcaagat tattctctca ccatcagcag cctggagtat     240
gaagatgtgg gaatttattt ttgtctacag tatgatgagt ttcctctcac gttcggtgct     300
gggaccaagc tggagctgaa a                                               321

<210> SEQ ID NO 11
<211> LENGTH: 121
<212> TYPE: PRT
<213> ORGANISM: Mus musculus

<400> SEQUENCE: 11

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Ile His Trp Val Lys Glu Arg Thr Glu Gln Gly Leu Glu Trp Phe
        35                  40                  45

Gly Arg Ile Asp Pro Glu Asp Gly Glu Ser Glu Tyr Ala Pro Lys Phe
    50                  55                  60

Gln Gly Lys Ala Thr Leu Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Arg Gly Asp Ser Met Met Val Thr Tyr Phe Asp Tyr Trp Gly Gln
            100                 105                 110

Gly Thr Thr Leu Thr Val Ser Ser Glu
        115                 120

<210> SEQ ID NO 12
<211> LENGTH: 8
<212> TYPE: PRT
<213> ORGANISM: Mus musculus

<400> SEQUENCE: 12

Gly Phe Asn Ile Lys Asp Tyr Tyr
1               5

<210> SEQ ID NO 13
<211> LENGTH: 8
<212> TYPE: PRT
<213> ORGANISM: Mus musculus

<400> SEQUENCE: 13

Ile Asp Pro Glu Asp Gly Glu Ser
1               5
```

<210> SEQ ID NO 14
<211> LENGTH: 13
<212> TYPE: PRT
<213> ORGANISM: Mus musculus

<400> SEQUENCE: 14

Thr Arg Gly Asp Ser Met Met Val Thr Tyr Phe Asp Tyr
1               5                   10

<210> SEQ ID NO 15
<211> LENGTH: 360
<212> TYPE: DNA
<213> ORGANISM: Mus musculus

<400> SEQUENCE: 15
gaggttcagc tgcagcagtc tggggcagaa cttgtgaagc caggggcctc agtcaagttg      60
tcctgcacag cctctggctt caacattaaa gactactata tacactgggt gaaagagagg     120
actgaacagg gcctggagtg gtttggaagg attgatcctg aggatggtga aagtgaatat     180
gccccgaaat tccagggcaa ggccactta acagcagaca catcctccaa tacagcctac     240
ctgcagctca gcagcctgac atctgaggac actgccgtct attactgtac tagaggagac     300
tctatgatgg ttacctactt tgactactgg ggccaaggca ccactctcac ggtctcctca     360

<210> SEQ ID NO 16
<211> LENGTH: 107
<212> TYPE: PRT
<213> ORGANISM: Mus musculus

<400> SEQUENCE: 16

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
                20                  25                  30

Val Ala Trp Tyr Gln Gln Lys Pro Gly Gln Ser Pro Lys Leu Leu Ile
            35                  40                  45

Tyr Trp Ala Phe Thr Arg His Thr Gly Val Pro Asp Arg Phe Thr Ser
        50                  55                  60

Thr Gly Ser Gly Thr Asp Tyr Ala Leu Thr Ile Ser Ser Val Gln Ala
65                  70                  75                  80

Glu Asp Leu Ala Leu Tyr Tyr Cys Gln Gln His Tyr Arg Ser Pro Trp
                85                  90                  95

Thr Phe Gly Gly Gly Thr Lys Leu Glu Ile Lys
            100                 105

<210> SEQ ID NO 17
<211> LENGTH: 6
<212> TYPE: PRT
<213> ORGANISM: Mus musculus

<400> SEQUENCE: 17

Gln Asp Val Ser Thr Ala
1               5

<210> SEQ ID NO 18
<211> LENGTH: 3
<212> TYPE: PRT
<213> ORGANISM: Mus musculus

<400> SEQUENCE: 18

Trp Ala Phe
1

<210> SEQ ID NO 19
<211> LENGTH: 9
<212> TYPE: PRT
<213> ORGANISM: Mus musculus

<400> SEQUENCE: 19

Gln Gln His Tyr Arg Ser Pro Trp Thr
1               5

<210> SEQ ID NO 20
<211> LENGTH: 321
<212> TYPE: DNA
<213> ORGANISM: Mus musculus

<400> SEQUENCE: 20
gacattgtga tgacccagtc tcacaaattc atgtccacat cagtaggaga cagggtcagc      60
atcacctgca aggccagtca ggatgtgagt actgctgtag cctggtatca acaaaaacca     120
gggcaatctc ctaaactact gatttactgg gctttcaccc gtcacactgg agtccctgat     180
cgcttcacaa gcactggatc tgggacagat tatgctctca ccatcagcag tgtgcaggct     240
gaagacctgg cactttatta ctgtcagcaa cattatcgca gtccgtggac gttcggtgga     300
ggcaccaaac tggaaatcaa a                                               321

<210> SEQ ID NO 21
<211> LENGTH: 118
<212> TYPE: PRT
<213> ORGANISM: Mus musculus

<400> SEQUENCE: 21

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Glu Asp Tyr
            20                  25                  30

Tyr Ile His Trp Val Lys Glu Arg Thr Glu Gln Gly Leu Glu Trp Ile
        35                  40                  45

Gly Arg Ile Asp Pro Glu Asp Gly Glu Thr Thr Tyr Ala Pro Gln Phe
    50                  55                  60

Gln Gly Lys Ala Thr Ile Ile Pro Asp Thr Ser Ser Asn Thr Ala Tyr
65                  70                  75                  80

Met Gln Leu Ser Ser Leu Thr Ser Glu Asp Ala Ala Val Tyr Tyr Cys
                85                  90                  95

Ala Arg Ser Ile Tyr Leu Asp Pro Met Asp Tyr Trp Gly Gln Gly Thr
            100                 105                 110

Ser Val Thr Val Ser Ser
        115

<210> SEQ ID NO 22
<211> LENGTH: 8
<212> TYPE: PRT
<213> ORGANISM: Mus musculus

<400> SEQUENCE: 22

Gly Phe Asn Ile Glu Asp Tyr Tyr
1               5

<210> SEQ ID NO 23

-continued

```
<211> LENGTH: 8
<212> TYPE: PRT
<213> ORGANISM: Mus musculus

<400> SEQUENCE: 23

Ile Asp Pro Glu Asp Gly Glu Thr
1               5

<210> SEQ ID NO 24
<211> LENGTH: 11
<212> TYPE: PRT
<213> ORGANISM: Mus musculus

<400> SEQUENCE: 24

Ala Arg Ser Ile Tyr Leu Asp Pro Met Asp Tyr
1               5                  10

<210> SEQ ID NO 25
<211> LENGTH: 354
<212> TYPE: DNA
<213> ORGANISM: Mus musculus

<400> SEQUENCE: 25
gaagttcagc tgcagcagtc tggggcagaa cttgtgaagc caggggcctc agtcaagttg      60
tcctgcacag cttctggctt caacattgaa gactactata tacactgggt gaaggagagg     120
actgaacagg gcctggagtg gattggaagg attgatcctg aggatggtga aactacatat     180
gccccgcagt tccagggcaa ggccactata ataccagaca catcctccaa cacagcctac     240
atgcagctca gcagcctgac atctgaggac gctgccgtct attactgtgc tagatcgatc     300
taccttgatc ctatggacta ctggggtcaa ggaacctcag tcaccgtctc ctca           354

<210> SEQ ID NO 26
<211> LENGTH: 107
<212> TYPE: PRT
<213> ORGANISM: Mus musculus

<400> SEQUENCE: 26

Asp Ile Val Met Thr Gln Ser His Lys Phe Met Ser Thr Ser Val Gly
1               5                  10                  15

Asp Arg Val Ser Ile Thr Cys Lys Ala Ser Gln Asp Val Thr Thr Ala
            20                  25                  30

Val Ala Trp Tyr Gln Gln Lys Pro Gly Gln Ser Pro Lys Ile Leu Ile
        35                  40                  45

Tyr Trp Ala Thr Thr Arg His Thr Gly Val Pro Asp Arg Phe Thr Gly
    50                  55                  60

Ser Ile Ser Gly Thr Thr Tyr Ile Leu Thr Ile Ser Ser Val Gln Ala
65                  70                  75                  80

Glu Asp Leu Ala Leu Tyr Tyr Cys Gln Gln His Tyr Ser Thr Pro Tyr
                85                  90                  95

Thr Phe Gly Gly Gly Thr Lys Leu Glu Ile Lys
            100                 105

<210> SEQ ID NO 27
<211> LENGTH: 6
<212> TYPE: PRT
<213> ORGANISM: Mus musculus

<400> SEQUENCE: 27

Gln Asp Val Thr Thr Ala
1               5
```

<210> SEQ ID NO 28
<211> LENGTH: 3
<212> TYPE: PRT
<213> ORGANISM: Mus musculus

<400> SEQUENCE: 28

Trp Ala Thr
1

<210> SEQ ID NO 29
<211> LENGTH: 9
<212> TYPE: PRT
<213> ORGANISM: Mus musculus

<400> SEQUENCE: 29

Gln Gln His Tyr Ser Thr Pro Tyr Thr
1               5

<210> SEQ ID NO 30
<211> LENGTH: 321
<212> TYPE: DNA
<213> ORGANISM: Mus musculus

<400> SEQUENCE: 30
gacattgtga tgacccagtc tcacaaattc atgtccacat cagtaggaga cagggtcagc    60
atcacctgca aggccagtca ggatgtgact actgctgtcg cctggtatca acaaaaacca   120
ggacagtctc ctaaaatact gatttactgg gcaaccaccc ggcacactgg agtccctgat   180
cgcttcacag gcagtatatc tgggacaact atattctca ccatcagtag tgtgcaggct    240
gaagacctgg cactttatta ctgtcagcaa cattatagca ctccgtacac gttcggaggg   300
gggaccaagc tggaaataaa a                                             321

<210> SEQ ID NO 31
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Thr Trp Val Arg Gln Ala Pro Gly Gln Arg Leu Glu Trp Ile
        35                  40                  45

Gly Asn Ile Tyr Pro Gly Ser Gly Ser Thr Tyr Tyr Asn Glu Lys Phe
    50                  55                  60

Lys Ser Lys Ala Thr Ile Thr Arg Asp Thr Ser Arg Thr Ala Tyr
65                  70                  75                  80

Met Glu Leu Ser Ser Leu Arg Ser Glu Asp Thr Ala Val Tyr Tyr Cys
                85                  90                  95

Ala Pro Tyr Asp Ala Asp Tyr Ala Met Asp Tyr Trp Gly Gln Gly Thr
            100                 105                 110

Leu Val Thr Val Ser Ser
        115

<210> SEQ ID NO 32
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Gly Tyr Thr Phe Thr Ser Tyr Trp
1               5

<210> SEQ ID NO 33
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Ile Tyr Pro Gly Ser Gly Ser Thr
1               5

<210> SEQ ID NO 34
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Ala Pro Tyr Asp Ala Asp Tyr Ala Met Asp Tyr
1               5                   10

<210> SEQ ID NO 35
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 35
gaagtgcagc tggtgcaatc tggcgccgaa gtgaagaaac tggcgcctc tgtgaaggtg      60 tcctgcaagg cttccggcta cacctttacc agctactgga tcacctgggt ccgacaggct    120
cctggccaga gactggaatg gatcggcaac atctaccctg gctccggctc cacctactac    180
aacgagaagt tcaagtccaa ggccacaatc acccgggaca cctcttccag aaccgcctac    240
atggaactgt ccagcctgag atctgaggac accgccgtgt actactgcgc cccttacgac    300
gccgactacg ccatggatta ttggggccag ggcaccctgg tcaccgtgtc ctct           354

<210> SEQ ID NO 36
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

-continued

<400> SEQUENCE: 36

Asp Ile Gln Met Thr Gln Ser Pro Ser Leu Ser Ala Ser Val Gly
1               5                   10                  15

Asp Arg Val Thr Ile Thr Cys Lys Ala Ser Gln Asp Ile Ser Asn Tyr
            20                  25                  30

Leu Ser Trp Phe Gln Gln Lys Pro Gly Lys Ala Pro Lys Leu Leu Ile
        35                  40                  45

Tyr Arg Ala Asn Arg Leu Val Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Leu Gln Tyr Asp Glu Phe Pro Leu
                85                  90                  95

Thr Phe Gly Gly Gly Thr Lys Val Glu Ile Lys
            100                 105

<210> SEQ ID NO 37
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Gln Asp Ile Ser Asn Tyr
1               5

<210> SEQ ID NO 38
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Arg Ala Asn
1

<210> SEQ ID NO 39
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Leu Gln Tyr Asp Glu Phe Pro Leu Thr
1               5

<210> SEQ ID NO 40
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 40

```
gacatccaga tgacccagtc tccatcctct ctgtccgcct ctgtgggcga cagagtgacc        60
atcacatgca aggccagcca ggacatctcc aactacctgt cctggttcca gcagaagcct       120
ggcaaggctc ccaagctgct gatctacaga gccaacagac tggtggaagg cgtgccctcc       180
agattctccg gatctggctc tggcaccgac tttaccctga caatctccag cctgcagcct       240
gaggacttcg ctacctactt ctgcctgcaa tacgacgagt ccctctgac ctttggcgga        300 ggcaccaagg tggaaatcaa g                                                 321
```

```
<210> SEQ ID NO 41
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41
```

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Ile His Trp Val Arg Gln Ala Thr Gly Gln Gly Leu Glu Trp Met
        35                  40                  45

Gly Arg Ile Asp Pro Glu Asp Ala Glu Ser Glu Tyr Ala Pro Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Asp Ser Met Met Val Thr Tyr Phe Asp Tyr Trp Gly Gln
            100                 105                 110

Gly Thr Leu Val Thr Val Ser Ser
        115                 120

```
<210> SEQ ID NO 42
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42
```

Gly Phe Asn Ile Lys Asp Tyr Tyr
1               5

```
<210> SEQ ID NO 43
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43
```

Ile Asp Pro Glu Asp Ala Glu Ser
1               5

<210> SEQ ID NO 44
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 44

Thr Arg Gly Asp Ser Met Met Val Thr Tyr Phe Asp Tyr
1               5                   10

<210> SEQ ID NO 45
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 45
gaagtgcagc tggtgcaatc tggcgccgaa gtgaagaaac tggcgcctc tgtgaaggtg      60 tcctgcaagg cctctggctt caacatcaag gactactaca tccactgggt ccgacaggct    120
accggacagg gacttgagtg gatgggcaga atcgaccctg aggacgccga gtctgagtac    180
gcccctaagt ttcagggcag agtgaccatc accgccgaca cctctaccga caccgcctac    240
atggaactgt ccagcctgag atctgaggac accgccgtgt actactgcac cagaggcgac    300
tccatgatgg ttacctactt cgactactgg ggccagggca ccctggtcac agtttcttcc    360

<210> SEQ ID NO 46
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
                20                  25                  30

Val Ala Trp Tyr Gln Gln Lys Pro Gly Lys Ala Pro Lys Leu Leu Ile
            35                  40                  45

Tyr Trp Ala Phe Thr Arg His Thr Gly Val Pro Ser Arg Phe Ser Gly
    50                  55                  60

Ser Gly Ser Gly Thr Asp Tyr Ala Leu Thr Ile Ser Ser Leu Gln Pro
65                  70                  75                  80

Glu Asp Phe Ala Thr Tyr Tyr Cys Gln Gln His Tyr Arg Ser Pro Trp
                85                  90                  95

Thr Phe Gly Gly Gly Thr Lys Val Glu Ile Lys
            100                 105

<210> SEQ ID NO 47
<211> LENGTH: 6
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 47

Gln Asp Val Ser Thr Ala
1               5

<210> SEQ ID NO 48
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Trp Ala Phe
1

<210> SEQ ID NO 49
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Gln Gln His Tyr Arg Ser Pro Trp Thr
1               5

<210> SEQ ID NO 50
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 50
gacatccaga tgacccagtc tccatcctct ctgtccgcct ctgtgggcga cagagtgacc      60
atcacatgca aggcctctca ggacgtgtcc accgccgttg cttggtatca gcagaagcct     120
ggcaaggccc ctaagctgct gatctactgg gccttcacca gacacaccgg cgtgccctct     180
aggttctccg gctctggctc tggcaccgat tacgctctga caatctccag cctgcagcct     240
gaggacttcg ccacctacta ctgccagcag cactacagaa gcccctggac atttggcgga     300
ggcaccaagg tggaaatcaa g                                               321

<210> SEQ ID NO 51
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Glu Asp Tyr
            20                  25                  30
```

Tyr Met His Trp Val Arg Gln Ala Pro Gly Gln Arg Leu Glu Trp Met
         35                  40                  45

Gly Arg Ile Asp Pro Glu Asp Ala Glu Thr Thr Tyr Ser Pro Lys Phe
 50                  55                  60

Gln Gly Arg Val Thr Ile Ile Pro Asp Thr Ser Ala Asn Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Leu Asp Pro Met Asp Tyr Trp Gly Gln Gly Thr
                100                 105                 110

Leu Val Thr Val Ser Ser
        115

<210> SEQ ID NO 52
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Gly Phe Asn Ile Glu Asp Tyr Tyr
1               5

<210> SEQ ID NO 53
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Ile Asp Pro Glu Asp Ala Glu Thr
1               5

<210> SEQ ID NO 54
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Ala Arg Ser Ile Tyr Leu Asp Pro Met Asp Tyr
1               5                   10

<210> SEQ ID NO 55
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 55
caggtgcagc tggtgcagtc tggcgccgaa gtgaaaaagc ctggcgcctc tgtgaaggtg     60
tcctgcaagg cctctggctt caacatcgag gactactaca tgcactgggt ccgacaggcc    120

```
cctggccaga gattggaatg gatgggcaga atcgaccccg aggacgccga gacaacctac    180
tctcctaagt tccagggccg cgtgacaatc atccctgaca cctctgccaa caccgcctac    240
atggaactgt ccagcctgag atctgaggac accgccgtgt actactgcgc cggtctatc    300 tacctggacc ctatggacta ttggggccag ggcaccctgg tcacagtgtc ctct          354
```

```
<210> SEQ ID NO 56
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Asp Ile Gln Met Thr Gln Ser Pro Lys Ser Leu Ser Ala Ser Val Gly
1               5                   10                  15

Asp Arg Val Thr Ile Thr Cys Arg Ala Ser Gln Asp Val Thr Thr Ala
            20                  25                  30

Leu Ala Trp Tyr Gln Gln Lys Pro Gly Gln Ser Pro Lys Leu Leu Ile
        35                  40                  45

Tyr Trp Ala Thr Thr Arg His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Tyr
                85                  90                  95

Thr Phe Gly Gln Gly Thr Lys Leu Glu Ile Lys
            100                 105

<210> SEQ ID NO 57
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Gln Asp Val Thr Thr Ala
1               5

<210> SEQ ID NO 58
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Trp Ala Thr
1

<210> SEQ ID NO 59
<211> LENGTH: 9
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 59

Gln Gln His Tyr Ser Thr Pro Tyr Thr
1               5

<210> SEQ ID NO 60
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 60

```
gacatccaga tgacccagtc tccaaagtct ctgtccgcct ccgtgggcga cagagtgacc      60
atcacctgta gagcctctca ggacgtgacc accgctctgg cttggtatca gcagaagcct     120
ggccagtctc ctaagctgct gatctactgg gccaccacca gacactctgg cgtgccctct     180
agattctccg gctctggctc tggcaccgac tttaccctga caatctccag cctgcagcct     240
gaggacttcg ccacctacta ctgccagcag cactacagca ccccttacac ctttggccag     300
ggcaccaagc tggaaatcaa g                                                321
```

<210> SEQ ID NO 61
<211> LENGTH: 447
<212> TYPE: PRT
<213> ORGANISM: Mus musculus

<400> SEQUENCE: 61

Gln Val Gln Leu Gln Gln Pro Gly Ala Glu Leu Ala Lys Pro Gly Ala
1               5                   10                  15

Ser Val Lys Met Ser Cys Lys Ala Ser Gly Tyr Thr Phe Thr Ser Tyr
                20                  25                  30

Trp Ile Thr Trp Val Lys Gln Arg Pro Gly Gln Asp Leu Glu Trp Ile
            35                  40                  45

Gly Asn Ile Tyr Pro Gly Ser Gly Ser Thr Tyr Tyr Asn Glu Lys Phe
        50                  55                  60

Lys Ser Lys Ala Thr Leu Thr Val Asp Thr Ser Arg Thr Ala Tyr
65                  70                  75                  80

Met Gln Leu Ser Ser Leu Thr Ser Ala Asp Ser Ala Val Tyr Tyr Cys
                85                  90                  95

Ala Pro Tyr Asp Ser Asp Tyr Ala Met Asp Tyr Trp Gly Gln Gly Thr
                100                 105                 110

Ser Val Thr Val Ser Ser Ala Lys Thr Thr Ala Pro Ser Val Tyr Pro
            115                 120                 125

Leu Ala Pro Val Cys Gly Asp Thr Thr Gly Ser Ser Val Thr Leu Gly
        130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Thr Ser Ser Thr
            180                 185                 190

Trp Pro Ser Gln Ser Ile Thr Cys Asn Val Ala His Pro Ala Ser Ser
        195                 200                 205

```
Thr Lys Val Asp Lys Lys Ile Glu Pro Arg Gly Pro Thr Ile Lys Pro
            210                 215                 220
Cys Pro Pro Cys Lys Cys Pro Ala Pro Asn Leu Leu Gly Gly Pro Ser
225                 230                 235                 240
Val Phe Ile Phe Pro Pro Lys Ile Lys Asp Val Leu Met Ile Ser Leu
                245                 250                 255
Ser Pro Ile Val Thr Cys Val Val Asp Val Ser Glu Asp Asp Pro
            260                 265                 270
Asp Val Gln Ile Ser Trp Phe Val Asn Asn Val Glu Val His Thr Ala
                275                 280                 285
Gln Thr Gln Thr His Arg Glu Asp Tyr Asn Ser Thr Leu Arg Val Val
    290                 295                 300
Ser Ala Leu Pro Ile Gln His Gln Asp Trp Met Ser Gly Lys Glu Phe
305                 310                 315                 320
Lys Cys Lys Val Asn Asn Lys Asp Leu Pro Ala Pro Ile Glu Arg Thr
                325                 330                 335
Ile Ser Lys Pro Lys Gly Ser Val Arg Ala Pro Gln Val Tyr Val Leu
                340                 345                 350
Pro Pro Pro Glu Glu Glu Met Thr Lys Lys Gln Val Thr Leu Thr Cys
            355                 360                 365
Met Val Thr Asp Phe Met Pro Glu Asp Ile Tyr Val Glu Trp Thr Asn
    370                 375                 380
Asn Gly Lys Thr Glu Leu Asn Tyr Lys Asn Thr Glu Pro Val Leu Asp
385                 390                 395                 400
Ser Asp Gly Ser Tyr Phe Met Tyr Ser Lys Leu Arg Val Glu Lys Lys
                405                 410                 415
Asn Trp Val Glu Arg Asn Ser Tyr Ser Cys Ser Val Val His Glu Gly
                420                 425                 430
Leu His Asn His His Thr Thr Lys Ser Phe Ser Arg Thr Pro Gly
            435                 440                 445

<210> SEQ ID NO 62
<211> LENGTH: 1347
<212> TYPE: DNA
<213> ORGANISM: Mus musculus

<400> SEQUENCE: 62
caggtccaac tgcagcagcc tggggctgag cttgcgaagc ctggggcttc agtgaagatg    60
tcctgcaagg cttctggcta caccttcacc agctactgga taacctgggt gaagcagagg   120
cctggacaag accttgagtg gattggaaat atttatcctg gtagtggtag tacttactac   180
aatgagaagt tcaagagcaa ggccacactg actgtagaca tcctccag aacagcctac   240 atgcagctca gcagtctgac atctgcggac tctgcggtct attactgtgc ccctatgat   300 tccgactatg ctatggacta ctggggtcaa ggaaccctcag tcaccgtctc ctcagctaaa   360
acaacagccc catcggtcta tccactggcc cctgtgtgtg gagatacaac tggctcctcg   420
gtgactctag gatgcctggt caagggttat ttccctgagc cagtgacctt gacctggaac   480
tctggttccc tgtccagtgg tgtgcacacc ttcccagctg tcctgcagtc tgacctctac   540
accctcagct caagcgtgac tgtaaccagc tcgacctggc ccagccagtc catcacctgc   600
aatgtggccc accggcaag cagcaccaag gtggacaaga aaattgagcc cagagggccc   660
acaatcaagc cctgtcctcc atgcaaatgc ccagcaccta acctcttggg tggaccatcc   720
gtcttcatct tccctccaaa gatcaaggat gtactcatga tctcccctgag ccccatagtc   780
```

| | |
|---|---|
| acatgtgtag tcgttgatgt gagcgaggat gacccagatg tccagatcag ctggtttgtg | 840 |
| aacaacgtgg aagtgcacac tgctcagaca cagacgcata gagaggatta caacagtact | 900 |
| ctccgggttg tcagtgccct ccccatccag caccaggact ggatgagtgg caaggagttc | 960 |
| aaatgcaagg tcaacaacaa agacctccca gcgcccatcg agagaaccat ctcaaaaccc | 1020 |
| aaagggtcag taagagctcc acaggtatat gtcttgcctc caccagaaga ggagatgact | 1080 |
| aagaaacagg tcactctgac ctgcatggtc acagacttca tgcctgaaga catttacgtg | 1140 |
| gagtggacca caacgggaa aacagagcta aactacaaga acactgaacc agtcctggac | 1200 |
| tctgatggtt cttacttcat gtacagcaag ctgagagtgg agaagaagaa ctgggtggag | 1260 |
| agaaatagct actcctgttc agtggtccac gagggtctgc acaatcacca cacgactaag | 1320 |
| agcttctccc ggactccggg ttagtaa | 1347 |

<210> SEQ ID NO 63
<211> LENGTH: 214
<212> TYPE: PRT
<213> ORGANISM: Mus musculus

<400> SEQUENCE: 63

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Asn Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Val Ser Gly
    50                  55                  60

Ser Gly Ser Gly Gln Asp Tyr Ser Leu Thr Ile Ser Ser Leu Glu Tyr
65                  70                  75                  80

Glu Asp Val Gly Ile Tyr Phe Cys Leu Gln Tyr Asp Glu Phe Pro Leu
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 64
<211> LENGTH: 642
<212> TYPE: DNA
<213> ORGANISM: Mus musculus

<400> SEQUENCE: 64
gacatcaaga tgacccagtc tccatcttcc atgtatgcat ctctaggaga gagagtcact    60

```
atcacttgca aggcgagtca ggacattaat aactatttaa gctggttcca gcagaaacca    120
gggaaatctc ctaagaccct gatctatcgt gcaaacagat tggtagatgg ggtcccatca    180
agggtcagtg gcagtggatc tgggcaagat tattctctca ccatcagcag cctggagtat    240
gaagatgtgg gaatttattt ttgtctacag tatgatgagt ttcctctcac gttcggtgct    300
gggaccaagc tggagctgaa aagagctgac gccgctccta ccgtgtccat ctttccacct    360
agcagcgagc agctgacaag cggcggagcc agcgtcgtgt gcttcctgaa caacttctac    420
cccaaggaca tcaacgtgaa gtggaagatc gacggcagcg agagacagaa cggcgtgctg    480
aatagctgga ccgaccagga cagcaaggac tccacctaca gcatgtccag cacactgacc    540
ctgaccaagg acgagtacga gcggcacaac agctacacat gcgaggccac acacaagacc    600
agcacaagcc ccatcgtgaa gtccttcaac cggaacgagt gc                      642
```

<210> SEQ ID NO 65
<211> LENGTH: 455
<212> TYPE: PRT
<213> ORGANISM: Mus musculus

<400> SEQUENCE: 65

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Ile His Trp Val Lys Glu Arg Thr Glu Gln Gly Leu Glu Trp Phe
        35                  40                  45

Gly Arg Ile Asp Pro Glu Asp Gly Glu Ser Glu Tyr Ala Pro Lys Phe
    50                  55                  60

Gln Gly Lys Ala Thr Leu Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Arg Gly Asp Ser Met Met Val Thr Tyr Phe Asp Tyr Trp Gly Gln
            100                 105                 110

Gly Thr Thr Leu Thr Val Ser Ser Lys Thr Thr Pro Pro Ser Val Tyr
        115                 120                 125

Pro Leu Ala Pro Gly Cys Gly Asp Thr Thr Gly Ser Ser Val Thr Leu
    130                 135                 140

Gly Cys Leu Val Lys Gly Tyr Phe Pro Glu Ser Val Thr Val Thr Trp
145                 150                 155                 160

Asn Ser Gly Ser Leu Ser Ser Ser Val His Thr Phe Pro Ala Leu Leu
                165                 170                 175

Gln Ser Gly Leu Tyr Thr Met Ser Ser Ser Val Thr Val Pro Ser Ser
            180                 185                 190

Thr Trp Pro Ser Gln Thr Val Thr Cys Ser Val Ala His Pro Ala Ser
        195                 200                 205

Ser Thr Thr Val Asp Lys Lys Leu Glu Pro Ser Gly Pro Ile Ser Thr
    210                 215                 220

Ile Asn Pro Cys Pro Pro Cys Lys Glu Cys His Lys Cys Pro Ala Pro
225                 230                 235                 240

Asn Leu Glu Gly Gly Pro Ser Val Phe Ile Phe Pro Pro Asn Ile Lys
                245                 250                 255

Asp Val Leu Met Ile Ser Leu Thr Pro Lys Val Thr Cys Val Val Val
            260                 265                 270

```
Asp Val Ser Glu Asp Pro Asp Val Gln Ile Ser Trp Phe Val Asn
            275                 280                 285

Asn Val Glu Val His Thr Ala Gln Thr Gln Thr His Arg Glu Asp Tyr
            290                 295                 300

Asn Ser Thr Ile Arg Val Val Ser Thr Leu Pro Ile Gln His Gln Asp
305                 310                 315                 320

Trp Met Ser Gly Lys Glu Phe Lys Cys Lys Val Asn Asn Lys Asp Leu
                325                 330                 335

Pro Ser Pro Ile Glu Arg Thr Ile Ser Lys Ile Lys Gly Leu Val Arg
            340                 345                 350

Ala Pro Gln Val Tyr Ile Leu Pro Pro Ala Glu Gln Leu Ser Arg
            355                 360                 365

Lys Asp Val Ser Leu Thr Cys Leu Val Val Gly Phe Asn Pro Gly Asp
370                 375                 380

Ile Ser Val Glu Trp Thr Ser Asn Gly His Thr Glu Glu Asn Tyr Lys
385                 390                 395                 400

Asp Thr Ala Pro Val Leu Asp Ser Asp Gly Ser Tyr Phe Ile Tyr Ser
                405                 410                 415

Lys Leu Asn Met Lys Thr Ser Lys Trp Glu Lys Thr Asp Ser Phe Ser
                420                 425                 430

Cys Asn Val Arg His Glu Gly Leu Lys Asn Tyr Tyr Leu Lys Lys Thr
                435                 440                 445

Ile Ser Arg Ser Pro Gly Lys
450                 455

<210> SEQ ID NO 66
<211> LENGTH: 1365
<212> TYPE: DNA
<213> ORGANISM: Mus musculus

<400> SEQUENCE: 66
gaggttcagc tgcagcagtc tggggcagaa cttgtgaagc caggggcctc agtcaagttg      60
tcctgcacag cctctggctt caacattaaa gactactata tacactgggt gaaagagagg     120
actgaacagg gcctggagtg gtttggaagg attgatcctg aggatggtga agtgaatat      180 gccccgaaat tccagggcaa ggccacttta acagcagaca catcctccaa tacagcctac     240
ctgcagctca gcagcctgac atctgaggac actgccgtct attactgtac tagaggagac     300
tctatgatgg ttacctactt tgactactgg ggccaaggca ccactctcac ggtctcctca     360
aagaccacac ctcctagcgt gtaccctctg gctcctggct gtggcgatac aacaggcagc     420
tctgtgacac tgggctgcct ggtcaagggc tactttcctg agagcgtgac agtgacctgg     480
aacagcggca gctgtctag cagcgtgcac acctttccag ctctgctcca gagcggcctg     540
tacaccatgt cctctagtgt gaccgtgcct agcagcacct ggcctagcca gacagtgaca     600
tgtagcgtgg cccatcctgc cagcagcaca accgtggaca gaagctgga acctagcggc     660 cccatcagca ccatcaatcc ctgtcctcca tgcaaagaat gccacaagtg ccccgctcct     720
aacctggaag tggcccaag cgtgttcatc ttcccaccta acatcaagga cgtgctgatg     780
atcagcctga cacctaaagt gacctgcgtg gtggtggacg tgtccgagga tgatcccgat     840
gtgcagatca gttggttcgt gaacaacgtg gaagtgcaca cagcccagac acagacccac     900
agagaggact acaatagcac cattcgcgtg gtgtccacac tgcctatcca gcaccaggat     960
tggatgagcg gcaaagagtt caagtgcaaa gtgaacaaca aggacctgcc ttctccaatc    1020
```

| | | |
|---|---|---|
| gagcggacca tcagcaagat caagggactc gtcagagccc ctcaggtgta catcttgcct | 1080 | |
| ccaccagccg agcagctgag cagaaaggat gtgtccctga cctgtctggt cgtgggcttc | 1140 | |
| aaccctggcg acatcagcgt ggaatggacc agcaatggcc acaccgagga aaactacaag | 1200 | |
| gacacagccc ctgtgctgga cagcgacggc agctacttca tctacagcaa gctgaacatg | 1260 | |
| aagaccagca agtgggagaa aaccgacagc ttctcctgca acgtgcggca cgagggcctg | 1320 | |
| aagaactact acctgaagaa aaccatctct cggagccccg gcaag | 1365 | |

<210> SEQ ID NO 67
<211> LENGTH: 214
<212> TYPE: PRT
<213> ORGANISM: Mus musculus

<400> SEQUENCE: 67

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Trp Ala Phe Thr Arg His Thr Gly Val Pro Asp Arg Phe Thr Ser
    50                  55                  60

Thr Gly Ser Gly Thr Asp Tyr Ala Leu Thr Ile Ser Ser Val Gln Ala
65                  70                  75                  80

Glu Asp Leu Ala Leu Tyr Tyr Cys Gln Gln His Tyr Arg Ser Pro Trp
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 68
<211> LENGTH: 642
<212> TYPE: DNA
<213> ORGANISM: Mus musculus

<400> SEQUENCE: 68

| | | |
|---|---|---|
| gacattgtga tgacccagtc tcacaaattc atgtccacat cagtaggaga cagggtcagc | 60 | |
| atcacctgca aggccagtca ggatgtgagt actgctgtag cctggtatca acaaaaacca | 120 | |
| gggcaatctc ctaaactact gatttactgg gctttcaccc gtcacactgg agtccctgat | 180 | |
| cgcttcacaa gcactggatc tgggacagat tatgctctca ccatcagcag tgtgcaggct | 240 | |
| gaagacctgg cactttatta ctgtcagcaa cattatcgca gtccgtggac gttcggtgga | 300 | |

```
ggcaccaaac tggaaatcaa aagagctgac gccgctccta ccgtgtccat ctttccacct    360
agcagcgagc agctgacaag cggcggagcc agcgtcgtgt gcttcctgaa caacttctac    420
cccaaggaca tcaacgtgaa gtggaagatc gacggcagcg agagacagaa cggcgtgctg    480
aatagctgga ccgaccagga cagcaaggac tccacctaca gcatgtccag cacactgacc    540
ctgaccaagg acgagtacga gcggcacaac agctacacat gcgaggccac acacaagacc    600
agcacaagcc ccatcgtgaa gtccttcaac cggaacgagt gc                       642
```

<210> SEQ ID NO 69
<211> LENGTH: 453
<212> TYPE: PRT
<213> ORGANISM: Mus musculus

<400> SEQUENCE: 69

```
Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Glu Asp Tyr
            20                  25                  30

Tyr Ile His Trp Val Lys Glu Arg Thr Glu Gln Gly Leu Glu Trp Ile
        35                  40                  45

Gly Arg Ile Asp Pro Glu Asp Gly Glu Thr Thr Tyr Ala Pro Gln Phe
    50                  55                  60

Gln Gly Lys Ala Thr Ile Ile Pro Asp Thr Ser Ser Asn Thr Ala Tyr
65                  70                  75                  80

Met Gln Leu Ser Ser Leu Thr Ser Glu Asp Ala Ala Val Tyr Tyr Cys
                85                  90                  95

Ala Arg Ser Ile Tyr Leu Asp Pro Met Asp Tyr Trp Gly Gln Gly Thr
            100                 105                 110

Ser Val Thr Val Ser Ser Lys Thr Thr Pro Pro Ser Val Tyr Pro Leu
        115                 120                 125

Ala Pro Gly Cys Gly Asp Thr Thr Gly Ser Ser Val Thr Leu Gly Cys
    130                 135                 140

Leu Val Lys Gly Tyr Phe Pro Glu Ser Val Thr Val Thr Trp Asn Ser
145                 150                 155                 160

Gly Ser Leu Ser Ser Ser Val His Thr Phe Pro Ala Leu Leu Gln Ser
                165                 170                 175

Gly Leu Tyr Thr Met Ser Ser Ser Val Thr Val Pro Ser Ser Thr Trp
            180                 185                 190

Pro Ser Gln Thr Val Thr Cys Ser Val Ala His Pro Ala Ser Ser Thr
        195                 200                 205

Thr Val Asp Lys Lys Leu Glu Pro Ser Gly Pro Ile Ser Thr Ile Asn
    210                 215                 220

Pro Cys Pro Pro Cys Lys Glu Cys His Lys Cys Pro Ala Pro Asn Leu
225                 230                 235                 240

Glu Gly Gly Pro Ser Val Phe Ile Phe Pro Pro Asn Ile Lys Asp Val
                245                 250                 255

Leu Met Ile Ser Leu Thr Pro Lys Val Thr Cys Val Val Val Asp Val
            260                 265                 270

Ser Glu Asp Asp Pro Asp Val Gln Ile Ser Trp Phe Val Asn Asn Val
        275                 280                 285

Glu Val His Thr Ala Gln Thr Gln Thr His Arg Glu Asp Tyr Asn Ser
    290                 295                 300

Thr Ile Arg Val Val Ser Thr Leu Pro Ile Gln His Gln Asp Trp Met
```

```
          305                 310                 315                 320
Ser Gly Lys Glu Phe Lys Cys Lys Val Asn Asn Lys Asp Leu Pro Ser
                325                 330                 335

Pro Ile Glu Arg Thr Ile Ser Lys Ile Lys Gly Leu Val Arg Ala Pro
                340                 345                 350

Gln Val Tyr Ile Leu Pro Pro Ala Glu Gln Leu Ser Arg Lys Asp
                355                 360                 365

Val Ser Leu Thr Cys Leu Val Val Gly Phe Asn Pro Gly Asp Ile Ser
        370                 375                 380

Val Glu Trp Thr Ser Asn Gly His Thr Glu Glu Asn Tyr Lys Asp Thr
385                 390                 395                 400

Ala Pro Val Leu Asp Ser Asp Gly Ser Tyr Phe Ile Tyr Ser Lys Leu
                405                 410                 415

Asn Met Lys Thr Ser Lys Trp Glu Lys Thr Asp Ser Phe Ser Cys Asn
                420                 425                 430

Val Arg His Glu Gly Leu Lys Asn Tyr Tyr Leu Lys Lys Thr Ile Ser
                435                 440                 445

Arg Ser Pro Gly Lys
        450

<210> SEQ ID NO 70
<211> LENGTH: 1359
<212> TYPE: DNA
<213> ORGANISM: Mus musculus

<400> SEQUENCE: 70
gaggttcagc tgcagcagtc tggcgccgag cttgtgaaac ctggcgcctc tgtgaagctg        60
agctgtaccg ccagcggctt caacatcgag gactactaca tccactgggt caaagagcgg       120
accgagcagg gactcgagtg gatcggaaga atcgaccccg aggacggcga caacatac         180 gcccctcagt ttcagggcaa agccacaatc atccccgaca ccagcagcaa caccgcctac       240
atgcaactga gcagcctgac ctctgaagat gccgccgtgt actactgcgc ccggtccatc       300
tatctggacc ccatggatta ttggggccag ggcacaagcg tgaccgtgtc ctctaagacc       360
acacctccta gcgtgtaccc tctggctcct ggctgtggcg atacaacagg cagctctgtg       420
acactgggct gcctggtcaa gggctacttt cctgagagcg tgacagtgac ctggaacagc       480
ggcagcctgt ctagcagcgt gcacacctt ccagctctgc tccagagcgg cctgtacacc        540
atgtcctcta gtgtgaccgt gcctagcagc acctggccta gccagacagt gacatgtagc       600
gtggcccatc ctgccagcag cacaaccgtg acaagaagc tggaacctag cggccccatc        660
agcaccatca tccctgtcc tccatgcaaa gaatgccaca gtgccccgc tcctaacctg         720 gaaggtggcc caagcgtgtt catcttccca cctaacatca ggacgtgct gatgatcagc        780 ctgacaccta aagtgacctg cgtggtggtg acgtgtccg aggatgatcc cgatgtgcag        840
atcagttggt tcgtgaacaa cgtggaagtg cacacagccc agacacagac ccacagagag       900
gactacaata gcaccattcg cgtggtgtcc acactgccta tccagcacca ggattggatg       960
agcggcaaag agttcaagtg caaagtgaac aacaaggacc tgccttctcc aatcgagcgg      1020
accatcagca gatcaaggg actcgtcaga gcccctcagg tgtacatctt gcctccacca      1080
gccgagcagc tgagcagaaa ggatgtgtcc ctgacctgtc tggtcgtggg cttcaaccct      1140
ggcgacatca gcgtggaatg gaccagcaat ggccacaccg aggaaaacta caaggacaca      1200
gcccctgtgc tggacagcga cggcagctac ttcatctaca gcaagctgaa catgaagacc      1260
```

-continued agcaagtggg agaaaaccga cagcttctcc tgcaacgtgc ggcacgaggg cctgaagaac 1320
tactacctga agaaaaccat ctctcggagc cccggcaag 1359

<210> SEQ ID NO 71
<211> LENGTH: 214
<212> TYPE: PRT
<213> ORGANISM: Mus musculus

<400> SEQUENCE: 71

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Thr Thr Ala
            20                  25                  30

Val Ala Trp Tyr Gln Gln Lys Pro Gly Gln Ser Pro Lys Ile Leu Ile
        35                  40                  45

Tyr Trp Ala Thr Thr Arg His Thr Gly Val Pro Asp Arg Phe Thr Gly
    50                  55                  60

Ser Ile Ser Gly Thr Thr Tyr Ile Leu Thr Ile Ser Ser Val Gln Ala
65                  70                  75                  80

Glu Asp Leu Ala Leu Tyr Tyr Cys Gln Gln His Tyr Ser Thr Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 72
<211> LENGTH: 642
<212> TYPE: DNA
<213> ORGANISM: Mus musculus

<400> SEQUENCE: 72
gacatcgtga tgacccagag ccacaagttc atgagcacca gcgtgggcga cagagtgtcc 60
atcacctgta agccagcca ggacgtgaca acagccgtgg cctggtatca gcagaagcct 120
ggccagtctc ctaagatcct gatctactgg gccaccacca gacacaccgg cgtgccagat 180
agattcaccg gcagcatcag cggcaccacc tacatcctga caatcagctc tgtgcaggcc 240
gaggatctgg ccctgtacta ctgtcagcag cactacagca cccccttcac ctttggcgga 300
ggcaccaagc tggaaatcaa agagagctga ccgctcctac cgtgtccat ctttccacct 360 agcagcgagc agctgacaag cggcggagcc agcgtcgtgt gcttcctgaa caacttctac 420
cccaaggaca tcaacgtgaa gtggaagatc gacggcagcg agagacagaa cggcgtgctg 480
aatagctgga ccgaccagga cagcaaggac tccacctaca gcatgtccag cacactgacc 540

```
ctgaccaagg acgagtacga gcggcacaac agctacacat gcgaggccac acacaagacc    600
agcacaagcc ccatcgtgaa gtccttcaac cggaacgagt gc                        642
```

<210> SEQ ID NO 73
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Thr Trp Val Arg Gln Ala Pro Gly Gln Arg Leu Glu Trp Ile
        35                  40                  45

Gly Asn Ile Tyr Pro Gly Ser Gly Ser Thr Tyr Tyr Asn Glu Lys Phe
    50                  55                  60

Lys Ser Lys Ala Thr Ile Thr Arg Asp Thr Ser Arg Thr Ala Tyr
65                  70                  75                  80

Met Glu Leu Ser Ser Leu Arg Ser Glu Asp Thr Ala Val Tyr Tyr Cys
                85                  90                  95

Ala Pro Tyr Asp Ala Asp Tyr Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335
```

```
Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 74
<211> LENGTH: 1341
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 74
gaagtgcagc tggtgcaatc tggcgccgaa gtgaagaaac ctggcgcctc tgtgaaggtg      60
tcctgcaagg cttccggcta cacctttacc agctactgga tcacctgggt ccgacaggct    120
cctggccaga gactggaatg gatcggcaac atctaccctg ctccggctc cacctactac     180 aacgagaagt tcaagtccaa ggccacaatc acccgggaca cctcttccag aaccgcctac    240
atggaactgt ccagcctgag atctgaggac accgccgtgt actactgcgc cccttacgac    300
gccgactacg ccatggatta ttggggccag ggcaccctgg tcaccgtgtc ctctgcttct    360
accaagggac ccagcgtgtt ccctctggct ccttccagca gtctacctc tggcggaaca    420 gctgctctgg ctgcctggt caaggactac tttcctgagc ctgtgaccgt gtcttggaac    480
tctggcgctc tgacatccgg cgtgcacaca tttccagctg tgctgcagtc ctccggcctg    540
tactctctgt cctctgtcgt gaccgtgcct cctctagcc tgggcaccca gacctacatc    600
tgcaatgtga accacaagcc ttccaacacc aaggtggaca gaaggtgga acccaagtcc    660 tgcgacaaga cccacacctg tcctccatgt cctgctccag aactgctcgg cggaccttcc    720
gtgttcctgt ttcctccaaa gcctaaggac accctgatga tctctcggac ccctgaagtg    780
acctgcgtgg tggtggatgt gtctcacgag acccagaag tgaagttcaa ttggtacgtg    840
gacggcgtgg aagtgcacaa cgccaagacc aagcctagag aggaacagta cgccagcacc    900
tacagagtgg tgtccgtgct gacagtgctg caccaggatt ggctgaacgg caaagagtac    960
aagtgcaagg tgtccaacaa ggccctgcct gctcctatcg aaaagaccat cagcaaggcc   1020
aagggccagc ctagagaacc ccaggtttac accttgcctc catctcggga cgagctgacc   1080
aagaaccagg tgtccctgac ctgtctcgtg aagggcttct acccctccga catcgccgtg   1140
gaatgggagt ctaatggcca gccagagaac aactacaaga caacccctcc tgtgctggac   1200
tccgacggct cattcttcct gtactccaag ctgaccgtgg acaagtccag atggcagcag   1260
ggcaacgtgt tctcctgctc cgtgatgcac gaggccctgc acaatcacta cacacagaag   1320
tccctgtctc tgtcccctgg c                                              1341
```

<210> SEQ ID NO 75
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Ser Asn Tyr
            20                  25                  30

Leu Ser Trp Phe Gln Gln Lys Pro Gly Lys Ala Pro Lys Leu Leu Ile
        35                  40                  45

Tyr Arg Ala Asn Arg Leu Val Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Leu Gln Tyr Asp Glu Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 76
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 76
gacatccaga tgacccagtc tccatcctct ctgtccgcct ctgtgggcga cagagtgacc        60
atcacatgca aggccagcca ggacatctcc aactacctgt cctggttcca gcagaagcct       120
ggcaaggctc ccaagctgct gatctacaga gccaacagac tggtggaagg cgtgccctcc       180
agattctccg gatctggctc tggcaccgac tttaccctga caatctccag cctgcagcct       240
gaggacttcg ctacctactt ctgcctgcaa tacgacgagt tccctctgac ctttggcgga       300
ggcaccaagg tggaaatcaa gcggacagtg gccgctcctt ccgtgttcat cttcccacct       360

```
tccgacgagc agctgaagtc cggcacagct tctgtcgtgt gcctgctgaa caacttctac    420
cctcgggaag ccaaggtgca gtggaaggtg acaatgccc tgcagtccgg caactcccaa    480
gagtctgtga ccgagcagga ctccaaggac agcacctaca gcctgtcctc cacactgacc    540
ctgtccaagg ccgactacga aagcacaag gtgtacgcct gcgaagtgac ccatcagggc    600
ctgtctagcc ctgtgaccaa gtctttcaac cggggcgagt gt                      642
```

```
<210> SEQ ID NO 77
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77
```

| | | | | | | | | | | | | | | |
|---|---|---|---|---|---|---|---|---|---|---|---|---|---|---|
| Glu | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Lys | Val | Ser | Cys | Lys | Ala | Ser | Gly | Phe | Asn | Ile | Lys | Asp | Tyr |
| | | | 20 | | | | | 25 | | | | | 30 | | |
| Tyr | Ile | His | Trp | Val | Arg | Gln | Ala | Thr | Gly | Gln | Gly | Leu | Glu | Trp | Met |
| | | 35 | | | | | 40 | | | | | 45 | | | |
| Gly | Arg | Ile | Asp | Pro | Glu | Asp | Ala | Glu | Ser | Gly | Tyr | Ala | Pro | Lys | Phe |
| | 50 | | | | | 55 | | | | | 60 | | | | |
| Gln | Gly | Arg | Val | Thr | Ile | Thr | Ala | Asp | Thr | Ser | Thr | Asp | Thr | Ala | Tyr |
| 65 | | | | | 70 | | | | | 75 | | | | | 80 |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Thr | Arg | Gly | Asp | Ser | Met | Met | Val | Thr | Tyr | Phe | Asp | Tyr | Trp | Gly | Gln |
| | | | 100 | | | | | 105 | | | | | 110 | | |
| Gly | Thr | Leu | Val | Thr | Val | Ser | Ser | Ala | Ser | Thr | Lys | Gly | Pro | Ser | Val |
| | | 115 | | | | | 120 | | | | | 125 | | | |
| Phe | Pro | Leu | Ala | Pro | Ser | Ser | Lys | Ser | Thr | Ser | Gly | Gly | Thr | Ala | Ala |
| | 130 | | | | | 135 | | | | | 140 | | | | |
| Leu | Gly | Cys | Leu | Val | Lys | Asp | Tyr | Phe | Pro | Glu | Pro | Val | Thr | Val | Ser |
| 145 | | | | | 150 | | | | | 155 | | | | | 160 |
| Trp | Asn | Ser | Gly | Ala | Leu | Thr | Ser | Gly | Val | His | Thr | Phe | Pro | Ala | Val |
| | | | | 165 | | | | | 170 | | | | | 175 | |
| Leu | Gln | Ser | Ser | Gly | Leu | Tyr | Ser | Leu | Ser | Ser | Val | Val | Thr | Val | Pro |
| | | | 180 | | | | | 185 | | | | | 190 | | |
| Ser | Ser | Ser | Leu | Gly | Thr | Gln | Thr | Tyr | Ile | Cys | Asn | Val | Asn | His | Lys |
| | | 195 | | | | | 200 | | | | | 205 | | | |
| Pro | Ser | Asn | Thr | Lys | Val | Asp | Lys | Lys | Val | Glu | Pro | Lys | Ser | Cys | Asp |
| | 210 | | | | | 215 | | | | | 220 | | | | |
| Lys | Thr | His | Thr | Cys | Pro | Pro | Cys | Pro | Ala | Pro | Glu | Leu | Leu | Gly | Gly |
| 225 | | | | | 230 | | | | | 235 | | | | | 240 |
| Pro | Ser | Val | Phe | Leu | Phe | Pro | Pro | Lys | Pro | Lys | Asp | Thr | Leu | Met | Ile |
| | | | | 245 | | | | | 250 | | | | | 255 | |
| Ser | Arg | Thr | Pro | Glu | Val | Thr | Cys | Val | Val | Val | Asp | Val | Ser | His | Glu |
| | | | 260 | | | | | 265 | | | | | 270 | | |
| Asp | Pro | Glu | Val | Lys | Phe | Asn | Trp | Tyr | Val | Asp | Gly | Val | Glu | Val | His |
| | | 275 | | | | | 280 | | | | | 285 | | | |
| Asn | Ala | Lys | Thr | Lys | Pro | Arg | Glu | Glu | Gln | Tyr | Ala | Ser | Thr | Tyr | Arg |
| | 290 | | | | | 295 | | | | | 300 | | | | |

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
                435                 440                 445

Gly
```

<210> SEQ ID NO 78
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 78

```
gaagtgcagc tggtgcaatc tggcgccgaa gtgaagaaac ctggcgcctc tgtgaaggtg      60
tcctgcaagg cctctggctt caacatcaag gactactaca tccactgggt ccgacaggct     120
accggacagg gacttgagtg gatgggcaga atcgaccctg aggacgccga gtctgagtac     180
gcccctaagt ttcagggcag agtgaccatc accgccgaca cctctaccga caccgcctac     240
atggaactgt ccagcctgag atctgaggac accgccgtgt actactgcac cagaggcgac     300
tccatgatgg ttacctactt cgactactgg ggccagggca ccctggtcac agtttcttcc     360
gcttccacca agggacccag cgtgttccct ctggctcctt ccagcaagtc tacctctggc     420
ggaacagctg ctctgggctg cctggtcaag gattacttcc ctgagcctgt gaccgtgtcc     480
tggaactctg gcgctctgac atccggcgtg cacaccttc cagctgtgct gcaatcctcc      540
ggcctgtact ctctgtcctc cgtcgtgacc gtgccttcta gctctctggg cacccagacc     600
tacatctgca atgtgaacca caagccttcc aacaccaagg tggacaagaa ggtggaaccc     660
aagtcctgcg acaagaccca cacctgtcct ccatgtcctg ctccagaact gctcggcgga     720
ccttccgtgt tcctgtttcc tccaaagcct aaggacaccc tgatgatctc tcggacccct     780
gaagtgacct gcgtggtggt ggatgtgtct cacgaggacc cagaagtgaa gttcaattgg     840
tacgtggacg gcgtggaagt gcacaacgcc aagaccaagc ctagagagga acagtacgcc     900
tccacctaca gagtggtgtc cgtgctgaca gtgctgcacc aggattggct gaacggcaaa     960
gagtacaagt gcaaggtgtc caacaaggca ctgcccgctc ctatcgaaaa gaccatctcc    1020
aaggccaagg gccagcctag agaacccag gtttacacct tgcctccatc tcgggacgag     1080
ctgaccaaga accaggtgtc cctgacctgt ctcgtgaagg gcttctaccc ctccgacatc    1140
```

-continued

```
gccgtggaat gggagtctaa tgccagcca gagaacaact acaagacaac ccctcctgtg    1200
ctggactccg acggctcatt cttcctgtac tccaagctga ccgtggacaa gtccagatgg    1260
cagcagggca acgtgttctc ctgctccgtg atgcacgagg ccctgcacaa tcactacaca    1320
cagaagtctc tgtccctgtc tcctggc                                       1347
```

<210> SEQ ID NO 79
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 79

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Trp Ala Phe Thr Arg His Thr Gly Val Pro Ser Arg Phe Ser Gly
    50                  55                  60

Ser Gly Ser Gly Thr Asp Tyr Ala Leu Thr Ile Ser Ser Leu Gln Pro
65                  70                  75                  80

Glu Asp Phe Ala Thr Tyr Tyr Cys Gln Gln His Tyr Arg Ser Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 80
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 80

```
gacatccaga tgacccagtc tccatcctct ctgtccgcct ctgtgggcga cagagtgacc    60
atcacatgca aggcctctca ggacgtgtcc accgccgttg cttggtatca gcagaagcct   120
ggcaaggccc ctaagctgct gatctactgg gccttcacca gacacaccgg cgtgccctct   180
```

```
aggttctccg gctctggctc tggcaccgat tacgctctga caatctccag cctgcagcct    240
gaggacttcg ccacctacta ctgccagcag cactacagaa gccctggac atttggcgga    300 ggcaccaagg tggaaatcaa gcggacagtg gccgctcctt ccgtgttcat cttcccacct    360
tccgacgagc agctgaagtc cggcacagct tctgtcgtgt gcctgctgaa caacttctac    420
cctcgggaag ccaaggtgca gtggaaggtg gacaatgccc tgcagtccgg caactcccaa    480
gagtctgtga ccgagcagga ctccaaggac agcacctaca gcctgtcctc cacactgacc    540
ctgtccaagg ccgactacga gaagcacaag gtgtacgcct gcgaagtgac ccatcagggc    600
ctgtctagcc ctgtgaccaa gtctttcaac cggggcgagt gt    642
```

<210> SEQ ID NO 81
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 81

```
Gln Val Gln Leu Val Gln Ser Gly Ala Glu Val Lys Lys Pro Gly Ala
1               5                  10                  15

Ser Val Lys Val Ser Cys Lys Ala Ser Gly Phe Asn Ile Glu Asp Tyr
            20                  25                  30

Tyr Met His Trp Val Arg Gln Ala Pro Gly Gln Arg Leu Glu Trp Met
        35                  40                  45

Gly Arg Ile Asp Pro Glu Asp Ala Glu Thr Thr Tyr Ser Pro Lys Phe
    50                  55                  60

Gln Gly Arg Val Thr Ile Ile Pro Asp Thr Ser Ala Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Leu Asp Pro Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270
```

```
Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 82
<211> LENGTH: 1341
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 82
caggtgcagc tggtgcagtc tggcgccgaa gtgaaaaagc ctggcgcctc tgtgaaggtg      60
tcctgcaagg cctctggctt caacatcgag gactactaca tgcactgggt ccgacaggcc     120
cctggccaga gattggaatg gatgggcaga atcgaccccg aggacgccga gacaacctac     180
tctcctaagt tccagggccg cgtgacaatc atccctgaca cctctgccaa caccgcctac     240
atggaactgt ccagcctgag atctgaggac accgccgtgt actactgcgc ccggtctatc     300
tacctggacc ctatggacta ttggggccag ggcacccctg tcacagtgtc ctctgcttct     360
accaagggac ccagcgtgtt ccctctggct ccttccagca gtctacctc tggcggaaca      420 gctgctctgg ctgcctggt caaggactac tttccagagc ctgtgaccgt gtcctggaac      480
tctggcgctc tgacatctgg cgtgcacacc tttccagctg tgctgcagtc ctccggcctg     540
tactctctgt cctctgtcgt gaccgtgcct tccagctctc tgggaaccca gacctacatc     600
tgcaatgtga accacaagcc ttccaacacc aaggtggaca gaaggtgga acccaagtcc      660 tgcgacaaga cccacacctg tcctccatgt cctgctccag aagctgctgg cggcccttcc     720
gtgtttctgt tccctccaaa gcctaaggac ccctgatga tctctcggac ccctgaagtg      780
acctgcgtgg tggtggatgt gtctcacgag acccagaag tgaagttcaa ttggtacgtg      840
gacggcgtgg aagtgcacaa cgccaagacc aagcctagag aggaacagta caactccacc     900
tacagagtgg tgtccgtgct gaccgtgctg caccaggatt ggctgaacgg caaagagtac     960
aagtgcaagg tgtccaacaa ggcactgccc gctcctatcg aaaagaccat ctccaaggcc    1020
```

```
aagggccagc taggggaacc ccaggtttac accctgcctc caagccggga agagatgacc    1080
aagaaccagg tgtccctgac ctgcctcgtg aagggcttct accctccga catcgccgtg     1140 gaatgggaga gcaatggcca gccagagaac aactacaaga caaccctcc tgtgctggac    1200 tccgacggct cattcttcct gtactccaag ctgacagtgg acaagtccag atggcagcag    1260
ggcaacgtgt tctcctgctc cgtgatgcac gaggccctgc acaatcacta cacacagaag    1320
tccctgtctc tgtcccctgg c                                              1341
```

<210> SEQ ID NO 83
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

```
Asp Ile Gln Met Thr Gln Ser Pro Lys Ser Leu Ser Ala Ser Val Gly
1               5                   10                  15

Asp Arg Val Thr Ile Thr Cys Arg Ala Ser Gln Asp Val Thr Thr Ala
            20                  25                  30

Leu Ala Trp Tyr Gln Gln Lys Pro Gly Gln Ser Pro Lys Leu Leu Ile
        35                  40                  45

Tyr Trp Ala Thr Thr Arg His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 84
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 84

```
gacatccaga tgacccagtc tccaaagtct ctgtccgcct ccgtgggcga cagagtgacc        60
atcacctgta gagcctctca ggacgtgacc accgctctgg cttggtatca gcagaagcct      120
ggccagtctc ctaagctgct gatctactgg gccaccacca gacactctgg cgtgccctct      180
agattctccg gctctggctc tggcaccgac tttacccctg caatctccag cctgcagcct      240
gaggacttcg ccacctacta ctgccagcag cactacagca ccccttacac ctttggccag      300
ggcaccaagc tggaaatcaa gcggacagtg gccgctcctt ccgtgttcat cttcccacct      360
tccgacgagc agctgaagtc cggcacagct tctgtcgtgt gcctgctgaa caacttctac      420
cctcgggaag ccaaggtgca gtggaaggtg gacaatgccc tgcagtccgg caactcccaa      480
gagtctgtga ccgagcagga ctccaaggac agcacctaca gcctgtcctc cacactgacc      540
ctgtccaagg ccgactacga gaagcacaag gtgtacgcct gcgaagtgac ccatcagggc      600
ctgtctagcc ctgtgaccaa gtctttcaac cggggcgagt gt                         642
```

<210> SEQ ID NO 85
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 85

```
aagcagggca gacattgcga t                                                 21
```

<210> SEQ ID NO 86
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 86

```
caggatgtgg ctctaggcta t                                                 21
```

<210> SEQ ID NO 87
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 87

```
acccacactg tgcccatcta                                                   20
```

<210> SEQ ID NO 88
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 88

```
cacgctcggt caggatcttc                                                   20
```

-continued

```
<210> SEQ ID NO 89
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 89
```

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Glu Asp Tyr
            20                  25                  30

Tyr Met His Trp Val Arg Gln Ala Pro Gly Gln Arg Leu Glu Trp Met
        35                  40                  45

Gly Arg Ile Asp Pro Glu Asp Gly Glu Thr Thr Tyr Ser Pro Lys Phe
    50                  55                  60

Gln Gly Arg Val Thr Ile Ile Pro Asp Thr Ser Ala Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Leu Asp Pro Met Asp Tyr Trp Gly Gln Gly Thr
            100                 105                 110

Leu Val Thr Val Ser Ser
        115

```
<210> SEQ ID NO 90
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 90
```

Gln Val Gln Leu Gln Gln Ser Gly Ala Glu Val Lys Lys Pro Gly Ala
1               5                   10                  15

Ser Val Lys Val Ser Cys Thr Ala Ser Gly Phe Asn Ile Glu Asp Tyr
            20                  25                  30

Tyr Ile Asn Trp Val Arg Gln Ala Thr Gly Gln Gly Leu Glu Trp Met
        35                  40                  45

Gly Arg Ile Asp Pro Glu Asp Gly Glu Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Leu Asp Pro Met Asp Tyr Trp Gly Gln Gly Thr
            100                 105                 110

Leu Val Thr Val Ser Ser
        115

```
<210> SEQ ID NO 91
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 91

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Glu Asp Tyr
            20                  25                  30

Tyr Met His Trp Val Arg Gln Ala Pro Glu Gln Gly Leu Glu Trp Met
        35                  40                  45

Gly Arg Ile Asp Pro Glu Asp Gly Glu Thr Thr Tyr Ala Pro Lys Phe
    50                  55                  60

Gln Gly Arg Val Thr Ser Thr Arg Asp Thr Ser Ile Asn Thr Ala Tyr
65                  70                  75                  80

Met Glu Leu Ser Arg Leu Arg Ser Asp Asp Thr Val Val Tyr Tyr Cys
                85                  90                  95

Ala Arg Ser Ile Tyr Leu Asp Pro Met Asp Tyr Trp Gly Gln Gly Thr
            100                 105                 110

Leu Val Thr Val Ser Ser
        115

<210> SEQ ID NO 92
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 92

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Glu Asp Tyr
            20                  25                  30

Tyr Met His Trp Val Arg Gln Ala Pro Glu Gln Gly Leu Glu Trp Met
        35                  40                  45

Gly Ile Ile Asp Pro Glu Asp Gly Glu Thr Ser Tyr Ala Gln Lys Phe
    50                  55                  60

Gln Gly Arg Val Thr Met Thr Arg Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Leu Asp Pro Met Asp Tyr Trp Gly Gln Gly Thr
            100                 105                 110

Leu Val Thr Val Ser Ser
        115

<210> SEQ ID NO 93
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 93

Asp Ile Gln Met Thr Gln Ser Pro Lys Ser Leu Ser Ala Ser Val Gly
1               5                   10                  15

```
Asp Arg Val Thr Ile Thr Cys Arg Ala Ser Gln Asp Val Thr Thr Ala
                20                  25                  30

Leu Ala Trp Tyr Gln Gln Lys Pro Gly Gln Ser Pro Lys Leu Leu Ile
            35                  40                  45

Tyr Trp Ala Thr Thr Arg His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Tyr
                85                  90                  95

Thr Phe Gly Gln Gly Thr Lys Leu Glu Ile Lys
                100                 105
```

<210> SEQ ID NO 94
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 94

```
Asp Ile Gln Met Thr Gln Ser Pro Lys Ser Val Ser Ala Ser Val Gly
1               5                   10                  15

Asp Arg Val Thr Ile Thr Cys Arg Ala Ser Gln Asp Val Thr Thr Ala
                20                  25                  30

Leu Ala Trp Tyr Gln Gln Lys Pro Gly Gln Ser Pro Lys Leu Leu Ile
            35                  40                  45

Tyr Trp Ala Thr Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Tyr
                85                  90                  95

Thr Phe Gly Gln Gly Thr Lys Leu Glu Ile Lys
                100                 105
```

<210> SEQ ID NO 95
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 95

```
Asp Ile Gln Met Thr Gln Ser Pro Lys Ser Leu Ser Ala Ser Val Gly
1               5                   10                  15

Asp Arg Val Thr Ile Thr Cys Gln Ala Ser Gln Asp Val Thr Thr Ala
                20                  25                  30

Leu Asn Trp Tyr Gln Gln Lys Pro Gly Lys Ala Pro Lys Leu Leu Ile
            35                  40                  45

Tyr Trp Ala Thr Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Thr Pro Tyr
```

```
                    85                  90                  95

Thr Phe Gly Gln Gly Thr Lys Leu Glu Ile Lys
                100                 105

<210> SEQ ID NO 96
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 96

Asp Ile Val Met Thr Gln Ser Pro Lys Ser Leu Ala Val Ser Leu Gly
1               5                   10                  15

Glu Arg Ala Thr Ile Asn Cys Lys Ser Ser Gln Asp Val Thr Thr Ala
            20                  25                  30

Leu Ala Trp Tyr Gln Gln Lys Pro Gly Gln Ser Pro Lys Leu Leu Ile
        35                  40                  45

Tyr Trp Ala Thr Thr Arg Glu Ser Gly Val Pro Asp Arg Phe Ser Gly
    50                  55                  60

Ser Gly Ser Gly Thr Asp Tyr Thr Leu Thr Ile Ser Ser Leu Gln Ala
65                  70                  75                  80

Glu Asp Val Ala Val Tyr Tyr Cys Gln Gln His Tyr Ser Thr Pro Tyr
                85                  90                  95

Thr Phe Gly Gln Gly Thr Lys Leu Glu Ile Lys
                100                 105

<210> SEQ ID NO 97
<211> LENGTH: 808
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 97

Met Pro Val Ala Glu Ala Pro Gln Val Ala Gly Gly Gln Gly Asp Gly
1               5                   10                  15

Gly Asp Gly Glu Glu Ala Glu Pro Glu Gly Met Phe Lys Ala Cys Glu
            20                  25                  30

Asp Ser Lys Arg Lys Ala Arg Gly Tyr Leu Arg Leu Val Pro Leu Phe
        35                  40                  45

Val Leu Leu Ala Leu Leu Val Leu Ala Ser Ala Gly Val Leu Leu Trp
    50                  55                  60

Tyr Phe Leu Gly Tyr Lys Ala Glu Val Met Val Ser Gln Val Tyr Ser
65                  70                  75                  80

Gly Ser Leu Arg Val Leu Asn Arg His Phe Ser Gln Asp Leu Thr Arg
                85                  90                  95

Arg Glu Ser Ser Ala Phe Arg Ser Glu Thr Ala Lys Ala Gln Lys Met
                100                 105                 110

Leu Lys Glu Leu Ile Thr Ser Thr Arg Leu Gly Thr Tyr Tyr Asn Ser
            115                 120                 125

Ser Ser Val Tyr Ser Phe Gly Glu Gly Pro Leu Thr Cys Phe Phe Trp
        130                 135                 140

Phe Ile Leu Gln Ile Pro Glu His Arg Arg Leu Met Leu Ser Pro Glu
145                 150                 155                 160
```

```
Val Val Gln Ala Leu Leu Val Glu Glu Leu Ser Thr Val Asn Ser
            165                 170                 175

Ser Ala Ala Val Pro Tyr Arg Ala Glu Tyr Glu Val Asp Pro Glu Gly
                180                 185                 190

Leu Val Ile Leu Glu Ala Ser Val Lys Asp Ile Ala Ala Leu Asn Ser
            195                 200                 205

Thr Leu Gly Cys Tyr Arg Tyr Ser Tyr Val Gly Gln Gly Gln Val Leu
            210                 215                 220

Arg Leu Lys Gly Pro Asp His Leu Ala Ser Ser Cys Leu Trp His Leu
225                 230                 235                 240

Gln Gly Pro Lys Asp Leu Met Leu Lys Leu Arg Leu Glu Trp Thr Leu
                245                 250                 255

Ala Glu Cys Arg Asp Arg Leu Ala Met Tyr Asp Val Ala Gly Pro Leu
            260                 265                 270

Glu Lys Arg Leu Ile Thr Ser Val Tyr Gly Cys Ser Arg Gln Glu Pro
            275                 280                 285

Val Val Glu Val Leu Ala Ser Gly Ala Ile Met Ala Val Val Trp Lys
            290                 295                 300

Lys Gly Leu His Ser Tyr Tyr Asp Pro Phe Val Leu Ser Val Gln Pro
305                 310                 315                 320

Val Val Phe Gln Ala Cys Glu Val Asn Leu Thr Leu Asp Asn Arg Leu
            325                 330                 335

Asp Ser Gln Gly Val Leu Ser Thr Pro Tyr Phe Pro Ser Tyr Tyr Ser
            340                 345                 350

Pro Gln Thr His Cys Ser Trp His Leu Thr Val Pro Ser Leu Asp Tyr
            355                 360                 365

Gly Leu Ala Leu Trp Phe Asp Ala Tyr Ala Leu Arg Arg Gln Lys Tyr
            370                 375                 380

Asp Leu Pro Cys Thr Gln Gly Gln Trp Thr Ile Gln Asn Arg Arg Leu
385                 390                 395                 400

Cys Gly Leu Arg Ile Leu Gln Pro Tyr Ala Glu Arg Ile Pro Val Val
            405                 410                 415

Ala Thr Ala Gly Ile Thr Ile Asn Phe Thr Ser Gln Ile Ser Leu Thr
            420                 425                 430

Gly Pro Gly Val Arg Val His Tyr Gly Leu Tyr Asn Gln Ser Asp Pro
            435                 440                 445

Cys Pro Gly Glu Phe Leu Cys Ser Val Asn Gly Leu Cys Val Pro Ala
            450                 455                 460

Cys Asp Gly Val Lys Asp Cys Pro Asn Gly Leu Asp Glu Arg Asn Cys
465                 470                 475                 480

Val Cys Arg Ala Thr Phe Gln Cys Lys Glu Asp Ser Thr Cys Ile Ser
            485                 490                 495

Leu Pro Lys Val Cys Asp Gly Gln Pro Asp Cys Leu Asn Gly Ser Asp
            500                 505                 510

Glu Glu Gln Cys Gln Glu Gly Val Pro Cys Gly Thr Phe Thr Phe Gln
            515                 520                 525

Cys Glu Asp Arg Ser Cys Val Lys Lys Pro Asn Pro Gln Cys Asp Gly
            530                 535                 540

Arg Pro Asp Cys Arg Asp Gly Ser Asp Glu Glu His Cys Asp Cys Gly
545                 550                 555                 560

Leu Gln Gly Pro Ser Ser Arg Ile Val Gly Gly Ala Val Ser Ser Glu
            565                 570                 575
```

Gly Glu Trp Pro Trp Gln Ala Ser Leu Gln Val Arg Gly Arg His Ile
            580                 585                 590

Cys Gly Gly Ala Leu Ile Ala Asp Arg Trp Val Ile Thr Ala Ala His
        595                 600                 605

Cys Phe Gln Glu Asp Ser Met Ala Ser Thr Val Leu Trp Thr Val Phe
    610                 615                 620

Leu Gly Lys Val Trp Gln Asn Ser Arg Trp Pro Gly Glu Val Ser Phe
625                 630                 635                 640

Lys Val Ser Arg Leu Leu His Pro Tyr His Glu Asp Ser His
                645                 650                 655

Asp Tyr Asp Val Ala Leu Leu Gln Leu Asp His Pro Val Val Arg Ser
            660                 665                 670

Ala Ala Val Arg Pro Val Cys Leu Pro Ala Arg Ser His Phe Phe Glu
        675                 680                 685

Pro Gly Leu His Cys Trp Ile Thr Gly Trp Gly Ala Leu Arg Glu Gly
    690                 695                 700

Gly Pro Ile Ser Asn Ala Leu Gln Lys Val Asp Val Gln Leu Ile Pro
705                 710                 715                 720

Gln Asp Leu Cys Ser Glu Val Tyr Arg Tyr Gln Val Thr Pro Arg Met
                725                 730                 735

Leu Cys Ala Gly Tyr Arg Lys Gly Lys Lys Asp Ala Cys Gln Gly Asp
            740                 745                 750

Ser Gly Gly Pro Leu Val Cys Lys Ala Leu Ser Gly Arg Trp Phe Leu
        755                 760                 765

Ala Gly Leu Val Ser Trp Gly Leu Gly Cys Gly Arg Pro Asn Tyr Phe
    770                 775                 780

Gly Val Tyr Thr Arg Ile Thr Gly Val Ile Ser Trp Ile Gln Gln Val
785                 790                 795                 800

Val Thr His His His His His His
                805

<210> SEQ ID NO 98
<211> LENGTH: 817
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 98

Met Pro Arg Cys Phe Gln Leu Pro Cys Ser Thr Arg Met Pro Thr Thr
1               5                   10                  15

Glu Val Pro Gln Ala Ala Asp Gly Gln Gly Asp Ala Gly Asp Gly Glu
            20                  25                  30

Glu Ala Ala Glu Pro Glu Gly Lys Phe Lys Pro Pro Lys Asn Thr Lys
        35                  40                  45

Arg Lys Asn Arg Asp Tyr Val Arg Phe Thr Pro Leu Leu Leu Val Leu
    50                  55                  60

Ala Ala Leu Val Ser Ala Gly Val Met Leu Trp Tyr Phe Leu Gly Tyr
65                  70                  75                  80

Lys Ala Glu Val Thr Val Ser Gln Val Tyr Ser Gly Ser Leu Arg Val
                85                  90                  95

Leu Asn Arg His Phe Ser Gln Asp Leu Gly Arg Arg Glu Ser Ile Ala
            100                 105                 110

Phe Arg Ser Glu Ser Ala Lys Ala Gln Lys Met Leu Gln Glu Leu Val

```
              115                 120                 125
Ala Ser Thr Arg Leu Gly Thr Tyr Tyr Asn Ser Ser Val Tyr Ser
130                 135                 140

Phe Gly Glu Gly Pro Leu Thr Cys Phe Phe Trp Phe Ile Leu Asp Ile
145                 150                 155                 160

Pro Glu Tyr Gln Arg Leu Thr Leu Ser Pro Glu Val Val Arg Glu Leu
                165                 170                 175

Leu Val Asp Glu Leu Leu Ser Asn Ser Ser Thr Leu Ala Ser Tyr Lys
                180                 185                 190

Thr Glu Tyr Glu Val Asp Pro Glu Gly Leu Val Ile Leu Glu Ala Ser
                195                 200                 205

Val Asn Asp Ile Val Val Leu Asn Ser Thr Leu Gly Cys Tyr Arg Tyr
210                 215                 220

Ser Tyr Val Asn Pro Gly Gln Val Leu Pro Leu Lys Gly Pro Asp Gln
225                 230                 235                 240

Gln Thr Thr Ser Cys Leu Trp His Leu Gln Gly Pro Glu Asp Leu Met
                245                 250                 255

Ile Lys Val Arg Leu Glu Trp Thr Arg Val Asp Cys Arg Asp Arg Val
                260                 265                 270

Ala Met Tyr Asp Ala Ala Gly Pro Leu Glu Lys Arg Leu Ile Thr Ser
                275                 280                 285

Val Tyr Gly Cys Ser Arg Gln Glu Pro Val Met Glu Val Leu Ala Ser
                290                 295                 300

Gly Ser Val Met Ala Val Val Trp Lys Lys Gly Met His Ser Tyr Tyr
305                 310                 315                 320

Asp Pro Phe Leu Leu Ser Val Lys Ser Val Ala Phe Gln Asp Cys Gln
                325                 330                 335

Val Asn Leu Thr Leu Glu Gly Arg Leu Asp Thr Gln Gly Phe Leu Arg
                340                 345                 350

Thr Pro Tyr Tyr Pro Ser Tyr Tyr Ser Pro Ser Thr His Cys Ser Trp
                355                 360                 365

His Leu Thr Val Pro Ser Leu Asp Tyr Gly Leu Ala Leu Trp Phe Asp
                370                 375                 380

Ala Tyr Ala Leu Arg Arg Gln Lys Tyr Asn Arg Leu Cys Thr Gln Gly
385                 390                 395                 400

Gln Trp Met Ile Gln Asn Arg Arg Leu Cys Gly Phe Arg Thr Leu Gln
                405                 410                 415

Pro Tyr Ala Glu Arg Ile Pro Met Val Ala Ser Asp Gly Val Thr Ile
                420                 425                 430

Asn Phe Thr Ser Gln Ile Ser Leu Thr Gly Pro Gly Val Gln Val Tyr
                435                 440                 445

Tyr Ser Leu Tyr Asn Gln Ser Asp Pro Cys Pro Gly Glu Phe Leu Cys
                450                 455                 460

Ser Val Asn Gly Leu Cys Val Pro Ala Cys Asp Gly Ile Lys Asp Cys
465                 470                 475                 480

Pro Asn Gly Leu Asp Glu Arg Asn Cys Val Cys Arg Ala Met Phe Gln
                485                 490                 495

Cys Gln Glu Asp Ser Thr Cys Ile Ser Leu Pro Arg Val Cys Asp Arg
                500                 505                 510

Gln Pro Asp Cys Leu Asn Gly Ser Asp Glu Glu Gln Cys Gln Glu Gly
                515                 520                 525

Val Pro Cys Gly Thr Phe Thr Phe Gln Cys Glu Asp Arg Ser Cys Val
530                 535                 540
```

```
Lys Lys Pro Asn Pro Glu Cys Asp Gly Gln Ser Asp Cys Arg Asp Gly
545                 550                 555                 560

Ser Asp Glu Gln His Cys Asp Cys Gly Leu Gln Gly Leu Ser Ser Arg
            565                 570                 575

Ile Val Gly Gly Thr Val Ser Ser Glu Gly Glu Trp Pro Trp Gln Ala
            580                 585                 590

Ser Leu Gln Ile Arg Gly Arg His Ile Cys Gly Gly Ala Leu Ile Ala
            595                 600                 605

Asp Arg Trp Val Ile Thr Ala Ala His Cys Phe Gln Glu Asp Ser Met
610                 615                 620

Ala Ser Pro Lys Leu Trp Thr Val Phe Leu Gly Lys Met Arg Gln Asn
625                 630                 635                 640

Ser Arg Trp Pro Gly Glu Val Ser Phe Lys Val Ser Arg Leu Phe Leu
            645                 650                 655

His Pro Tyr His Glu Glu Asp Ser His Asp Tyr Asp Val Ala Leu Leu
            660                 665                 670

Gln Leu Asp His Pro Val Val Tyr Ser Ala Thr Val Arg Pro Val Cys
            675                 680                 685

Leu Pro Ala Arg Ser His Phe Phe Glu Pro Gly Gln His Cys Trp Ile
690                 695                 700

Thr Gly Trp Gly Ala Gln Arg Glu Gly Gly Pro Val Ser Asn Thr Leu
705                 710                 715                 720

Gln Lys Val Asp Val Gln Leu Val Pro Gln Asp Leu Cys Ser Glu Ala
            725                 730                 735

Tyr Arg Tyr Gln Val Ser Pro Arg Met Leu Cys Ala Gly Tyr Arg Lys
            740                 745                 750

Gly Lys Lys Asp Ala Cys Gln Gly Asp Ser Gly Gly Pro Leu Val Cys
            755                 760                 765

Arg Glu Pro Ser Gly Arg Trp Phe Leu Ala Gly Leu Val Ser Trp Gly
770                 775                 780

Leu Gly Cys Gly Arg Pro Asn Phe Phe Gly Val Tyr Thr Arg Val Thr
785                 790                 795                 800

Arg Val Ile Asn Trp Ile Gln Gln Val Leu Thr His His His His His
            805                 810                 815

His

<210> SEQ ID NO 99
<211> LENGTH: 806
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 99

Met Pro Val Ala Lys Ala Pro Gln Val Ala Gly Gln Gly Asp Gly
1               5                   10                  15

Gly Asp Gly Glu Glu Ala Glu Pro Gly Met Phe Glu Ala Cys Glu
                20                  25                  30

Asp Ser Lys Arg Lys Ala Arg Gly Tyr Leu Arg Leu Ala Pro Leu Trp
            35                  40                  45

Leu Thr Leu Val Val Leu Thr Ser Val Gly Val Leu Leu Trp Tyr Phe
50                  55                  60

Leu Gly Tyr Lys Ala Glu Val Thr Val Ser Gln Val Tyr Ser Gly Ser
```

```
                65                  70                  75                  80
Leu Arg Val Leu Asn Arg His Phe Ser Gln Asp Leu Thr Arg Glu
                    85                  90                  95

Ser Ser Ala Phe Arg Ser Glu Thr Ala Lys Ala Gln Lys Met Leu Lys
                   100                 105                 110

Glu Leu Ile Ala Ser Thr Arg Leu Gly Thr Tyr Tyr Asn Ser Ser Ser
                   115                 120                 125

Val Tyr Ser Phe Gly Glu Gly Pro Leu Thr Cys Phe Phe Trp Phe Ile
        130                 135                 140

Leu Gln Ile Pro Glu His Arg Arg Leu Met Leu Ser Pro Glu Val Val
145                 150                 155                 160

Gln Ala Leu Leu Val Glu Glu Leu Leu Ser Thr Val Asn Ser Ser Ala
                165                 170                 175

Ala Val Pro Tyr Arg Ala Glu Tyr Glu Val Asp Pro Glu Gly Leu Val
                180                 185                 190

Ile Leu Glu Ala Ser Val Lys Asp Ile Ala Ala Leu Asn Ser Thr Leu
                195                 200                 205

Gly Cys Tyr Arg Tyr Ser Tyr Val Gly Gln Gly Gln Val Leu Arg Leu
        210                 215                 220

Lys Gly Pro Asp His Leu Ala Ser Ser Cys Leu Trp His Leu Gln Gly
225                 230                 235                 240

Pro Glu Asp Leu Met Leu Lys Leu Arg Leu Glu Trp Thr Leu Ala Glu
                245                 250                 255

Cys Arg Asp Arg Leu Ala Met Tyr Asp Val Ala Gly Pro Leu Glu Lys
                260                 265                 270

Arg Leu Ile Thr Ser Val Tyr Gly Cys Ser Arg Gln Glu Pro Val Val
            275                 280                 285

Glu Val Leu Ala Ser Gly Ala Ile Met Ala Val Val Trp Lys Lys Gly
            290                 295                 300

Leu His Ser Tyr Tyr Asp Pro Phe Met Leu Ser Val Gln Ser Val Val
305                 310                 315                 320

Phe Gln Ala Cys Glu Val Asn Leu Thr Leu Asp Asp Arg Leu Asp Ser
                325                 330                 335

Gln Gly Val Leu Ser Thr Pro Tyr Phe Pro Ser Tyr Tyr Ser Pro Arg
                340                 345                 350

Thr His Cys Ser Trp His Leu Thr Val Pro Ser Leu Asp Tyr Gly Leu
            355                 360                 365

Ala Leu Trp Phe Asp Ala Tyr Ala Leu Arg Arg Gln Lys Tyr Asp Leu
        370                 375                 380

Pro Cys Thr Gln Gly Gln Trp Thr Ile Gln Asn Arg Arg Leu Cys Gly
385                 390                 395                 400

Leu Arg Ile Leu Gln Pro Tyr Ala Glu Arg Ile Pro Val Val Ala Thr
                405                 410                 415

Ala Gly Ile Thr Ile Asn Phe Thr Ser Gln Ile Ser Leu Thr Gly Pro
                420                 425                 430

Gly Val Arg Val His Tyr Gly Leu Tyr Asn Gln Ser Asp Pro Cys Pro
            435                 440                 445

Gly Glu Phe Leu Cys Ser Val Asn Gly Leu Cys Val Pro Ala Cys Asp
        450                 455                 460

Gly Val Lys Asp Cys Pro Asn Gly Leu Asp Glu Arg Asn Cys Val Cys
465                 470                 475                 480

Arg Ala Thr Phe Gln Cys Gln Glu Asp Ser Thr Cys Ile Ser Leu Leu
                485                 490                 495
```

Lys Val Cys Asp Gly Gln Pro Asp Cys Leu Asn Gly Ser Asp Glu Glu
            500                 505                 510

Arg Cys Gln Glu Gly Val Pro Cys Gly Thr Phe Thr Phe Gln Cys Glu
        515                 520                 525

Asp Gln Ser Cys Val Lys Lys Pro Asn Pro Gln Cys Asp Gly Arg Pro
    530                 535                 540

Asp Cys Arg Asp Gly Ser Asp Glu Gln His Cys Asp Cys Gly Leu Gln
545                 550                 555                 560

Gly Pro Ser Ser Arg Ile Val Gly Ala Val Ser Ser Glu Gly Glu
            565                 570                 575

Trp Pro Trp Gln Ala Ser Leu Gln Val Arg Gly Arg His Ile Cys Gly
        580                 585                 590

Gly Ala Leu Ile Ala Asp Arg Trp Val Ile Thr Ala Ala His Cys Phe
    595                 600                 605

Gln Glu Asp Ser Met Ala Ser Pro Ala Leu Trp Thr Val Phe Leu Gly
610                 615                 620

Lys Val Trp Gln Asn Ser Arg Trp Pro Gly Glu Val Ser Phe Lys Val
625                 630                 635                 640

Ser Arg Leu Leu Leu His Pro Tyr His Glu Glu Asp Ser His Asp Tyr
            645                 650                 655

Asp Val Ala Leu Leu Gln Leu Asp His Pro Val Val Arg Ser Ala Ala
        660                 665                 670

Val Arg Pro Val Cys Leu Pro Ala Arg Ser His Phe Phe Glu Pro Gly
    675                 680                 685

Leu His Cys Trp Ile Thr Gly Trp Gly Ala Leu Arg Glu Gly Gly Pro
690                 695                 700

Thr Ser Asn Ala Leu Gln Lys Val Asp Val Gln Leu Ile Pro Gln Asp
705                 710                 715                 720

Leu Cys Ser Glu Ala Tyr Arg Tyr Gln Val Thr Pro Arg Met Leu Cys
            725                 730                 735

Ala Gly Tyr Arg Lys Gly Lys Lys Asp Ala Cys Gln Gly Asp Ser Gly
        740                 745                 750

Gly Pro Leu Val Cys Lys Ala Leu Ser Gly Arg Trp Phe Leu Ala Gly
    755                 760                 765

Leu Val Ser Trp Gly Leu Gly Cys Gly Arg Pro Asn Tyr Phe Gly Val
770                 775                 780

Tyr Thr Arg Ile Thr Gly Val Ile Gly Trp Ile Gln Gln Val Val Thr
785                 790                 795                 800

His His His His His His
            805

<210> SEQ ID NO 100
<211> LENGTH: 860
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 100

Met Gly Ser Asp Arg Ala Arg Lys Gly Gly Gly Pro Lys Asp Phe
1               5                   10                  15

Gly Ala Gly Leu Lys Tyr Asn Ser Arg His Glu Lys Val Asn Gly Leu
            20                  25                  30

-continued

Glu Glu Gly Val Glu Phe Leu Pro Val Asn Asn Val Lys Lys Val Glu
         35                  40                  45

Lys His Gly Pro Gly Arg Trp Val Val Leu Ala Ala Val Leu Ile Gly
 50                  55                  60

Leu Leu Leu Val Leu Leu Gly Ile Gly Phe Leu Val Trp His Leu Gln
 65                  70                  75                  80

Tyr Arg Asp Val Arg Val Gln Lys Val Phe Asn Gly Tyr Met Arg Ile
                 85                  90                  95

Thr Asn Glu Asn Phe Val Asp Ala Tyr Glu Asn Ser Asn Ser Thr Glu
            100                 105                 110

Phe Val Ser Leu Ala Ser Lys Val Lys Asp Ala Leu Lys Leu Leu Tyr
            115                 120                 125

Ser Gly Val Pro Phe Leu Gly Pro Tyr His Lys Glu Ser Ala Val Thr
        130                 135                 140

Ala Phe Ser Glu Gly Ser Val Ile Ala Tyr Tyr Trp Ser Glu Phe Ser
145                 150                 155                 160

Ile Pro Gln His Leu Val Glu Glu Ala Glu Arg Val Met Ala Glu Glu
                165                 170                 175

Arg Val Val Met Leu Pro Pro Arg Ala Arg Ser Leu Lys Ser Phe Val
            180                 185                 190

Val Thr Ser Val Val Ala Phe Pro Thr Asp Ser Lys Thr Val Gln Arg
        195                 200                 205

Thr Gln Asp Asn Ser Cys Ser Phe Gly Leu His Ala Arg Gly Val Glu
    210                 215                 220

Leu Met Arg Phe Thr Thr Pro Gly Phe Pro Asp Ser Pro Tyr Pro Ala
225                 230                 235                 240

His Ala Arg Cys Gln Trp Ala Leu Arg Gly Asp Ala Asp Ser Val Leu
                245                 250                 255

Ser Leu Thr Phe Arg Ser Phe Asp Leu Ala Ser Cys Asp Glu Arg Gly
            260                 265                 270

Ser Asp Leu Val Thr Val Tyr Asn Thr Leu Ser Pro Met Glu Pro His
        275                 280                 285

Ala Leu Val Gln Leu Cys Gly Thr Tyr Pro Pro Ser Tyr Asn Leu Thr
    290                 295                 300

Phe His Ser Ser Gln Asn Val Leu Leu Ile Thr Leu Ile Thr Asn Thr
305                 310                 315                 320

Glu Arg Arg His Pro Gly Phe Glu Ala Thr Phe Phe Gln Leu Pro Arg
                325                 330                 335

Met Ser Ser Cys Gly Gly Arg Leu Arg Lys Ala Gln Gly Thr Phe Asn
            340                 345                 350

Ser Pro Tyr Tyr Pro Gly His Tyr Pro Pro Asn Ile Asp Cys Thr Trp
        355                 360                 365

Asn Ile Glu Val Pro Asn Asn Gln His Val Lys Val Arg Phe Lys Phe
    370                 375                 380

Phe Tyr Leu Leu Glu Pro Gly Val Pro Ala Gly Thr Cys Pro Lys Asp
385                 390                 395                 400

Tyr Val Glu Ile Asn Gly Glu Lys Tyr Cys Gly Glu Arg Ser Gln Phe
                405                 410                 415

Val Val Thr Ser Asn Ser Asn Lys Ile Thr Val Arg Phe His Ser Asp
            420                 425                 430

Gln Ser Tyr Thr Asp Thr Gly Phe Leu Ala Glu Tyr Leu Ser Tyr Asp
        435                 440                 445

Ser Ser Asp Pro Cys Pro Gly Gln Phe Thr Cys Arg Thr Gly Arg Cys

```
            450                 455                 460
Ile Arg Lys Glu Leu Arg Cys Asp Gly Trp Ala Asp Cys Thr Asp His
465                 470                 475                 480

Ser Asp Glu Leu Asn Cys Ser Cys Asp Ala Gly His Gln Phe Thr Cys
                    485                 490                 495

Lys Asn Lys Phe Cys Lys Pro Leu Phe Trp Val Cys Asp Ser Val Asn
                500                 505                 510

Asp Cys Gly Asp Asn Ser Asp Glu Gln Gly Cys Ser Cys Pro Ala Gln
                515                 520                 525

Thr Phe Arg Cys Ser Asn Gly Lys Cys Leu Ser Lys Ser Gln Gln Cys
                530                 535                 540

Asn Gly Lys Asp Asp Cys Gly Asp Gly Ser Asp Glu Ala Ser Cys Pro
545                 550                 555                 560

Lys Val Asn Val Val Thr Cys Thr Lys His Thr Tyr Arg Cys Leu Asn
                    565                 570                 575

Gly Leu Cys Leu Ser Lys Gly Asn Pro Glu Cys Asp Gly Lys Glu Asp
                580                 585                 590

Cys Ser Asp Gly Ser Asp Glu Lys Asp Cys Asp Cys Gly Leu Arg Ser
                595                 600                 605

Phe Thr Arg Gln Ala Arg Val Val Gly Gly Thr Asp Ala Asp Glu Gly
                610                 615                 620

Glu Trp Trp Gln Val Ser Leu His Ala Leu Gly Gln Gly His Ile Cys
625                 630                 635                 640

Gly Ala Ser Leu Ile Ser Pro Asn Trp Leu Val Ser Ala Ala His Cys
                    645                 650                 655

Tyr Ile Asp Asp Arg Gly Phe Arg Tyr Ser Asp Pro Thr Gln Trp Thr
                660                 665                 670

Ala Phe Leu Gly Leu His Asp Gln Ser Gln Arg Ser Ala Pro Gly Val
                675                 680                 685

Gln Glu Arg Arg Leu Lys Arg Ile Ile Ser His Pro Phe Phe Asn Asp
                690                 695                 700

Phe Thr Phe Asp Tyr Asp Ile Ala Leu Leu Glu Leu Glu Lys Pro Ala
705                 710                 715                 720

Glu Tyr Ser Ser Met Val Arg Pro Ile Cys Leu Pro Asp Ala Ser His
                    725                 730                 735

Val Phe Pro Ala Gly Lys Ala Ile Trp Val Thr Gly Trp Gly His Thr
                740                 745                 750

Gln Tyr Gly Gly Thr Gly Ala Leu Ile Leu Gln Lys Gly Glu Ile Arg
                755                 760                 765

Val Ile Asn Gln Thr Thr Cys Glu Asn Leu Leu Pro Gln Gln Ile Thr
                770                 775                 780

Pro Arg Met Met Cys Val Gly Phe Leu Ser Gly Gly Val Asp Ser Cys
785                 790                 795                 800

Gln Gly Asp Ser Gly Gly Pro Leu Ser Ser Val Glu Ala Asp Gly Arg
                805                 810                 815

Ile Phe Gln Ala Gly Val Val Ser Trp Gly Asp Gly Cys Ala Gln Arg
                820                 825                 830

Asn Lys Pro Gly Val Tyr Thr Arg Leu Pro Leu Phe Arg Asp Trp Ile
                835                 840                 845

Lys Glu Asn Thr Gly Val His His His His His
850                 855                 860

<210> SEQ ID NO 101
```

-continued

```
<211> LENGTH: 849
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 101

Met Asp Lys Glu Asn Ser Asp Val Ser Ala Ala Pro Ala Asp Leu Lys
1               5                   10                  15

Ile Ser Asn Ile Ser Val Gln Val Val Ser Ala Gln Lys Lys Leu Pro
            20                  25                  30

Val Arg Arg Pro Pro Leu Pro Gly Arg Arg Leu Pro Leu Pro Gly Arg
        35                  40                  45

Arg Pro Pro Gln Arg Pro Ile Gly Lys Ala Lys Pro Lys Lys Gln Ser
    50                  55                  60

Lys Lys Lys Val Pro Phe Trp Asn Val Gln Asn Lys Ile Ile Leu Phe
65              70                  75                  80

Thr Val Phe Leu Phe Ile Leu Ala Val Ile Ala Trp Thr Leu Leu Trp
                85                  90                  95

Leu Tyr Ile Ser Lys Thr Glu Ser Lys Asp Ala Phe Tyr Phe Ala Gly
            100                 105                 110

Met Phe Arg Ile Thr Asn Ile Glu Phe Leu Pro Glu Tyr Arg Gln Lys
        115                 120                 125

Glu Ser Arg Glu Phe Leu Ser Val Ser Arg Thr Val Gln Gln Val Ile
    130                 135                 140

Asn Leu Val Tyr Thr Thr Ser Ala Phe Ser Lys Phe Tyr Glu Gln Ser
145                 150                 155                 160

Val Val Ala Asp Val Ser Ser Asn Asn Lys Gly Gly Leu Leu Val His
                165                 170                 175

Phe Trp Ile Val Phe Val Met Pro Arg Ala Lys Gly His Ile Phe Cys
            180                 185                 190

Glu Asp Cys Val Ala Ala Ile Leu Lys Asp Ser Ile Gln Thr Ser Ile
        195                 200                 205

Ile Asn Arg Thr Ser Val Gly Ser Leu Gln Gly Leu Ala Val Asp Met
    210                 215                 220

Asp Ser Val Val Leu Asn Ala Gly Leu Arg Ser Asp Tyr Ser Ser Thr
225                 230                 235                 240

Ile Gly Ser Asp Lys Gly Cys Ser Gln Tyr Phe Tyr Ala Glu His Leu
                245                 250                 255

Ser Leu His Tyr Pro Leu Glu Ile Ser Ala Ala Ser Gly Arg Leu Met
            260                 265                 270

Cys His Phe Lys Leu Val Ala Ile Val Gly Tyr Leu Ile Arg Leu Ser
        275                 280                 285

Ile Lys Ser Ile Gln Ile Glu Ala Asp Asn Cys Val Thr Asp Ser Leu
    290                 295                 300

Thr Ile Tyr Asp Ser Leu Leu Pro Ile Arg Ser Ser Ile Leu Tyr Arg
305                 310                 315                 320

Ile Cys Glu Pro Thr Arg Thr Leu Met Ser Phe Val Ser Thr Asn Asn
                325                 330                 335

Leu Met Leu Val Thr Phe Lys Ser Pro His Ile Arg Arg Leu Ser Gly
            340                 345                 350

Ile Arg Ala Tyr Phe Glu Val Ile Pro Glu Gln Lys Cys Glu Asn Thr
        355                 360                 365
```

```
Val Leu Val Lys Asp Ile Thr Gly Phe Glu Gly Lys Ile Ser Ser Pro
            370                 375                 380

Tyr Tyr Pro Ser Tyr Tyr Pro Pro Lys Cys Lys Cys Thr Trp Lys Phe
385                 390                 395                 400

Gln Thr Ser Leu Ser Thr Leu Gly Ile Ala Leu Lys Phe Tyr Asn Tyr
                405                 410                 415

Ser Ile Thr Lys Lys Ser Met Lys Gly Cys Glu His Gly Trp Trp Glu
            420                 425                 430

Ile Asn Glu His Met Tyr Cys Gly Ser Tyr Met Asp His Gln Thr Ile
            435                 440                 445

Phe Arg Val Pro Ser Pro Leu Val His Ile Gln Leu Gln Cys Ser Ser
450                 455                 460

Arg Leu Ser Asp Lys Pro Leu Leu Ala Glu Tyr Gly Ser Tyr Asn Ile
465                 470                 475                 480

Ser Gln Pro Cys Pro Val Gly Ser Phe Arg Cys Ser Ser Gly Leu Cys
                485                 490                 495

Val Pro Gln Ala Gln Arg Cys Asp Gly Val Asn Asp Cys Phe Asp Glu
            500                 505                 510

Ser Asp Glu Leu Phe Cys Val Ser Pro Gln Pro Ala Cys Asn Thr Ser
            515                 520                 525

Ser Phe Arg Gln His Gly Pro Leu Ile Cys Asp Gly Phe Arg Asp Cys
530                 535                 540

Glu Asn Gly Arg Asp Glu Gln Asn Cys Thr Gln Ser Ile Pro Cys Asn
545                 550                 555                 560

Asn Arg Thr Phe Lys Cys Gly Asn Asp Ile Cys Phe Arg Lys Gln Asn
                565                 570                 575

Ala Lys Cys Asp Gly Thr Val Asp Cys Pro Asp Gly Ser Asp Glu Glu
            580                 585                 590

Gly Cys Thr Cys Ser Arg Ser Ser Ala Leu His Arg Ile Ile Gly
            595                 600                 605

Gly Thr Asp Thr Leu Glu Gly Gly Trp Pro Trp Gln Val Ser Leu His
            610                 615                 620

Phe Val Gly Ser Ala Tyr Cys Gly Ala Ser Val Ile Ser Arg Glu Trp
625                 630                 635                 640

Leu Leu Ser Ala Ala His Cys Phe His Gly Asn Arg Leu Ser Asp Pro
                645                 650                 655

Thr Pro Trp Thr Ala His Leu Gly Met Tyr Val Gln Gly Asn Ala Lys
            660                 665                 670

Phe Val Ser Pro Val Arg Arg Ile Val Val His Glu Tyr Tyr Asn Ser
            675                 680                 685

Gln Thr Phe Asp Tyr Asp Ile Ala Leu Leu Gln Leu Ser Ile Ala Trp
690                 695                 700

Pro Glu Thr Leu Lys Gln Leu Ile Gln Pro Ile Cys Ile Pro Pro Thr
705                 710                 715                 720

Gly Gln Arg Val Arg Ser Gly Glu Lys Cys Trp Val Thr Gly Trp Gly
                725                 730                 735

Arg Arg His Glu Ala Asp Asn Lys Gly Ser Leu Val Leu Gln Gln Ala
            740                 745                 750

Glu Val Glu Leu Ile Asp Gln Thr Leu Cys Val Ser Thr Tyr Gly Ile
            755                 760                 765

Ile Thr Ser Arg Met Leu Cys Ala Gly Ile Met Ser Gly Lys Arg Asp
770                 775                 780

Ala Cys Lys Gly Asp Ser Gly Gly Pro Leu Ser Cys Arg Arg Lys Ser
```

```
785                 790                 795                 800
Asp Gly Lys Trp Ile Leu Thr Gly Ile Val Ser Trp Gly His Gly Ser
                805                 810                 815

Gly Arg Pro Asn Phe Pro Gly Val Tyr Thr Arg Val Ser Asn Phe Val
                820                 825                 830

Pro Trp Ile His Lys Tyr Val Pro Ser Leu Leu His His His His His
                835                 840                 845

His

<210> SEQ ID NO 102
<211> LENGTH: 783
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 102

Met Asp Met Arg Val Pro Ala Gln Leu Leu Gly Leu Leu Leu Leu Trp
1               5                   10                  15

Leu Pro Gly Ala Arg Gly Ala Asp Ile Gly Tyr Lys Ala Glu Val Met
                20                  25                  30

Val Ser Gln Val Tyr Ser Gly Ser Leu Arg Val Leu Asn Arg His Phe
            35                  40                  45

Ser Gln Asp Leu Thr Arg Arg Glu Ser Ser Ala Phe Arg Ser Glu Thr
        50                  55                  60

Ala Lys Ala Gln Lys Met Leu Lys Glu Leu Ile Thr Ser Thr Arg Leu
65                  70                  75                  80

Gly Thr Tyr Tyr Asn Ser Ser Ser Val Tyr Ser Phe Gly Glu Gly Pro
                85                  90                  95

Leu Thr Cys Phe Phe Trp Phe Ile Leu Gln Ile Pro Glu His Arg Arg
                100                 105                 110

Leu Met Leu Ser Pro Glu Val Gln Ala Leu Leu Val Glu Glu Leu
            115                 120                 125

Leu Ser Thr Val Asn Ser Ser Ala Ala Val Pro Tyr Arg Ala Glu Tyr
        130                 135                 140

Glu Val Asp Pro Glu Gly Leu Val Ile Leu Glu Ala Ser Val Lys Asp
145                 150                 155                 160

Ile Ala Ala Leu Asn Ser Thr Leu Gly Cys Tyr Arg Tyr Ser Tyr Val
                165                 170                 175

Gly Gln Gly Gln Val Leu Arg Leu Lys Gly Pro Asp His Leu Ala Ser
            180                 185                 190

Ser Cys Leu Trp His Leu Gln Gly Pro Lys Asp Leu Met Leu Lys Leu
        195                 200                 205

Arg Leu Glu Trp Thr Leu Ala Glu Cys Arg Asp Arg Leu Ala Met Tyr
    210                 215                 220

Asp Val Ala Gly Pro Leu Glu Lys Arg Leu Ile Thr Ser Val Tyr Gly
225                 230                 235                 240

Cys Ser Arg Gln Glu Pro Val Val Glu Val Leu Ala Ser Gly Ala Ile
                245                 250                 255

Met Ala Val Val Trp Lys Lys Gly Leu His Ser Tyr Tyr Asp Pro Phe
            260                 265                 270

Val Leu Ser Val Gln Pro Val Val Phe Gln Ala Cys Glu Val Asn Leu
        275                 280                 285
```

```
Thr Leu Asp Asn Arg Leu Asp Ser Gln Gly Val Leu Ser Thr Pro Tyr
    290                 295                 300
Phe Pro Ser Tyr Tyr Ser Pro Gln Thr His Cys Ser Trp His Leu Thr
305                 310                 315                 320
Val Pro Ser Leu Asp Tyr Gly Leu Ala Leu Trp Phe Asp Ala Tyr Ala
                325                 330                 335
Leu Arg Arg Gln Lys Tyr Asp Leu Pro Cys Thr Gln Gly Gln Trp Thr
            340                 345                 350
Ile Gln Asn Arg Arg Leu Cys Gly Leu Arg Ile Leu Gln Pro Tyr Ala
        355                 360                 365
Glu Arg Ile Pro Val Val Ala Thr Ala Gly Ile Thr Ile Asn Phe Thr
370                 375                 380
Ser Gln Ile Ser Leu Thr Gly Pro Gly Val Arg Val His Tyr Gly Leu
385                 390                 395                 400
Tyr Asn Gln Ser Asp Pro Cys Pro Gly Glu Phe Leu Cys Ser Val Asn
                405                 410                 415
Gly Leu Cys Val Pro Ala Cys Asp Gly Val Lys Asp Cys Pro Asn Gly
            420                 425                 430
Leu Asp Glu Arg Asn Cys Val Cys Arg Ala Thr Phe Gln Cys Lys Glu
        435                 440                 445
Asp Ser Thr Cys Ile Ser Leu Pro Lys Val Cys Asp Gly Gln Pro Asp
450                 455                 460
Cys Leu Asn Gly Ser Asp Glu Glu Gln Cys Gln Gly Val Pro Cys
465                 470                 475                 480
Gly Thr Phe Thr Phe Gln Cys Glu Asp Arg Ser Cys Val Lys Lys Pro
                485                 490                 495
Asn Pro Gln Cys Asp Gly Arg Pro Asp Cys Arg Asp Gly Ser Asp Glu
            500                 505                 510
Glu His Cys Asp Cys Gly Leu Gln Gly Pro Ser Ser Arg Ile Val Gly
        515                 520                 525
Gly Ala Val Ser Ser Glu Gly Glu Trp Pro Trp Gln Ala Ser Leu Gln
530                 535                 540
Val Arg Gly Arg His Ile Cys Gly Gly Ala Leu Ile Ala Asp Arg Trp
545                 550                 555                 560
Val Ile Thr Ala Ala His Cys Phe Gln Glu Asp Ser Met Ala Ser Thr
                565                 570                 575
Val Leu Trp Thr Val Phe Leu Gly Lys Val Trp Gln Asn Ser Arg Trp
            580                 585                 590
Pro Gly Glu Val Ser Phe Lys Val Ser Arg Leu Leu Leu His Pro Tyr
        595                 600                 605
His Glu Glu Asp Ser His Asp Tyr Asp Val Ala Leu Leu Gln Leu Asp
610                 615                 620
His Pro Val Val Arg Ser Ala Ala Val Arg Pro Val Cys Leu Pro Ala
625                 630                 635                 640
Arg Ser His Phe Phe Glu Pro Gly Leu His Cys Trp Ile Thr Gly Trp
                645                 650                 655
Gly Ala Leu Arg Glu Gly Gly Pro Ile Ser Asn Ala Leu Gln Lys Val
            660                 665                 670
Asp Val Gln Leu Ile Pro Gln Asp Leu Cys Ser Glu Val Tyr Arg Tyr
        675                 680                 685
Gln Val Thr Pro Arg Met Leu Cys Ala Gly Tyr Arg Lys Gly Lys Lys
690                 695                 700
Asp Ala Cys Gln Gly Asp Ser Gly Gly Pro Leu Val Cys Lys Ala Leu
```

-continued

| 705 | | | | | | 710 | | | | | 715 | | | | | 720 | |
|---|---|---|---|---|---|---|---|---|---|---|---|---|---|---|---|---|---|
| Ser | Gly | Arg | Trp | Phe<br>725 | Leu | Ala | Gly | Leu | Val<br>730 | Ser | Trp | Gly | Leu | Gly<br>735 | Cys |
| Gly | Arg | Pro | Asn<br>740 | Tyr | Phe | Gly | Val | Tyr<br>745 | Thr | Arg | Ile | Thr | Gly<br>750 | Val | Ile |
| Ser | Trp | Ile<br>755 | Gln | Gln | Val | Val | Thr<br>760 | Gly | Gly | Gly | Ser<br>765 | Gly | Gly | Gly |
| Gly | Ser<br>770 | Gly | Gly | Gly | Ser<br>775 | Asp | Tyr | Lys | Asp<br>780 | Asp | Asp | Lys |

What is claimed is:

1. An anti-type II transmembrane serine protease 6 (TMPRSS6) antibody comprising a HC CDR1, a HC CDR2, and a HC CDR3 of a heavy chain variable region (VH) that comprises the amino acid sequence of SEQ ID NO: 21 or 51, and a LC CDR1, a LC CDR2, and a LC CDR3 of a light chain variable region (VL) of SEQ ID NO: 26 or 56.

2. The anti-TMPRSS6 antibody of claim 1, wherein the HC CDR1, HC CDR2, HC CDR3, LC CDR1, LC CDR2, and LC CDR3 are defined by Kabat definition.

3. The anti-TMPRSS6 antibody of claim 1, wherein the antibody is a humanized antibody.

4. The anti-TMPRSS6 antibody of claim 3, wherein the HC CDR1, HC CDR2, HC CDR3, LC CDR1, LC CDR2, and LC CDR3 are grafted into a framework comprising variable regions derived from a human immunoglobulin framework.

5. The anti-TMPRSS6 antibody of claim 1, wherein the antibody comprises a heavy chain variable region comprising the amino acid sequence of SEQ ID NO: 21 or 51.

6. The anti-TMPRSS6 antibody of claim 1, wherein the antibody comprises a light chain variable region comprising the amino acid sequence of SEQ ID NO: 26 or 56.

7. The anti-TMPRSS6 antibody of claim 5, wherein the antibody comprises a light chain variable region comprising the amino acid sequence of SEQ ID NO: 26 or 56.

8. The anti-TMPRSS6 antibody of claim 1, wherein the antibody is a full-length antibody, a Fab fragment, or a single-chain variable fragment (scFv).

9. The anti-TMPRSS6 antibody of claim 1, wherein the antibody comprises a heavy chain constant region of IgG1.

10. The anti-TMPRSS6 antibody of claim 1, wherein the antibody comprises a heavy chain comprising the amino acid sequence of SEQ ID NO: 69 or 81.

11. The anti-TMPRSS6 antibody of claim 1, wherein the antibody comprises a light chain comprising the amino acid sequence of SEQ ID NO: 71 or 83.

12. The anti-TMPRSS6 antibody of claim 10, wherein the antibody comprises a light chain comprising the amino acid sequence of SEQ ID NO: 71 or 83.

13. The anti-TMPRSS6 antibody of claim 1, wherein the antibody cross-reacts with at least one non-human TMPRSS6.

14. The anti-TMPRSS6 antibody of claim 13, wherein the non-human TMPRSS6 is a mouse TMPRSS6 or a non-human primate TMPRSS6.

15. The anti-TMPRSS6 antibody of claim 1, wherein the antibody specifically binds to human TMPRSS6.

16. The anti-TMPRSS6 antibody of claim 1, wherein the antibody does not specifically bind to human matriptase-1 or human matriptase-3.

17. A composition comprising the anti-TMPRSS6 of claim 1 and a pharmaceutically acceptable carrier.

18. An isolated nucleic acid encoding the heavy chain variable region and/or the light chain variable region of the antibody of claim 1.

19. A vector comprising the isolated nucleic acid of claim 18.

20. A host cell comprising the vector of claim 19.

* * * * *